US007635701B2

(12) United States Patent
Eatherton et al.

(10) Patent No.: US 7,635,701 B2
(45) Date of Patent: Dec. 22, 2009

(54) PYRIMIDINE DERIVATIVES AND THEIR USE AS CB2 MODULATORS

(75) Inventors: Andrew John Eatherton, Welwyn (GB); Gerard Martin Paul Giblin, Welwyn (GB); Richard Howard Green, Stevenage (GB); Jennifer Margaret Doughty, legal representative, Gorham, ME (US); William Leonard Mitchell, Welwyn (GB); Alan Naylor, Harlow (GB); Derek Anthony Rawlings, Welwyn (GB); Brian Peter Slingsby, Welwyn (GB); Andrew Richard Whittington, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 550 days.

(21) Appl. No.: 10/524,470

(22) PCT Filed: Aug. 19, 2003

(86) PCT No.: PCT/EP03/09217

§ 371 (c)(1),
(2), (4) Date: Feb. 28, 2006

(87) PCT Pub. No.: WO2004/018433

PCT Pub. Date: Mar. 4, 2004

(65) Prior Publication Data

US 2006/0293354 A1    Dec. 28, 2006

(30) Foreign Application Priority Data

Aug. 21, 2002 (GB) ................... 0219501.4
Apr. 24, 2003 (GB) ................... 0309326.7

(51) Int. Cl.
*C07D 239/42* (2006.01)
*A61K 31/505* (2006.01)
(52) U.S. Cl. .................. 514/275; 544/330; 544/331
(58) Field of Classification Search ................ 544/330, 544/331; 514/275
See application file for complete search history.

(56) References Cited

U.S. PATENT DOCUMENTS

| 5,112,820 A | 5/1992 | Ward et al. |
| 5,811,428 A | 9/1998 | Suto et al. |
| 5,925,768 A | 7/1999 | Barth et al. |
| 6,107,301 A | 8/2000 | Aldrich et al. |
| 6,184,237 B1 | 2/2001 | Mantlo et al. |

FOREIGN PATENT DOCUMENTS

| EP | 0569912 | 11/1993 |
| EP | 0576357 | 12/1993 |
| FR | 2839718 | 11/2003 |
| WO | WO 97/09315 | 3/1997 |
| WO | WO 00/39101 | 7/2000 |
| WO | WO 02/04429 | 1/2002 |
| WO | WO 02/060447 | 8/2002 |
| WO | WO 02/062750 | 8/2002 |
| WO | WO 02/066036 | 8/2002 |
| WO | WO 2004/000807 | 12/2003 |
| WO | WO 2004/018433 | 3/2004 |
| WO | WO 2004/018434 | 3/2004 |
| WO | WO 2004/029026 | 4/2004 |
| WO | WO 2004/029027 | 4/2004 |
| WO | WO 2004/029204 | 4/2004 |
| WO | WO 2004/002964 | 8/2004 |
| WO | WO 2004/085385 | 10/2004 |

OTHER PUBLICATIONS

Souness, J.E. "Immunosuppressive And Anti-flammatory Effect of Cyclic AMP." Immunopharmacology, 2000, 47/2-3; 127-162.
Huang, Z., et al. "Next Generation of PDE4 Inhibitors." Current Opinion in Chemical Biology, 2001, pp. 432-438.
Sullivan, R. W., et al. 2-Chloro-4-(trifluoromethyl)pyrimidine-5-N-(3',5'-bis(trifluoromethyl)phenyl-carboxamic Potent Inhibitor of NF-KB-and AP-1-Mediated Gene Expression Identified Using Solution-Phase Combinatorial Chemistry; J. Med. Chem.; 1998; 41; 413-419.
Huffman, J.W. "The Search For Selective Ligands For The CB2 Receptor." Currently Pharmaceutical Design, Bentham Science Publishers, vol. 6., No. 13, 2000, pp. 1323-1337.
Gerard M.P. Giblin et al; Discovery of 2-[(2,4-Dichlorophenyl)amino]-N-[(tetrahydro-2H-pyran-4-yl)methyl]-4-(trifluoromethyl)-5-pyrimidinecarboxamide, a Selective CB2 Receptor Agonist for the Treatment of Inflammatory Pain.; J.Med Chem; 2007; 50; 2597-2600; American chemical society; USA.
Hatzelmann, A. et al.; "Anti-Inflammatory and Immunomodulatory Potential of the Novel PDE4 Inhibitor Roflumilast In Vitro."; Journal of Pharmacology and Experimental Therapeutics; 2001; 297 (1); 267-279.
Iwamura H. et al.; "In vitro and in vivo pharmacological characterization of JTE-907, a novel selective ligand for cannabinoid CB2 receptor."; Journal of Pharmacology and Experimental Therapeutics; 2001; 296(2); 420-425.
Malan, T.P. et al.; "CB2 Cannabinoid Receptor Agonists: Pain Relief Without Psychoactive Effects?"; Current Opinion in Pharmacology; 2003; 3; 62-67.
Van Der Mey M. et al.; "Novel selective PDE4 inhibitors. 3. In vivo antiinflammatory activity of a new series of N-substituted cis-tetra- and cis-hexahydrophthalazinones."; Journal of Pharmacology and Experimental Therapeutics; 2001; 45(12); 2520-2525.
Hohmann, A.G. et al.; "Spinal and Peripheral Mechansims of Cannabinoid Antinociception: Behavioral, Neurophysiological and Neuroanatomical Perspectives"; Chemistry and Physics of Lipids; 2002; 121; 173-190.
Farquhar-Smith, W.P. et al.; "Administration of Endocannabinoids Prevents a Referred Hyperalgesia Associated with Inflammation of the Urinary Bladder"; Anesthesiology; 2001; 94; 507-513.

(Continued)

*Primary Examiner*—Deepak Rao
(74) *Attorney, Agent, or Firm*—J. Scott Young

(57) ABSTRACT

The present invention relates to novel pyrimidine derivatives, pharmaceutical compositions containing these compounds and their use in the treatment of diseases, particularly pain, which diseases are caused directly or indirectly by an increase or decrease in activity of the cannabinoid receptor.

19 Claims, No Drawings

OTHER PUBLICATIONS

Jaggar, S.I. et al.; "The Anti-Hyperalgesic Actions of the Cannabinoid Anandamide and the Putative CB2 Receptor Agonist Palmitoylethanolamide in Visceral and Somatic Inflammatory Pain"; Pain; 1998; 76; 189-199.

Kehl, L.J. et al.; "A cannabinoid Agonist Differentially Attenuates Deep Tissue Hyperalgesia in Animal Models of Cancer and Inflammatory Muscle Pain"; Pain; 2003; 103; 175-186.

Goya, P. et al.; "Cannabinoids and Neuropathic Pain"; Mini Reviews in Medicinal Chemistry; 2003; 3; 765-772.

Yao, B.B. et al.; "In Vitro and In Vivo Characterization of A-796260: A Selective Cannabinoid CB2 Receptor Agonist Exhibiting Analgesic Activity in Rodent Pain Models"; British Journal of Pharmacology; 2008; 153; 390-401.

Pertwee, R.G. et al.; "Cannabinoid Receptors and Pain"; Progress in Neurobiology; 2001; 63; 569-611.

Jhaveri, M.D. et al.; "Cannabinoid CB2 Receptor-Mediated Antinociception in Models of Acute and Chronic Pain"; Molecular Neurobiology; 2007; 36; 26-35.

Izzo A.A. et al.; "The Cannabinoid CB2 Receptor: A Good Friend in the Gut"; Neurogastroenterology Motility; 2007; 19; 704-708.

Malan, T.P. et al.; "Inhibition of Pain Responses By Activation of CB2 Cannabinoid Receptors"; Chemistry and Physics of Lipids; 2002; 121; 191-200.

PYRIMIDINE DERIVATIVES AND THEIR USE AS CB2 MODULATORS

CROSS REFERENCES TO RELATED APPLICATIONS

This application is a 371 Application of PCT/EP2003/009217, filed 19 Aug. 2003, which claims priority to GB Application Serial No. 0219501.4, filed 21 Aug. 2002 and 0309326.7, filed 24 Apr. 2003.

The present invention relates to novel pyrimidine derivatives, pharmaceutical compositions containing these compounds and their use in the treatment of diseases, particularly pain, which diseases are caused directly or indirectly by an increase or decrease in activity of the cannabinoid receptor.

Cannabinoids are a specific class of psychoactive compounds present in Indian *cannabis* (*Cannabis sativa*), including about sixty different molecules, the most representative being cannabinol, cannabidiol and several isomers of tetrahydrocannabinol. Knowledge of the therapeutic activity of *cannabis* dates back to the ancient dynasties of China, where, 5,000 years ago, *cannabis* was used for the treatment of asthma, migraine and some gynaecological disorders. These uses later became so established that, around 1850, *cannabis* extracts were included in the US Pharmacopaeia and remained there until 1947.

Cannabinoids are known to cause different effects on various systems and/or organs, the most important being on the central nervous system and on the cardiovascular system. These effects include alterations in memory and cognition, euphoria, and sedation. Cannabinoids also increase heart rate and vary systemic arterial pressure. Peripheral effects related to bronchial constriction, immunomodulation, and inflammation have also been observed. The capability of cannabinoids to reduce intraocular pressure and to affect respiratory and endocrine systems is also well documented. See e.g. L. E. Hollister, Health Aspects of *Cannabis, Pharmacological Reviews*, Vol. 38, pp. 1-20, (1986). More recently, it was found that cannabinoids suppress the cellular and humoral immune responses and exhibit anti-inflammatory properties. Wirth et al., Anti-inflammatory Properties of Cannabichrome, *Life Science, Vol*. 26, pp. 1991-1995, (1980).

In spite of the foregoing benefits, the therapeutic use of *cannabis* is controversial, both due to its relevant psychoactive effects (causing dependence and addiction), and due to manifold side effects that have not yet been completely clarified. Although work in this field has been ongoing since the 1940's, evidence indicating that the peripheral effects of cannabinoids are directly mediated, and not secondary to a CNS effect, has been limited by the lack of receptor characterisation, the lack of information concerning an endogenous cannabinoid ligand and, until recently, the lack of receptor sub-type selective compounds.

The first cannabinoid receptor was found to be mainly located in the brain, in neural cell lines, and, only to a lesser extent, at the peripheral level. In view of its location, it was called the central receptor ("CB1"). See Matsuda et al., "Structure of a Cannabinoid Receptor and Functional Expression of the Cloned cDNA," *Nature*, Vol. 346, pp. 561-564 (1990. The second cannabinoid receptor ("CB2") was identified in the spleen, and was assumed to modulate the non psychoactive effects of the cannabinoids. See Munro et al., "Molecular Characterization of a Peripheral Receptor for Cannabinoids," *Nature. Vol*. 365, pp. 61-65 (1993).

Recently, some compounds have been prepared which are capable of acting as agonists on both the cannabinoid receptors. For example, use of derivatives of dihydroxypyrrole-1,2,3-d,e)-1,4-benzoxazine in the treatment of glaucoma and the use of derivatives of 1,5-diphenyl-pyrazole as immunomodulators or psychotropic agents in the treatment of various neuropathologies, migraine, epilepsy, glaucoma, etc are known. See U.S. Pat. No. 5,112,820 and EP 576357, respectively. However, because these compounds are active on both the CB1 and CB2 receptor, they can lead to serious psychoactive effects.

The foregoing indications and the preferential localisation of the CD2 receptor in the immune system confirms a specific role of CB2 in modulating the immune and anti-inflammatory response to stimuli of different sources.

The total size of the patient population suffering from pain is vast (almost 300 million), dominated by those suffering from back pain, osteo-arthritic pain and post-operative pain.

Neuropathic pain (associated with neuronal lesions such as those induced by diabetes, HIV, herpes infection, or stroke) occurs with lower, but still substantial prevalence, as does cancer pain.

The pathogenic mechanisms that give rise to pain symptoms can be grouped into two main categories:
- those that are components of inflammatory tissue responses (Inflammatory Pain);
- those that result from a neuronal lesion of some form (Neuropathic Pain).

Chronic inflammatory pain consists predominantly of osteo-arthritis, chronic low back pain and rheumatoid arthritis. The pain results from acute and on-going injury and/or inflammation. There may be both spontaneous and provoked pain.

There is an underlying pathological hypersensitivity as a result of physiological hyperexcitability and the release of inflammatory mediators which further potentiate this hyperexcitability. CB2 receptors are expressed on inflammatory cells (T cells, B cells, macrophages, mast cells) and mediate immune suppression through inhibition of cellular interaction/inflammatory mediator release. CB2 receptors may also be expressed on sensory nerve terminals and therefore directly inhibit hyperalgesia.

The role of CB2 in immunomodulation, inflammation, osteoporosis, cardiovascular, renal and other disease conditions is now being examined. In light of the fact that cannabinoids act on receptors capable of modulating different functional effects, and in view of the low homology between CB2 and CB1, the importance of developing a class of drugs selective for the specific receptor sub-type is evident. The natural or synthetic cannabinoids currently available do not fulfil this function because they are active on both receptors.

Based on the foregoing, there is a need for compounds which are capable of selectively modulating the receptor for cannabinoids and, therefore, the pathologies associated with such receptors. Thus, CB2 modulators offer a unique approach toward the pharmacotherapy of immune disorders, inflammation, osteoporosis, renal ischemia and other pathophysiological conditions.

The present invention provides novel pyrimidine derivatives of formula (I) and pharmaceutically acceptable derivatives thereof, pharmaceutical compositions containing these compounds or derivatives, and their use as CB2 receptor modulators, which are useful in the treatment of a variety of disorders.

The present invention further comprises a method for treating disease mediated by CB2 receptors in an animal, including humans, which comprises administering to an animal in need thereof an effective amount of a compound of formula (I) or a pharmaceutically acceptable derivative thereof.

The invention provides compounds of formula (I):

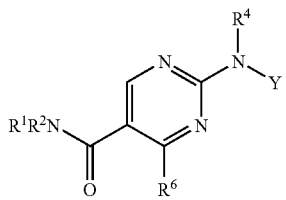

wherein:

Y is phenyl, optionally substituted with one, two or three substituents;

$R^1$ is selected from hydrogen, $C_{1-6}$ alkyl, $C_{3-6}$ cycloalkyl and halosubstituted$C_{1-6}$alkyl;

$R^2$ is $(CH_2)_m R^3$ where m is 0 or 1;

or $R^1$ and $R^2$ together with N to which they are attached form an optionally substituted 4 to 8-membered non-aromatic heterocyclyl ring;

$R^3$ is an optionally substituted 4- to 8-membered non-aromatic heterocyclyl group, an optionally substituted $C_{3-8}$ cycloalkyl group, an optionally substituted straight or branched $C_{1-10}$ alkyl, a $C_{5-7}$ cycloalkenyl or $R^5$;

$R^4$ is selected from hydrogen, $C_{1-6}$ alkyl, $C_{3-6}$ cycloalkyl, or halosubstituted$C_{1-6}$ alkyl, $COCH_3$, and $SO_2Me$;

$R^5$ is

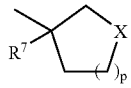

wherein p is 0, 1 or 2 and X is $CH_2$ or O;

$R^6$ is methyl, chloro or CHxFn wherein n is 1, 2, or 3, x is 0, 1 or 2 and n and x add up to 3;

$R^7$ is OH, $C_{1-6}$alkoxy, $NR^{8a}R^{8b}$, $NHCOR^9$, $NHSO_2R^9$, $SOqR^9$;

$R^{8a}$ is H or $C_{1-6}$alkyl;

$R^{8b}$ is H or $C_{1-6}$alkyl;

$R^9$ is $C_{1-6}$alkyl;

q is 0, 1 or 2;

and pharmaceutically acceptable derivatives thereof.

In one particular embodiment Y is a substituted phenyl.

In one particular embodiment Y is substituted by 1 or 2 substituents. If mono-substituted, in one particular embodiment the substituent is in the 3 position. If di-substituted, in one particular embodiment the substituents are in the 2- and 4-positions.

When Y is substituted, the substituent or substituents are preferably selected from $C_{1-6}$ alkyl, halosubstituted$C_{1-6}$ alkyl, $C_{1-6}$ alkoxy, a hydroxy group, a cyano group, halo, a $C_{1-6}$alkylsulfonyl group, —$CONH_2$, —$NHCOCH_3$ and —COOH. Furthermore the substituent or substituents can be selected from halosubstituted$C_{1-6}$alkoxy, and $SO_2NR^{8a}R^{8b}$ wherein $R^{8a}$ and $R^{8b}$ are as defined above. Additionally the substituent or substiuents can be $SC_{1-6}$alkyl.

In one particular embodiment Y is substituted by chloro, fluoro, bromo, cyano, $CF_3$, methyl, $CF_3O$— or $SCH_3$ and methoxy; more particularly halo, cyano or methoxy.

In one particular embodiment the compound of formula (I) is a compound of formula (Ia)

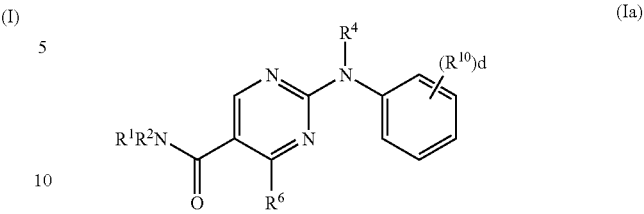

wherein;

$R^1$ is selected from hydrogen, $C_{1-6}$ alkyl, $C_{3-6}$ cycloalkyl and halosubstituted$C_{1-6}$ alkyl;

$R^2$ is $(CH_2)_m R^3$ where m is 0 or 1;

or $R^1$ and $R^2$ together with N to which they are attached form a 4- to 8-membered non-aromatic ring selected from azetidinyl, pyrrolidinyl, morpholinyl, piperizinyl, piperidinyl, tetrahydropyridinyl, azapine, oxapine, azacyclooctanyl, azaoxacyclooctanyl and azathiacyclooctanyl any of which can be unsubstituted or substituted by one, two or three substituents selected from $C_{1-6}$ alkyl, $C_{1-6}$ alkoxy, a hydroxy group, a cyano group, halo, sulfonyl group, methylsulfonyl, $NR^{8a}R^{8b}$, $NHCOCH_3$, (=O), and —$CONHCH_3$.

$R^3$ is 2- or 3-azetidinyl, oxetanyl, thioxetanyl, thioxetanyl-s-oxide, thioxetanyl-s,s-dioxide, dioxalanyl, pyrrolidinyl, tetrahydrofuranyl, tetrahydrothiophenyl, morpholinyl, piperidinyl, piperzinyl, tetrahydropyranyl, tetrahydrothiopyranyl, thiomorpholinyl, thiomorpholinyl-s,s-dioxide, tetrahydropyridinyl, azapine, oxapine, azacyclooctanyl, azaoxacyclooctanyl, azathiacyclooctanyl, oxacylcooctanyl, thiacyclooctanyl, a $C_{3-8}$ cycloalkyl group, a straight or branched $C_{1-10}$ alkyl, a $C_{5-7}$ cycloalkenyl or $R^5$, any of which can be unsubstituted or substituted by one, two or three substituents selected from $C_{1-6}$ alkyl, $C_{1-6}$ alkoxy, a hydroxy group, a cyano group, halo, sulfonyl group, methylsulfonyl, $NR^{8a}R^{8b}$, $NHCOCH_3$, (=O), and —$CONHCH_3$;

$R^{10}$ is selected from $C_{1-6}$ alkyl, halosubstituted$C_{1-6}$ alkyl, $C_{1-6}$ alkoxy, a hydroxy group, a cyano group, halo, a $C_{1-6}$alkyl sulfonyl group, —$CONH_2$, —$NHCOCH_3$, —COOH, halosubstituted$C_{1-6}$alkoxy, $SC_{1-6}$alkyl and $SO_2NR^{8a}R^{8b}$;

$R^4$ is selected from hydrogen, $C_{1-6}$ alkyl, $C_{3-6}$ cycloalkyl, or halosubstituted$C_{1-6}$ alkyl, $COCH_3$, and $SO_2Me$;

$R^5$ is

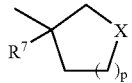

wherein p is 0, 1 or 2 and X is $CH_2$ or O;

$R^6$ is methyl, chloro or CHxFn wherein n is 1, 2, or 3, x is 0, 1 or 2 and n and x add up to 3;

$R^7$ is OH, $C_{1-6}$alkoxy, $NR^{8a}R^{8b}$, $NHCOR^9$, $NHSO_2R^9$, $SOqR^9$;

$R^{8a}$ is H or $C_{1-6}$alkyl;

$R^{8b}$ is H or $C_{1-6}$alkyl;

$R^9$ is $C_{1-6}$alkyl;

q is 0, 1 or 2;

d is 0, 1, 2 or 3 and pharmaceutically acceptable derivatives thereof.

In one particular embodiment $R^1$ is hydrogen.

In one particular embodiment $R^4$ is $C_{1-6}$alkyl or hydrogen, more preferably methyl or hydrogen even more preferably hydrogen.

Alternatively R¹ and R² together with N to which they are attached form an optionally substituted 5- or 6-membered non-aromatic heterocyclyl ring.

When R¹ and R² together with N to which they are attached form a 4- to 8-membered non-aromatic heterocyclyl ring which is substituted, or when R³ is substituted, the substituent or substituents are preferably selected from: $C_{1-6}$ alkyl, $C_{1-6}$ alkoxy, a hydroxy group, a cyano group, halo or a sulfonyl group. Additionally the optional substituent(s) can be choosen from methylsulfonyl, $NR^{8a}R^{8b}$, $NHCOCH_3$, (=O), or —$CONHCH_3$.

In one particular embodiment $R^6$ is CHxFn, for example $CF_3$, $CHF_2$, $CH_2F$, more preferably $CF_3$.

In one particular embodiment $R^5$ is

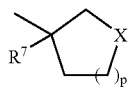

wherein p is 0, 1 or 2;

In one particular embodiment $R^7$ is OH.

In one particular embodiment $R^3$ is an optionally substituted 4- to 8-membered non-aromatic heterocyclyl group, an optionally substituted $C_{3-8}$ cycloalkyl group, an optionally substituted straight or branched $C_{1-10}$ alkyl or $R^5$.

In one particular embodiment when $R^3$ is an optionally substituted $C_{3-8}$ cycloalkyl group or an optionally substituted 4- to 8-membered nonaromatic heterocyclyl, m is 1.

In one particular embodiment $R^3$ is an optionally substituted $C_{3-6}$ cycloalkyl group or an optionally substituted 4- or 6-membered nonaromatic heterocyclyl.

In one particular embodiment R¹ and R² together with N to which they are attached form a 4- to 8-membered non-aromatic heterocyclyl ring which is selected from pyrrolidinyl, morpholinyl, piperizinyl, piperidinyl and tetrahydropyridinyl.

In one particular embodiment when R³ is nonaromatic heterocyclyl it is selected from pyrrolidinyl, tetrahydrofuranyl, tetrahydrothiophenyl, morpholinyl, piperidinyl, piperazinyl, tetrahydropyranyl, tetrahydrothiopyranyl, thiomorpholinyl, thiomorpholinyl-s,s-dioxide, tetrahydropyridinyl.

In one particular embodiment the compound of formula (I) is a compound of formula (Ib)

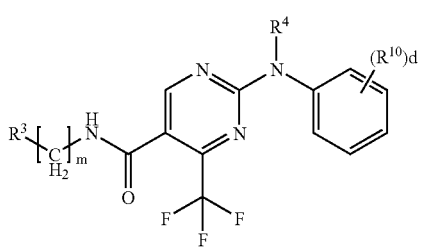

wherein;

R³ is pyrrolidinyl, tetrahydrofuranyl, tetrahydrothiophenyl, morpholinyl, piperidinyl, piperazinyl, tetrahydropyranyl, tetrahydrothiopyranyl, thiomorpholinyl, thiomorpholinyl-s,s-dioxide, tetrahydropyridinyl, a $C_{3-8}$ cycloalkyl group, any of which can be unsubstituted or substituted by one, two or three substituents selected from $C_{1-6}$ alkyl, $C_{1-6}$ alkoxy, a hydroxy group, a cyano group, halo, sulfonyl group, methylsulfonyl, $NR^{8a}R^{8b}$, $NHCOCH_3$, (=O), and —$CONHCH_3$;

$R^{10}$ is selected from chloro, fluoro, bromo, cyano, $CF_3$, methyl, $CF_3O$— or $SCH_3$ and methoxy;

$R^4$ is selected from hydrogen or methyl;

$R^{8a}$ is H or $C_{1-6}$ alkyl;

$R^{8b}$ is H or $C_{1-6}$ alkyl;

m is 0 or 1 d is 0, 1, 2 or 3 and and pharmaceutically acceptable derivatives thereof.

In one particular embodiment m is 1.

In one particular embodiment the compound of formula (I) is a compound of formula (Ic)

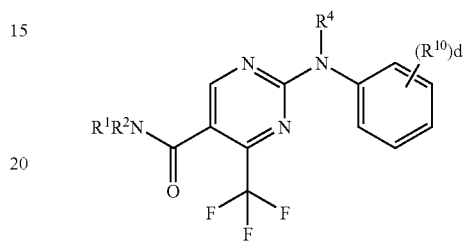

wherein;

R¹ and R² together with N to which they are attached form a 5- to 6-membered non-aromatic ring selected from pyrrolidinyl, morpholinyl, piperizinyl, piperidinyl and tetrahydropyridinyl, any of which can be unsubstituted or substituted by one, two or three substituents selected from $C_{1-6}$ alkyl, $C_{1-6}$ alkoxy, a hydroxy group, a cyano group, halo, sulfonyl group, methylsulfonyl, $NR^{8a}R^{8b}$, $NHCOCH_3$, (=O), and —$CONHCH_3$.

$R^{10}$ is selected from chloro, fluoro, bromo, cyano, $CF_3$, methyl, $CF_3O$— or $SCH_3$ and methoxy;

$R^4$ is hydrogen or methyl;

$R^{8a}$ is H or $C_{1-6}$ alkyl;

$R^{8b}$ is H or $C_{1-6}$ alkyl;

d is 0, 1, 2 or 3 and and pharmaceutically acceptable derivatives thereof.

In one particular embodiment the compounds are selective for CB2 over CB1. Preferably the compounds are 100 fold selective i.e. compounds of formula (I) have an EC50 value at the cloned human cannabinoid CB2 receptor of at least 100 times the EC50 values at the cloned humna cannabinoid CB1 receptor or have less than 10% efficacy at the CB1 receptor.

The invention is described using the following definitions unless otherwise indicated.

The term "pharmaceutically acceptable derivative" means any pharmaceutically acceptable salt, ester, salt of such ester or solvate of the compounds of formula (I), or any other compound which upon administration to the recipient is capable of providing (directly or indirectly) a compound of formula (I) or an active metabolite or residue thereof.

It will be appreciated by those skilled in the art that compounds of formula (I) may be modified to provide pharmaceutically acceptable derivatives thereof at any of the functional groups in the compounds, and that the compounds of formula (I) may be derivatised at more than one position.

It will be appreciated that, for pharmaceutical use, the salts referred to above will be physiologically acceptable salts, but other salts may find use, for example in the preparation of compounds of formula (I) and the physiological acceptable salts thereof. Pharmaceutically acceptable salts include those described by Berge, Bighley and Mondkhouse, J. Pharm. Sci., 1977, 66, 1-19. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropyl amine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tataric, p-toluenesulfonic acid, and the like.

Preferred examples of pharmaceutically acceptable salts include the ammonium, calcium, magnesium, potassium, and sodium salts, and those formed from maleic, fumaric, benzoic, ascorbic, pamoic, succinic, hydrochloric, sulfuric, bis-methylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

The terms 'halogen or halo' are used to represent fluorine, chlorine, bromine or iodine.

The term 'alkyl' as a group or part of a group means a straight or branched chain alkyl group or combinations thereof, for example a methyl, ethyl, n-propyl, i-propyl, n-butyl, s-butyl, t-butyl, pentyl, hexyl, 1,1-dimethylethyl, or combinations thereof.

The term 'alkoxy' as a group or as part of a group means a straight, branched or cyclic chain alkyl group having an oxygen atom attached to the chain, for example a methoxy, ethoxy, n-propoxy, i-propoxy, n-butoxy, s-butoxy, t-butoxy group, pentoxy, hexyloxy group, cyclopentoxy or cyclohexyloxy group.

The term 'cycloalkyl' means a closed non-aromatic ring, for example cyclobutyl, cyclopentyl, cyclohexyl or cycloheptyl, or cyclooctyl.

The term 'cycloalkenyl" as a group or part of a group means a non-aromatic ring, containing at least one CH=CH moiety for example cyclobutenyl, cyclopentenyl, cyclohexenyl or cycloheptenyl, or cyclooctenyl.

When $R^1$ and $R^2$ taken together with the N to which they are attached form an optionally substituted heterocyclyl ring, the ring may optionally contain 1, 2, 3 or 4 further heteroatoms. The ring may be saturated or unsaturated. Preferably the further heteroatoms are selected from oxygen, nitrogen or sulphur. An example of a 4-membered heterocyclyl ring is azetidinyl. Examples of 5-membered heterocyclyl rings include pyrrolidinyl. Examples of 6-membered heterocyclyl rings are morpholinyl, piperizinyl or piperidinyl. An additional example is tetrahydropyridinyl. Examples of a 7-membered heterocyclyl ring are azapine or oxapine. Examples of 8-membered heterocyclyl rings are azacyclooctanyl, azaoxacyclooctanyl or azathiacyclooctanyl.

When $R^3$ is an optionally substituted non-aromatic heterocyclyl group, the ring may contain 1, 2, 3, or 4 heteroatoms. Preferably the heteroatoms are selected from oxygen, nitrogen or sulphur. Examples of 4-membered groups are 2- or 3-azetidinyl, oxetanyl, thioxetanyl, thioxetanyl-s-oxide, thioxetanyl-s,s-dioxide. Examples of 5-membered heterocyclyl groups in this instance include dioxalanyl, pyrrolidinyl or tetrahydrofuranyl or tetrahydrothiophenyl. Examples of 6-membered heterocyclyl groups are morpholinyl, piperidinyl, piperazinyl, tetrahydropyranyl, tetrahydrothiopyranyl, thiomorpholinyl or thiomorpholinyl-s,s-dioxide. An additional example is tetrahydropyridinyl. Examples of a 7-membered heterocyclyl ring are azapine or oxapine. Examples of 8-membered groups are azacyclooctanyl, azaoxacyclooctanyl or azathiacyclooctanyl, oxacylcooctanyl, or thiacyclooctanyl.

In one particular embodiment compounds of the present invention can be selected from:

1-[2-(3-Chlorophenylamino)-4-trifluoromethylpyrimidin-5-yl]-1-piperidin-1-ylmethanone;

2-(3-Chlorophenylamino)-4-trifluoromethylpyrimidine-5-carboxylic acid cyclopentylmethyl-amide;

1-[2-(3-Chlorophenylamino)-4-trifluoromethylpyrimidin-5-yl]-1-morpholin-4-yl-methanone;

2-(3-Chlorophenylamino)-4-trifluoromethylpyrimidine-5-carboxylic acid cyclohexylmethyl-amide;

2-Phenylamino-4-trifluoromethylpyrimidine-5-carboxylic acid cyclohexylmethyl-amide;

1-[2-(2,3-Dichlorophenylamino)-4-trifluoromethylpyrimidin-5-yl]-1-morpholin-4-yl-methanone;

1-[2-(2,4-Dichlorophenylamino)-4-trifluoromethylpyrimidin-5-yl]-1-morpholin-4-yl-methanone;

1-[2-(3,4-Dichlorophenylamino)-4-trifluoromethylpyrimidin-5-yl]-1-morpholin-4-yl-methanone;

1-[2-(2,5-Dichlorophenylamino)-4-trifluoromethylpyrimidin-5-yl]-1-morpholin-4-yl-methanone;

1-[2-(3-Fluorophenylamino)-4-trifluoromethylpyrimidin-5-yl]-1-morpholin-4-yl-methanone;

1-[2-(3-Bromophenylamino)-4-trifluoromethylpyrimidin-5-yl]-1-morpholin-4-yl-methanone;

1-[2-(3-Bromophenylamino)-4-trifluoromethylpyrimidin-5-yl]-1-piperidin-4-yl-methanone;

1-[2-(3,5-Dichlorophenylamino)-4-trifluoromethylpyrimidin-5-yl]-1-morpholinyl-methanone;

2-(3-Chlorophenylamino)-4-trifluoromethylpyrimidin-5-carboxylic acid cyclopentylamide;

2-(2,3-Dichlorophenylamino)-4-trifluoromethylpyrimidine-5-carboxylic acid cyclohexylmethyl-amide;

2-(2,4-Dichlorophenylamino)-4-trifluoromethylpyrimidine-5-carboxylic acid cyclohexylmethyl-amide;

2-(3,4-Dichlorophenylamino)-4-trifluoromethylpyrimidine-5-carboxylic acid cyclohexylmethyl-amide;

2-(3,5-Dichlorophenylamino)-4-trifluoromethylpyrimidine-5-carboxylic acid cyclohexylmethyl-amide 2-(3-Fluorophenylamino)-4-trifluoromethylpyrimidine-5-carboxylic acid cyclohexylmethyl-amide;

2-(3-Bromophenylamino)-4-trifluoromethylpyrimidine-5-carboxylic acid cyclohexylmethyl-amide;

2-(2,6-Dichlorophenylamino)-4-trifluoromethylpyrimidine-5-carboxylic acid cyclohexylmethyl-amide;

2-(3-Chlorophenylamino)-4-trifluoromethylpyrimidine-5-carboxylic acid (tetrahydro-pyran-4-ylmethyl)-amide;

2-(3-Chlorophenylamino)-4-trifluoromethylpyrimidin-5-carboxylic acid cyclobutylamide;

2-(3-Fluorophenylamino)-4-trifluoromethylpyrimidine-5-carboxylic acid (tetrahydropyran-4-ylmethyl)-amide;

2-(3-Bromophenylamino)-4-trifluoromethylpyrimidine-5-carboxylic acid (tetrahydropyran-4-ylmethyl)-amide;
2-(2,3-Dichlorophenylamino)-4-trifluoromethylpyrimidine-5-carboxylic acid (tetrahydropyran-4-ylmethyl)-amide;
2-(2,4-Dichlorophenylamino)-4-trifluoromethylpyrimidine-5-carboxylic acid (tetrahydropyran-4-ylmethyl)-amide;
2-(2,5-Dichlorophenylamino)-4-trifluoromethylpyrimidine-5-carboxylic acid (tetrahydropyran-4-ylmethyl)-amide;
2-(3,5-Dichlorophenylamino)-4-trifluoromethylpyrimidine-5-carboxylic acid (tetrahydropyran-4-ylmethyl)-amide;
2-(3-Methoxyphenylamino)-4-trifluoromethylpyrimidine-5-carboxylic acid (tetrahydropyran-4-ylmethyl)-amide;
2-(3-Fluorophenylamino)-4-trifluoromethylpyrimidine-5-carboxylic acid (cyclopentylmethyl)-amide;
2-(3-Bromophenylamino)-4-trifluoromethylpyrimidine-5-carboxylic acid (cyclopentylmethyl)-amide;
2-(2,3-Dichlorophenylamino)-4-trifluoromethylpyrimidine-5-carboxylic acid cyclopentylmethyl-amide;
2-(2,4-Dichlorophenylamino)-4-trifluoromethylpyrimidine-5-carboxylic acid cyclopentylmethyl-amide;
2-(2,5-Dichlorophenylamino)-4-trifluoromethylpyrimidine-5-carboxylic acid cyclopentylmethyl-amide;
2-(2,6-Dichlorophenylamino)-4-trifluoromethylpyrimidine-5-carboxylic acid cyclopentylmethyl-amide;
2-(3,4-Dichlorophenylamino)-4-trifluoromethylpyrimidine-5-carboxylic acid cyclopentylmethyl amide;
2-(3,5-Dichlorophenylamino)-4-trifluoromethylpyrimidine-5-carboxylic acid cyclopentylmethyl amide;
2-(3-Methoxyphenylamino)-4-trifluoromethylpyrimidine-5-carboxylic acid cyclopentylmethyl-amide;
2-(3-Bromophenylamino)-4-trifluoromethylpyrimidine-5-carboxylic acid cyclobutylamide;
2-(2,3-Dichlorophenylamino)-4-trifluoromethylpyrimidine-5-carboxylic acid cyclobutylamide;
2-(2,4-Dichlorophenylamino)-4-trifluoromethylpyrimidine-5-carboxylic acid cyclobutylamide;
2-(2,5-Dichlorophenylamino)-4-trifluoromethylpyrimidine-5-carboxylic acid cyclobutylamide;
2-(2,6-Dichlorophenylamino)-4-trifluoromethylpyrimidine-5-carboxylic acid cyclobutylamide;
2-(3,5-Dichlorophenylamino)-4-trifluoromethylpyrimidine-5-carboxylic acid cyclobutylamide;
2-(3-Methoxyphenylamino)-4-trifluoromethylpyrimidine-5-carboxylic acid cyclobutylamide;
2-(3-Chlorophenylamino)-4-trifluoromethylpyrimidine-5-carboxylic acid cyclobutylmethyl-amide;
2-(2,6-Dichlorophenylamino)-4-trifluoromethyl-pyrimidine-5-carboxylic acid (tetrahydro-pyran-4-ylmethyl)-amide;
2-(3,4-Dichlorophenylamino)-4-trifluoromethylpyrimidine-5-carboxylic acid (tetrahydro-pyran-4-ylmethyl)-amide;
1-[2-(3,4-Dichlorophenylamino)-4-trifluoromethylpyrimidin-5-yl]-1-(morpholin-4-yl)-methanone;
2-(3-Methoxyphenylamino)-trifluoromethyl-pyrimidine-5-carboxylic acid cyclohexylmethyl-amide;
2-(3-Chlorophenylamino)-4-trifluoromethyl-pyrimidine-5-carboxylic acid (1-hydroxy-cyclohexylmethyl)-amide;
2-(3-Bromophenylamino)-4-trifluoromethyl-pyrimidine-5-carboxylic acid (1-hydroxy-cyclohexylmethyl)-amide;
2-(3-Chlorofluorophenylamino)-4-trifluoromethyl-pyrimidine-5-carboxylic acid cyclohexylmethyl-amide;
2-(3-Chloro-2-fluorophenylamino)-4-trifluoromethyl-pyrimidine-5-carboxylic acid cyclohexylmethyl-amide;
2-(5-Chloro-2-fluorophenylamino)-4-trifluoromethyl-pyrimidine-5-carboxylic acid cyclohexylmethyl-amide;
2-(3,5-Difluorophenylamino)-4-trifluoromethyl-pyrimidine-5-carboxylic acid cyclohexylmethyl-amide;
2-(4-Chloro-2-trifluoromethylphenylamino)-4-trifluoromethyl-pyrimidine-5-carboxylic acid cyclohexylmethyl-amide;
2-(3-Cyanophenylamino)-4-trifluoromethyl-pyrimidin-5-carboxylic acid cyclohexylmethyl-amide;
2-(3-Cyanophenylamino)-4-trifluoromethyl-pyrimidine-5-carboxylic acid (tetrahydropyran-4-ylmethyl)-amide;
2-(3-Cyanophenylamino)-4-trifluoromethyl-pyrimidine-5-carboxylic acid cyclopentylmethyl-amide;
2-(4-Cyanophenylamino)-4-trifluoromethyl-pyrimidine-5-carboxylic acid cyclohexylmethyl-amide;
2-(4-Cyanophenylamino)-4-trifluoromethyl-pyrimidin-5-carboxylic acid (tetrahydropyran-4-ylmethyl)-amide;
2-(4-Cyanophenylamino)-4-trifluoromethyl-pyrimidine-5-carboxylic acid cyclopentylmethyl-amide;
2-(3-Methoxy-5-(trifluoromethyl)phenylamino)-4-trifluoromethyl-pyrimidine-5-carboxylic acid (tetrahydropyran-4-ylmethyl)-amide;
2-(3,5-Bis-trifluoromethyl-phenylamino)-4-trifluoromethyl-pyrimidine-5-carboxylic acid (tetrahydropyran-4-ylmethyl)-amide;
2-(3-Bromo-5-trifluoromethyl)phenylamino)-4-trifluoromethyl-pyrimidine-5-carboxylic acid (tetrahydropyran-4-ylmethyl)-amide;
2-(3-Fluoro-5-(trifluoromethyl)phenylamino)-4-trifluoromethyl-pyrimidine-5-carboxylic acid (tetrahydropyran-4-ylmethyl)-amide;
2-(2-Fluoro-3-(trifluoromethyl)phenylamino)-4-trifluoromethyl-pyrimidine-5-carboxylic acid (tetrahydropyran-4-ylmethyl)-amide;
2-(2-Methylthio-3-(trifluoromethyl)phenylamino)-4-trifluoromethyl-pyridine-5-carboxylic acid (tetrahydropyran-4-ylmethyl)-amide;
2-(5-Chloro-2-methylphenylamino)-4-trifluoromethyl-pyrimidine-5-arboxylic acid (cyclopentylmethyl)-amide;
2-(3-Chloro-4-methylphenylamino)-4-trifluoromethyl-pyrimidine-5-carboxylic acid (tetrahydropyran-4-ylmethyl)-amide;
2-(3-Chloro-2-methylphenylamino)-4-trifluoromethyl-pyrimidine-5-carboxylic acid (tetrahydropyran-4-ylmethyl)-amide;
2-(4-Chloro-3-methoxyphenylamino)-4-trifluoromethyl-pyrimidine-5-carboxylic acid (tetrahydropyran-4-ylmethyl)-amide;
2-(4-Chloro-3-methylphenylamino)-4-trifluoromethyl-pyrimidine-5-carboxylic acid (tetrahydropyran-4-ylmethyl)-amide;
2-(3-Chlorophenylamino)-4-trifluoromethyl-pyrimidine-5-carboxylic acid cyclobutylmethyl-methyl-amide;
2-(3-Chlorophenylamino)-4-trifluoromethyl-pyrimidine-5-carboxylic acid cyclohexylmethyl-methyl-amide;
2-(3-Chlorophenylamino)-4-trifluoromethyl-pyrimidine-5-carboxylic acid cyclopentylmethyl-methyl-amide;
2-(5-Chloro-2-fluorophenylamino)-4-trifluoromethyl-pyrimidine-5-carboxylic acid cyclobutylmethyl-amide;
2-(3,5-Difluorophenylamino)-4-trifluoromethyl-pyrimidine-5-carboxylic acid cyclobutylmethyl-amide;
2-(3-Chloro-4-trifluoromethoxyphenylamino)-4-trifluoromethyl-pyrimidine-5-carboxylic acid cyclobutylmethyl-amide;
2-(3-Chloro-4-fluorophenylamino)-4-trifluoromethyl-pyrimidine-5-carboxylic acid cyclobutylmethyl-amide;
2-(3-Chloro-2-fluorophenylamino)-4-trifluoromethyl-pyrimidine-5-carboxylic acid cyclobutylmethyl-amide;
2-(3-Fluoro-4-trifluoromethylphenylamino)-4-trifluoromethyl-pyrimidine-5-carboxylic acid cyclobutylmethyl-amide;

2-(3-4-cyanophenylamino)-4-trifluoromethyl-pyrimidine-5-carboxylic acid cyclobutylmethyl-amide;
2-(3-Fluorophenylamino)-4-trifluoromethyl-pyrimidine-5-carboxylic acid cyclobutylmethyl-amide;
2-(3-Bromophenylamino)-4-trifluoromethyl-pyrimidine-5-carboxylic acid cyclobutylmethyl-amide;
2-(2,3-Dichlorophenylamino)-4-trifluoromethyl-pyrimidine-5-carboxylic acid cyclobutylmethyl-amide;
2-(2,4-Dichlorophenylamino)-4-trifluoromethyl-pyrimidine-5-carboxylic acid cyclobutylmethyl-amide;
2-(2,5-Dichlorophenylamino)-4-trifluoromethyl-pyrimidine-5-carboxylic acid cyclobutylmethyl-amide;
2-(2,6-Dichlorophenylamino)-4-trifluoromethyl-pyrimidine-5-carboxylic acid cyclobutylmethyl-amide;
2-(3,4-Dichlorophenylamino)-4-trifluoromethyl-pyrimidine-5-carboxylic acid cyclobutylmethyl-amide;
2-(3-Methoxyphenylamino)trifluoromethyl-pyrimidine-5-carboxylic acid cyclobutylmethyl-amide;
2-(3,5-Dichlorophenylamino)-4-trifluoromethyl-pyrimidine-5-carboxylic acid cyclobutylmethyl-amide;
2-(3-Bromophenylamino)-4-trifluoromethyl-pyrimidine-5-carboxylic acid cyclopentylamide;
2-(2,4-Dichlorophenylamino)-4-trifluoromethyl-pyrimidine-5-carboxylic acid cyclopentylamide.
2-(3-Chlorophenylamino)-4-trifluoromethyl-pyrimidine-5-carboxylic acid cyclopropylamide;
2-(3-Chlorophenylamino)-4-trifluoromethyl-pyrimidine-5-carboxylic acid (3,3-dimethylbutyl)-amide;
2-(3-Chlorophenylamino)-4-trifluoromethyl-pyrimidine-5-carboxylic acid methyl-(tetrahydro-pyran-4-ylmethyl)-amide;
2-(2-Fluoro-3-chloro-phenylamino)-4-trifluoromethyl-pyrimidine-5-carboxylic acid (tetrahydro-pyran-4-ylmethyl)-amide;
2-(2-Fluoro-5-chloro-phenylamino)-4-trifluoromethyl-pyrimidine-5-carboxylic acid (tetrahydro-pyran-4-ylmethyl)-amide;
2-(3,5-Difluorophenylamino)-4-trifluoromethyl-pyrimidine-5-carboxylic acid (tetrahydro-pyran-4-ylmethyl)-amide;
2-(4-Fluoro-3-chloro-phenylamino)trifluoromethyl-pyrimidine-5-carboxylic acid (tetrahydro-pyran-4-ylmethyl)-amide;
2-(4-Trifluoromethoxy-3-chloro-phenylamino)-4-trifluoromethyl-pyrimidine-5-carboxylic acid (tetrahydro-pyran-4-ylmethyl)-amide;
2-(4-Cyano-3-chloro-phenylamino)-4-trifluoromethyl-pyrimidine-5-carboxylic acid (tetrahydro-pyran-4-ylmethyl)-amide;
2-(4-Trifluoromethyl-3-fluoro-phenylamino)-4-trifluoromethyl-pyrimidine-5-carboxylic acid (tetrahydro-pyran-4-ylmethyl)-amide;
2-(4-Cyano-3-chloro-phenylamino)-4-trifluoromethyl-pyrimidine-5-carboxylic acid cyclopentylmethyl-amide;
2-(2,4-Dichloro-phenylamino)-4-trifluoromethyl-pyrimidine-5-carboxylic acid (1,1-dioxo-hexahydro-1l$^6$-thiopyran-4-yl)-amide;
2-(2,4-Difluoro-phenylamino)-4-trifluoromethyl-pyrimidine-5-carboxylic acid cyclohexylmethyl-amide;
2-(2-Chloro-4-fluoro-phenylamino)-4-trifluoromethyl-pyrimidine-5-carboxylic acid cyclohexylmethyl-amide;
2-(2,4-Difluoro-phenylamino)-4-trifluoromethyl-pyrimidine-5-carboxylic acid cyclobutylmethyl-amide;
2-(2-Chloro-4-fluoro-phenylamino)-4-trifluoromethyl-pyrimidine-5-carboxylic acid cyclobutylmethyl-amide;
2-(2-Chloro-4-bromo-phenylamino)-4-trifluoromethyl-pyrimidine-5-carboxylic acid cyclohexylmethyl-amide;
2-(2-Fluoro-4-chloro-phenylamino)-4-trifluoromethyl-pyrimidine-5-carboxylic acid cyclohexylmethyl-amide;
2-(2-Chloro-4-bromo-phenylamino)-4-trifluoromethyl-pyrimidine-5-carboxylic acid cyclobutylmethyl-amide;
2-(2-Fluoro-4-chloro-phenylamino)-trifluoromethyl-pyrimidine-5-carboxylic acid cyclobutylmethyl-amide;
2-(2-Fluoro-4-bromo-phenylamino)-4-trifluoromethyl-pyrimidine-5-carboxylic acid cyclobutylmethyl-amide;
2-(2-Bromo-4-chloro-phenylamino)-4-trifluoromethyl-pyrimidine-5-carboxylic acid cyclobutylmethyl-amide;
2-(2-Fluoro-4-bromo-phenylamino)-4-trifluoromethyl-pyrimidine-5-carboxylic acid cyclohexylmethyl-amide;
2-(2-Fluoro-4-bromo-phenylamino)-4-trifluoromethyl-pyrimidine-5-carboxylic acid (tetrahydro-pyran-4-ylmethyl)-amide;
2-(2-Chloro-4-fluoro-phenylamino)-4-trifluoromethyl-pyrimidine-5-carboxylic acid (tetrahydro-pyran-4-ylmethyl)-amide;
2-(2-Chloro-4-bromo-phenylamino)-4-trifluoromethyl-pyrimidine-5-carboxylic acid (tetrahydro-pyran-4-ylmethyl)-amide;
2-(2-Chloro-4-cyano-phenylamino)-4-trifluoromethyl-pyrimidine-5-carboxylic acid (tetrahydro-pyran-4-ylmethyl)-amide;
2-(2-Chloro-4-trifluoromethyl-phenylamino)-4-trifluoromethyl-pyrimidine-5-carboxylic acid (tetrahydro-pyran-4-ylmethyl)-amide;
2-(2-Chloro-4-cyano-phenylamino)-4-trifluoromethyl-pyrimidine-5-carboxylic acid cyclohexylmethyl-amide;
2-(2-Bromo-4-chloro-phenylamino)-4-trifluoromethyl-pyrimidine-5-carboxylic acid cyclohexylmethyl-amide;
2-(2-Bromo-4-chloro-phenylamino)-4-trifluoromethyl-pyrimidine-5-carboxylic acid (tetrahydro-pyran-4-ylmethyl)-amide;
2-(3-Bromophenylamino)-4-trifluoromethyl-pyrimidine-5-carboxylic acid cyclopropylmethyl-amide;
2-(2,4-Dichlorophenylamino)-4-trifluoromethyl-pyrimidine-5-carboxylic acid cyclopropylmethyl-amide;
2-(2,3-Difluorophenylamino)-4-trifluoromethyl-pyrimidine-5-carboxylic acid cyclohexylmethyl-amide;
2-(2-Fluoro-3-trifluoromethyl-phenylamino)-4-trifluoromethyl-pyrimidine-5-carboxylic acid cyclohexylmethyl-amide;
2-(2-Chloro-4-methylphenylamino)-4-trifluoromethyl-pyrimidine-5-carboxylic acid cyclohexylmethyl-amide;
2-(4-Chloro-3-methoxyphenylamino)-4-trifluoromethyl-pyrimidine-5-carboxylic acid cyclohexylmethyl-amide;
2-(5-Chloro-2-methylphenylamino)-4-trifluoromethyl-pyrimidine-5-carboxylic acid cyclohexylmethyl-amide;
2-(3-Chloro-4-fluoro-phenylamino)-4-trifluoromethyl-pyrimidine-5-carboxylic acid cyclopentylmethyl-amide;
2-(3-Chloro-2-fluoro-phenylamino)-4-trifluoromethyl-pyrimidine-5-carboxylic acid cyclopentylmethyl-amide;
2-(2-Chloro-5-fluoro-phenylamino)-4-trifluoromethyl-pyrimidine-5-carboxylic acid cyclopentylmethyl-amide;
2-(3,4-Dichlorophenylamino)-4-trifluoromethylpyrimidine-5-carboxylic acid (tetrahydro-pyran-4-ylmethyl)-amide;
2-(Phenylamino)-4-trifluoromethyl-pyrimidine-5-carboxylic acid cyclopentylmethyl-amide 2-(2-Fluoro-3-trifluoromethyl-phenylamino)-4-trifluoromethyl-pyrimidine-5-carboxylic acid cyclobutylmethyl-amide;
2-(2-Trifluoromethyl-4-bromo-phenylamino)-4-trifluoromethyl-pyrimidine-5-carboxylic acid (tetrahydro-pyran-4-ylmethyl)-amide;
2-(3-Chlorophenylamino)-4-trifluoromethyl-pyrimidine-5-carboxylic acid (tetrahydrothiopyran-4-ylmethyl)amide;

2-(2,4-Dichlorophenylamino)-4-trifluoromethyl-pyrimidine-5-carboxylic acid (tetrahydrothiopyran-4-ylmethyl)amide;

and pharmaceutically acceptable derivatives thereof.

Compounds of formula (I) can be prepared as set forth in the following schemes:

Scheme 1:

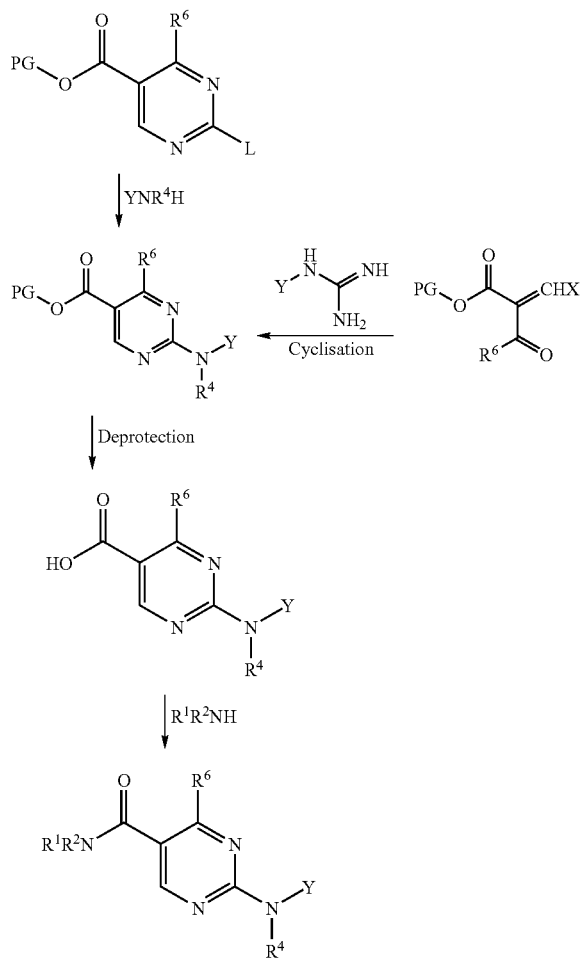

wherein L is a leaving group, for example halo, PG is a protecting group for example methyl, ethyl or benzyl, X is a leaving group for example halo, $OC_{1-6}$alkyl, e.g. O-methyl or O-ethyl or $NR^aR^b$ wherein $R^a$ and $R^b$ are independently selected from $C_{1-6}$alkyl, e.g. methyl, and $R^1$, $R^2$, $R^4$, $R^6$ and Y are as defined for compounds of formula (I).

Scheme 2:

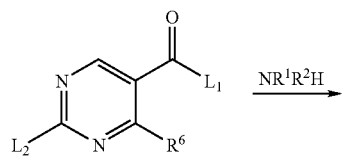

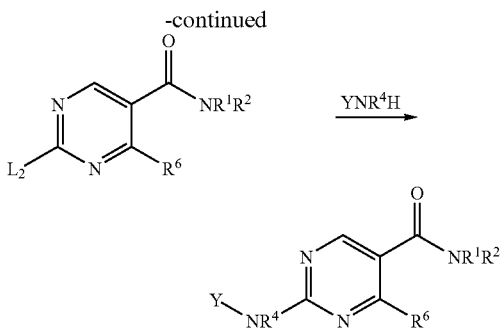

wherein $L_1$ and $L_2$ are leaving groups independently selected from halo, for example chloro, $R^1$, $R^2$, $R^4$, $R^6$ and Y are as defined for compounds of formula (I).

It is to be understood that the present invention encompasses all isomers of compounds of formula (I) and their pharmaceutically acceptable derivatives, including all geometric, tautomeric and optical forms, and mixtures thereof (e.g. racemic mixtures). Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses. The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent The compounds of formula (I) may be prepared in crystalline or noncrystalline form, and, if crystalline, may optionally be hydrated or solvated. This invention includes within its scope stoichiometric hydrates or solvates as well as compounds containing variable amounts of water and/or solvent.

The compounds of the invention bind selectively to the CB2 receptor, and are therefore useful in treating CB2 receptor mediated diseases.

In view of their ability to bind to the CB2 receptor, the compounds of the invention may be useful in the treatment of the disorders that follow. Thus, the compounds of formula (I) may be useful as analgesics. For example they may be useful in the treatment of chronic inflammatory pain (e.g. pain associated with rheumatoid arthritis, osteo-arthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention may also be useful disease modification or joint structure preservation in multiple sclerosis, rheumatoid arthritis, osteo-arthritis, rheumatoid spondylitis, gouty arthritis and juvenile arthritis.

The compounds of the invention may be particularly useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of fever.

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

The compounds of formula (I) are also useful in the treatment of immunological diseases such as autoimmune diseases, immunological deficiency diseases or organ transplantation. The compounds of formula (I) are also effective in increasing the latency of HIV infection.

The compounds of formula (I) are also useful in the treatment of diseases of abnormal platelet function (e.g. occlusive vascular diseases).

The compounds of formula (I) are also useful for the preparation of a drug with diuretic action.

The compounds of formula (I) are also useful in the treatment of impotence or erectile dysfunction.

The compounds of formula (I) are also useful for attenuating the hemodynamic side effects of non-steroidal anti-inflammatory drugs (NSAID's) and cyclooxygenase-2 (COX-2) inhibitors.

The compounds of formula (I) are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, motor neuron disease); vascular dementia (including multi-infarct dementia); as well as dementia associated with intracranial space occupying lesions; trauma; infections and related conditions (including HIV infection); dementia in Parkinson's disease; metabolism; toxins; anoxia and vitamin deficiency; and mild cognitive impairment associated with ageing, particularly Age Associated Memory Impairment. The compounds may also be useful for the treatment of amyotrophic lateral sclerosis (ALS) and neuroinflamation.

The compounds of formula (I) are also useful in neuroprotection and in the treatment of neurodegeneration following stroke, cardiac arrest, pulmonary bypass, traumatic brain injury, spinal cord injury or the like.

The compounds of formula (I) are also useful in the treatment of tinnitus.

The compounds of formula (I) are also useful in the treatment of psychiatric disease for example schizophrenia, depression (which term is used herein to include bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia for example of the Alzheimer's type, schizoaffective disorder or the depressed type, and depressive disorders resulting from general medical conditions including, but not limited to, myocardial infarction, diabetes, miscarriage or abortion, etc), anxiety disorders (including generalised anxiety disorder and social anxiety disorder), panic disorder, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. *cannabis*, heroin, morphine), amphetamine or amphetamine-related drugs (e.g. dextroamphetamine, methylamphetamine) or a combination thereof.

The compounds of formula (I) are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formula (I) are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

It is to be understood that references to treatment includes both treatment of established symptoms and prophylactic treatment unless explicitly stated otherwise.

According to a further aspect of the invention, we provide a compound of formula (I) or a pharmaceutically acceptable derivative thereof for use in human or veterinary medicine.

According to another aspect of the invention, we provide a compound of formula (I) or a pharmaceutically acceptable derivative thereof for use in the treatment of a condition which is mediated by the activity of cannabinoid 2 receptors.

According to a further aspect of the invention, we provide a method of treating a human or animal subject suffering from a condition which is mediated by the activity of cannabinoid 2 receptors which comprises administering to said subject a therapeutically effective amount of a compound of formula (I) or a pharmaceutically acceptable derivative thereof.

According to a further aspect of the invention we provide a method of treating a human or animal subject suffering from an immune disorder, an inflammatory disorder, pain, rheumatoid arthritis, multiple sclerosis, osteoarthritis or osteoporosis which method comprises administering to said subject an effective amount of a compound of formula (I) or a pharmaceutically acceptable derivative thereof. Preferably the pain is selected from inflammatory pain, viseral pain, cancer pain, neuropathic pain, lower back pain, muscular sceletal, post operative pain, acute pain and migraine. More preferably the inflammatory pain is pain associated with rheumatoid arthritis or osteoarthritis.

According to another aspect of the invention is provided the use of a compound of formula (I) or a pharmaceutically acceptable derivative thereof for the manufacture of a therapeutic agent for the treatment or prevention of a condition such as an immune disorder, an inflammatory disorder, pain, rheumatoid arthritis, multiple sclerosis, osteoarthritis or osteoporosis Preferably the pain is selected from inflammatory pain, viseral pain, cancer pain, neuropathic pain, lower back pain, muscular sceletal, post operative pain, acute pain and migraine. More preferably the inflammatory pain is pain associated with rheumatoid arthritis or osteoarthritis.

In order to use a compound of formula (I) or a pharmaceutically acceptable derivative thereof for the treatment of humans and other mammals it is normally formulated in accordance with standard pharmaceutical practice as a pharmaceutical composition. Therefore in another aspect of the invention is provided a pharmaceutical composition comprising a compound of formula (I) or a pharmaceutically acceptable derivative thereof adapted for use in human or veterinary medicine.

As used herein, "modulator" means both antagonist, full or partial agonist and inverse agonist. Inone embodiment of the present modulators are agonists.

The term "treatment" or "treating" as used herein includes the treatment of established disorders and also includes the prophylaxis thereof. The term "prophylaxis" is used herein to mean preventing symptoms in an already afflicted subject or preventing recurrance of symptoms in an afflicted subject and is not limited to complete prevention of an afflication.

Compounds of formula (I) and their pharmaceutically acceptable derivatives may be administered in a standard manner for the treatment of the indicated diseases, for example orally, parentarally, sub-lingually, dermally, intranasally, transdermally, rectally, via inhalation or via buccal administration.

Compositions of formula (I) and their pharmaceutically acceptable derivatives which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or derivative in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of formula (I) or a pharmaceutically acceptable derivative thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.01 mg/Kg to 500 mg/Kg for example 0.1 mg to 500 mg/Kg, and preferably from 0.01 mg to 100 mg/Kg for example 1 mg/Kg to 100 mg/Kg, and each dosage unit for parenteral administration contains suitably from 0.1 mg to 100 mg/Kg, of a compound of formula (I) or a pharmaceutically acceptable derivative thereof calculated as the free acid. Each dosage unit for intranasal administration contains suitably 1400 mg and preferably 10 to 200 mg per person. A topical formulation contains suitably 0.01 to 5.0% of a compound of formula (I).

The daily dosage regimen for oral administration is suitably about 0.01 mg/Kg to 40 mg/Kg, of a compound of formula (I) or a pharmaceutically acceptable derivative thereof calculated as the free acid. The daily dosage regimen for parenteral administration is suitably about 0.001 mg/Kg to 40 mg/Kg, of a compound of formula (I) or a pharmaceutically acceptable derivative thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

It may be advantageous to prepare the compounds of the present invention as nanoparticles. This may improve the oral bioavailability of the compounds. For the purposes of the present invention "nanoparticulate" is defined as solid particles with 50% of the particles having a particle size of less than 1 μl, more preferably less than 0.75 μm The particle size of the solid particles of compound (1) may be determined by laser diffraction. A suitable machine for determining particle size by laser diffraction is a Lecotrac laser particle size analyser, using an HELOS optical bench fitted with a QUIXEL dispersion unit.

Numerous processes for the synthesis of solid particles in nanoparticulate form are known. Typically these processes involve a milling process, preferably a wet milling process in the presence of a surface modifying agent that inhibits aggregation and/or crystal growth of the nanoparticles once created. Alternatively these processes may involve a precipitation process, preferably a process of precipitation in an aqueous medium from a solution of the drug in a non-aqueous solvent.

Accordingly, in a further aspect, the present invention provides a process for preparing compound (I) in nanoparticulate form as hereinbefore defined, which process comprises milling or precipitation.

Representative processes for the preparation of solid particles in nanoparticulate form are described in the patents and publications listed below.

U.S. Pat. No. 4,826,689 to Violanto & Fischer, U.S. Pat. No. 5,145,684 to Liversidge et al U.S. Pat. No. 5,298,262 to Na & Rajagopalan, U.S. Pat. No. 5,302,401 Liversidge et al U.S. Pat. No. 5,336,507 to Na & Rajagopalan, U.S. Pat. No. 5,340,564 to Illig & Sarpotdar U.S. Pat. No. 5,346,702 to Na Rajagopalan, U.S. Pat. No. 5,352,459 to Hollister et al U.S. Pat. No. 5,354,560 to Lovrecich, U.S. Pat. No. 5,384,124 to Courteille et al, U.S. Pat. No. 5,429,824 to June, U.S. Pat. No. 5,503,723 to Ruddy et al, U.S. Pat. No. 5,510,118 to Bosch et al, U.S. Pat. No. 5,518 to Bruno et al, U.S. Pat. No. 5,518,738 to Eickhoff et al, U.S. Pat. No. 5,534,270 to De Castro, U.S. Pat. No. 5,536,508 to Canal et al, U.S. Pat. No. 5,552,160 to Liversidge et al, U.S. Pat. No. 5,560,931 to Eickhoff et al, U.S. Pat. No. 5,560,932 to Bagchi et al, U.S. Pat. No. 5,565,188 to Wong et al, U.S. Pat. No. 5,571,536 to Eickhoff et al, U.S. Pat. No. 5,573,783 to Desieno & Stetsko, U.S. Pat. No. 5,580,579 to Ruddy et al, U.S. Pat. No. 5,585,108 to Ruddy et al, U.S. Pat. No. 5,587,143 to Wong, U.S. Pat. No. 5,591,456 to Franson et al, U.S. Pat. No. 5,622,938 to Wong, U.S. Pat. No. 5,662,883 to Bagchi et al, U.S. Pat. No. 5,665,331 to Bagchi et al, U.S. Pat. No. 5,718,919 to Ruddy et al, U.S. Pat. No. 5,747,001 to Wiedmann et al, WO93/25190, WO96/24336, WO 97/14407, WO 98/35666, WO 99/65469, WO 00/18374, WO 00/27369, WO 00/30615 and WO 01/41760.

Such processes may be readily adapted for the preparation of compound (1) in nanoparticulate form. Such processes form a further aspect of the invention.

The process of the present invention preferably uses a wet milling step carried out in a mill such as a dispersion mill in order to produce a nanoparticulate form of the compound. The present invention may be put into practice using a conventional wet milling technique, such as that described in Lachman et al., The Theory and Practice of Industrial Pharmacy, Chapter 2, "Milling" p. 45 (1986).

In a further refinement, WO02/00196 (SmithKline Beecham plc) describes a wet milling procedure using a mill in which at least some of the surfaces are made of nylon (polyamide) comprising one or more internal lubricants, for use in the preparation of solid particles of a drug substance in nanoparticulate form.

In another aspect the present invention provides a process for preparing compounds of the invention in nanoparticulate form comprising wet milling a suspension of compound in a mill having at least one chamber and agitation means, said chamber(s) and/or said agitation means comprising a lubricated nylon, as described in WO02/00196.

The suspension of a compound of the invention for use in the wet milling is typically a liquid suspension of the coarse compound in a liquid medium. By "suspension" is meant that the compound is essentially insoluble in the liquid medium. Representative liquid media include an aqueous medium. Using the process of the present invention the average particle size of coarse compound of the invention may be up to 1 mm in diameter. This advantageously avoids the need to pre-process the compound.

In a further aspect of the invention the aqueous medium to be subjected to the milling comprises compound (1) present in from about 1% to about 40% w/w, preferably from about 10% to about 30% w/w, more preferably about 20% w/w.

The aqueous medium may further comprise one or more pharmaceutically acceptable water-soluble carriers which are suitable for steric stabilisation and the subsequent processing of compound (I) after milling to a pharmaceutical composition, e.g. by spray drying. Pharmaceutically acceptable excipients most suitable for steric stabilisation and spray-drying are surfactants such as poloxamers, sodium lauryl sulphate and polysorbates etc; stabilisers such as celluloses e.g. hydroxypropylmethyl cellulose; and carriers such as carbohydrates e.g. mannitol.

In a further aspect of the invention the aqueous medium to be subjected to the milling may further comprise hydroxypropylmethyl cellulose (HPMC) present from about 0.1 to about 10% w/w.

The process of the present invention may comprise the subsequent step of drying compound of the invention to yield a powder.

Accordingly, in a further aspect, the present invention provides a process for preparing a pharmaceutical composition contain a compound of the present invention which process comprises producing compound of formula (I) in nanoparticulate form optionally followed by drying to yield a powder.

A further aspect of the invention is a pharmaceutical composition comprising a compound of formula (I) or a pharmaceutically acceptable deriviate thereof in which the compound of formula (I) or a pharmaceutically acceptable deriviate thereof is present in solid particles in nanoparticulate form, in admixture with one or more pharmaceutically acceptable carriers or excipients.

By "drying" is meant the removal of any water or other liquid vehicle used during the process to keep compound of formula (I) in liquid suspension or solution. This drying step may be any process for drying known in the art, including freeze drying, spray granulation or spray drying. Of these methods spray drying is particularly preferred. All of these techniques are well known in the art. Spray drying/fluid bed granulation of milled compositions is carried out most suitably using a spray dryer such as a Mobile Minor Spray Dryer [Niro, Denmark], or a fluid bed drier, such as those manufactured by Glatt, Germany.

In a further aspect the invention provides a pharmaceutical composition as hereinbefore defined, in the form of a dried powder, obtainable by wet milling solid particles of compound of formaula (I) followed by spray-drying the resultant suspension.

Preferably, the pharmaceutical composition as hereinbefore defined, further comprises HPMC present in less than 15% w/w, preferably in the range 0.1 to 10% w/w.

The $CB_2$ receptor compounds for use in the instant invention may be used in combination with other therapeutic agents, for example COX-2 inhibitors, such as celecoxib, deracoxib, rofecoxib, valdecoxib, parecoxib or COX-189; 5-lipoxygenase inhibitors; NSAID's, such as aspirin, diclofenac, indomethacin, nabumetone or ibuprofen; leukotriene receptor antagonists; DMARD's such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands, $EP_4$ receptor ligands; $EP_2$ receptor ligands; $EP_3$ receptor ligands; $EP_4$ antagonists; $EP_2$ antagonists and $EP_3$ antagonists; bradykinin receptor ligands and vanilloid receptor ligand, antirheumatoid arthritis drugs, for example anti TNF drugs e.g. enbrel, remicade, anti-IL-1 drugs, or DMARDS e.g. leflunamide. When the compounds are used in combination with other therapeutic agents, the compounds may be administered either sequentially or simultaneously by any convenient route.

Additional COX-2 inhibitors are disclosed in U.S. Pat. Nos. 5,474,995 5,633,272; 5,466,823, 6,310,099 and 6,291,523; and in WO 96/25405, WO 97/38986, WO 98/03484, WO 97/14691, WO99/12930, WO00/26216, WO00/52008, WO00/38311, WO01/58881 and WO02/18374.

The compound of the present invention may be administered in combination with other active substances such as 5HT3 antagonists, NK-1 antagonists, serotonin agonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compound of the inventions include for example ondansetron, granisetron, metoclopramide.

Suitable serotonin agonists which may be used in combination with the compound of the invention include sumatriptan, rauwolscine, yohimbine, metoclopramide.

Suitable SSRIs which may be used in combination with the compound of the invention include fluoxetine, citalopram, femoxetine, fluvoxamine, paroxetine, indalpine, sertraline, zimeldine.

Suitable SNRIs which may be used in combination with the compound of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and amineptine.

It will be appreciated that the compounds of any of the above combinations or compositions may be administered simultaneously (either in the same or different pharmaceutical formulations), separately or sequentially.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

Determination of Cannabinoid CB1 Receptor Agonist Activity

The cannabinoid CB1 receptor agonist activity of the compounds of formula (I) was determined in accordance with the following experimental method.

Experimental Method

Yeast (*Saccharomyces cerevisiae*) cells expressing the human cannabinoid CB1 receptor were generated by integration of an expression cassette into the ura3 chromosomal locus of yeast strain MMY23. This cassette consisted of DNA sequence encoding the human CB1 receptor flanked by the yeast GPD promoter to the 5' end of CB1 and a yeast transcriptional terminator sequence to the 3' end of CB1. MMY23 expresses a yeast/mammalian chimeric G-protein alpha subunit in which the C-terminal 5 amino acids of Gpa1 are replaced with the C-terminal 5 amino acids of human Gαi3 (as described in Brown et al. (2000), Yeast 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 $OD_{600}$/ml).

Agonists were prepared as 10 mM stocks in DMSO. $EC_{50}$ values (the concentration required to produce 50% maximal response) were estimated using dilutions of between 3- and 5-fold (BiomekEX, Beckman) into DMSO. Agonist solutions in DMSO (1% final assay volume) were transferred into black, clear bottom, microtitre plates from NUNC (96- or 384-well). Cells were suspended at a density of 0.2 $OD_{600}$/ml in SC media lacking histidine, uracil, tryptophan, adenine and leucine and supplemented with 10 mM 3-aminotriazole, 0.1M sodium phosphate pH 7.0, and 20 µM fluorescein di-β-D-glucopyranoside (FDGlu). This mixture (50 ul per well for 384-well plates, 200 ul per well for 96-well plates) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a Spectrofluor microtitre plate reader (Tecan; excitation wavelength: 485 nm; emission wavelength: 535 nm). Fluorescence was plotted against compound concentration and iteratively curve fitted using a four parameter fit to generate a concentration effect value. Efficacy ($E_{Max}$) was calculated from the equation $$E_{max} = Max_{[compound\ X]} - Min_{[compound\ X]}/Max_{[HU210]} - Min_{[HU210]} \times 100\%$$

where $Max_{[compound\ X]}$ and $Min_{[compound\ X]}$ are the fitted maximum and minimum respectively from the concentration effect curve for compound X, and $Max_{[HU210]}$ and $Min_{[HU210]}$ are the fitted maximum and minimum respectively from the concentration effect curve for (6aR,10aR)-3-(1,1'-Dimethylheptyl)-6a,7,10,10a-tetrahydro-1-hydroxy-6,6-dimethyl-6H-dibenzo[b,d]pyran-9-methanol (HU210; available from Tocris). Equieffective molar ratio (EMR) values were calculated from the equation $$EMR = EC_{50\ [compound\ X]}/EC_{50\ [HU210]}$$

Where $EC_{50\ [compound\ X]}$ is the $EC_{50}$ of compound X and $EC_{50\ [HU210]}$ is the $EC_{50}$ of HU210.

Compounds of the Examples tested according to this method had $EC_{50}$ values>2000 nM and/or efficacy values of <50% at the cloned human cannabinoid CB1 receptor.

Determination of Cannabinoid CB2 Receptor Agonist Activity

The cannabinoid CB2 receptor agonist activity of the compounds of formula (I) was determined in accordance with the following experimental method.

Experimental Method

Yeast (*Saccharomyces cerevisiae*) cells expressing the human cannabinoid CB2 receptor were generated by integration of an expression cassette into the ura3 chromosomal locus of yeast strain MMY23. This cassette consisted of DNA sequence encoding the human CB2 receptor flanked by the yeast GPD promoter to the 5' end of CB2 and a yeast transcriptional terminator sequence to the 3' end of CB2. MMY23 expresses a yeast/mammalian chimeric G-protein alpha subunit in which the C-terminal 5 amino acids of Gpa1 are replaced with the C-terminal 5 amino acids of human Gαi3 (as described in Brown et al. (2000), Yeast 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 $OD_{600}$ ml).

Agonists were prepared as 10 mM stocks in DMSO. $EC_{50}$ values (the concentration required to produce 50% maximal response) were estimated using dilutions of between 3- and 5-fold (Biomek:FX, Beckman) into DMSO. Agonist solutions in DMSO (1% final assay volume) were transferred into black, clear bottom, microtitre plates from NUNC (96- or 384-well). Cells were suspended at a density of 0.2 $OD_{600}$/ml in SC media lacking histidine, uracil, tryptophan, adenine and leucine and supplemented with 10 mM 3-aminotriazole, 0.1M sodium phosphate pH 7.0, and 20M fluorescein di-β-D-glucopyranoside (FDGlu). This mixture (50 ul per well for 384-well plates, 200 ul per well for 96-well plates) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a Spectrofluor microtitre plate reader Tecan; excitation wavelength: 485 nm; emission wavelength: 535 nm). Fluorescence was plotted against compound concentration and iteratively curve fitted using a four parameter fit to generate a concentration effect value. Efficacy ($E_{max}$) was calculated from the equation $$E_{max} = Max_{[compound\ X]} - Min_{[compound\ X]}/Max_{[HU210]} - Min_{[HU210]} \times 100\%$$

where $Max_{[compound\ X]}$ and $Min_{[compound\ X]}$ are the fitted maximum and minimum respectively from the concentration effect curve for compound X, and $Max_{[HU210]}$ and $Min_{[HU210]}$ are the fitted maximum and minimum respectively from the concentration effect curve for (6aR,10aR)-3-(1,1'-Dimethylheptyl)-6a,7,10,10a-tetrahydro-1-hydroxy-6,6-dimethyl-6H-dibenzo[b,d]pyran-9-methanol (HU210; available from Tocris). Equieffective molar ratio (EMR) values were calculated from the equation $$EMR = EC_{50\ [compound\ X]}/EC_{50\ [HU210]}$$

Where $EC_{50\ [compound\ X]}$ is the $EC_{50}$ of compound X and $EC_{50\ [HU210]}$ is the $EC_{50}$ of HU210.

Compounds of Examples 1 to 23, 31 to 56, 68, 163-256 tested according to this method had $EC_{50}$ values 20 to 300 nM and efficacy values of >50% at the cloned human cannabinoid CB2 receptor.

Compounds of Examples 24 to 30 and 73-113, and 257-259 tested according to this method had $EC_{50}$ values 300 to 1000 nM or efficacy values of >50% at the cloned human cannabinoid CB2 receptor.

Compounds of Examples 57-67, 69-72, 114-162, and 260-265 tested according to this method had $EC_{50}$ values>1000 nM or efficacy values of <50% at the cloned human cannabinoid CB2 receptor.

The following examples are illustrative, but not limiting of the embodiments of the present invention.

All NMR experimental data was recorded at 400 MHz.

Conditions, Hardware, and Software used for Mass-directed Autopurification

Hardware

Waters 600 gradient pump, Waters 2700 Sample Manager, Waters Reagent Manager, Micromass ZMD mass spectrometer, Gilson 202—fraction collector, Gilson Aspec—waste collector.

Software

Micromass Masslynx version 3.5

Column

The column used is typically a Supelco ABZ+ column whose dimensions are 10 mm internal diameter by 100 mm in length. The stationary phase particle size is 5 μm.

Solvents

A. Aqueous solvent=Water+0.1% Formic Acid
B. Organic solvent=MeCN: Water 95:5+0.05% Formic Acid
Make up solvent=MeOH: Water 80:20+50 mMol Ammonium Acetate
Needle rinse solvent=MeOH: Water: DMSO 80:10:10

Methods

Five methods are used depending on the analytical retention time of the compound of interest. They all have a flow rate of 20 ml/min and a 15-minute runtime, which comprises of a 10-minute gradient followed by a 5-minute column flush and re-equilibration step.

Method 1 MDP 1.5-2.2=0-30% B
Method 2 MDP 2.0-2.8=5-30% B
Method 3 MDP 2.5-3.0=15-55% B
Method 4 MDP 2.8-4.0=30-80% B
Method 5 MDP 3.8-5.5=50-90% B

REFERENCE EXAMPLE 1

2-(3 Chlorophenylamino)-4-trifluoromethylpyrimidine-5-carboxylic acid benzylamide (a). To a solution of benzyl 2-chloro-4-trifluoromethylpyrimidine-5-carboxylate (0.50 g, ex Maybridge) in 1,4-dioxan (5 ml) was added 3-chloroaniline (0.85 ml) and the solution stirred at room temperature for 15 h. 1,4-Dioxan was removed under reduced pressure and ethyl acetate (15 ml) added. The solution was washed sequentially with 2N hydrochloric acid (10 ml) and water (3×10 ml), dried (MgSO$_4$), evaporated and triturated with hexane to afford benzyl 2-(3-chlorophenylamino)-4-trifluoromethylpyrimidine-5-carboxylate (524 mg).

NMR (DMSO-d6) δ 5.35 (2H, s), 7.14 (1H, d), 7.35-7.45 (6H, m), 7.68 (1H, m), 7.98 (1H, s), 9.13 (1H, s), 10.95 (1H, s).

LC/MS, t=3.70 min, [MH$^+$] 408 and 410.

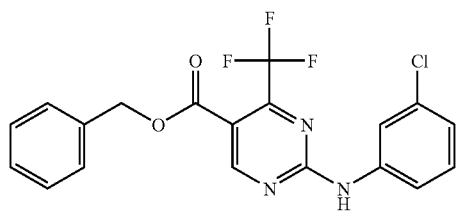

(b). To a solution of benzyl 2-(3-chlorophenylamino)-4-trifluoromethyl-pyrimidine-5-carboxylate (0.50 g) in ethanol (15 ml) was added a solution of potassium hydroxide (205 mg) in ethanol (10 ml) and the solution stirred at reflux for 15 h. Ethanol was removed under reduced pressure and water (15 ml) added. The solution was washed with ether and concentrated hydrochloric acid added to adjust the acidity to pH 1. The precipitated solid was filtered, washed with water and dried in vacuo at 50° C. to afford 2-(3-chlorophenylamino)-4-trifluoromethylpyrimidine-5-carboxylic acid (366 mg).

NMR (DMSO-d6) δ 7.49 (1H, d), 7.71 (1H, t), 7.98 (1H, d), 8.33 (1H, s), 9.42 (1H, s), 11.15 (1H, s), 14.0 (1H, br s).

LC/MS, t=3.44 min, [MH$^+$] 318 and 320.

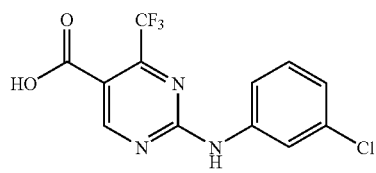

(c). To a solution of 2-(3-chlorophenylamino)-4-trifluoromethylpyrimidine-5-carboxylic acid (35 mg) in dimethylformamide (2 ml) was added successively N-ethylmorpholine (42 µl), benzylamine (15 µl), 1-hydroxybenzotriazole hydrate (23 mg) and 1-(3-dimethylamino-propyl)-3-ethylcarbodiimide hydrochloride (25 mg). The solution was stirred for 3 h and allowed to stand overnight. Dimethylformamide was removed under reduced pressure and ethyl acetate (5 ml) added. The solution was washed sequentially with 5% sodium bicarbonate solution (2.5 ml), water (2.5 ml), 5% citric acid solution (2.5 ml) and brine (2×2.5 ml), dried (MgSO$_4$) and evaporated to afford the title compound (45 mg).

NMR (DMSO-d6) δ 4.47 (2H, d), 7.10 (1H, d), 7.25 (1H, m), 7.36 (5H, m), 7.69 (1H, d), 7.98 (1H, s), 8.89 (1H, s), 9.12 (1H, t), 10.65 (1H, s).

LC/MS, t=3.23 min, [MH$^+$] 407 and 409.

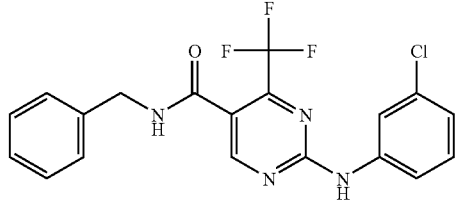

EXAMPLE 1

1-[2-(3-Chlorophenylamino)-4-trifluoromethyl pyrimidin-5-yl]-1-piperidin-1-ylmethanone

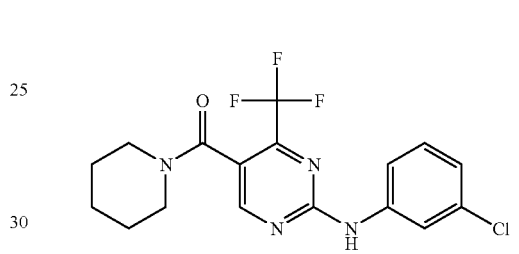

In a manner similar to Reference Example 1(c) 2-(3-chlorophenylamino)-4-trifluoromethylpyrimidine-5-carboxylic acid (35 mg) and piperidine (13 µl) afforded the title compound (38 mg).

NMR (DMSO-d6) δ 1.3-1.65 (6H, m), 3.28 (2H, s), 3.6 (2H, br s), 7.10 (1H, d), 7.37 (1H, t), 7.68 (1H, d), 7.96 (1H, s), 8.78 (1H, s), 10.55 (1H, s).

LC/MS, t=3.63 min, [MH$^+$] 385 and 387.

EXAMPLE 2

2-(3 Chlorophenylamino-4-trifluoromethylpyrimidine-5-carboxylic acid cyclopentylmethyl-amide

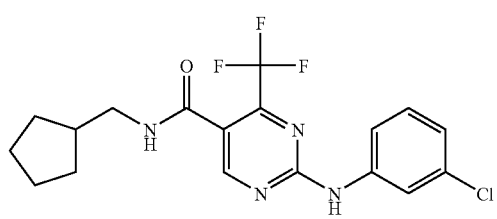

In a manner similar to Reference Example 1(c) 2-(3-chlorophenylamino)-4-trifluoromethyl-pyrimidine-5-carboxylic acid (100 mg) and cyclopentylmethylamine hydrochloride (63 mg, prepared as described in Kelley et al., J. Med. Chem., 40, 3207, (1997)) afforded the title compound (80 mg).

NMR (DMSO-d6) δ 1.20-1.26 (2H, m), 1.48-1.67 (4H, m), 1.67-1.73 (2H, m), 2.06-2.10 (1H, quintuplet), 3.15-3.18 (2H, t), 7.09 (1H, dt), 7.37 (1H, q), 7.67 (1H, d), 7.96 (1H, d), 8.60-8.63 (1H, t), 8.79 (1H, s), 10.60 (1H, s).

LC/MS, t=3.73 min, [MH$^+$] 399.

EXAMPLE 3

1-[2-(3-Chlorophenylamino)-4-trifluoromethylpyrimidin-5-yl]-1-morpholin-4-yl-methanone

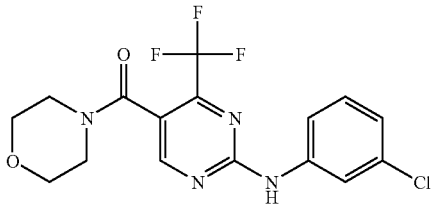

In a manner similar to Reference Example 1(c) 2-(3-chlorophenylamino)-4-trifluoromethylpyrimidine-5-carboxylic acid (35 mg) and morpholine (11.5 μl) afforded the title compound (43 mg).

NMR (DMSO-d6) δ 3.4-3.75 (8H, m), 7.10 (1H, d), 7.38 (1H, t), 7.68 (1H, d), 7.98 (1H, s), 8.80 (1H, s), 10.60 (1H, s).
LC/MS, t=3.29 min, [MH+] 387 and 389.

EXAMPLE 4

2-(3-Chlorophenylamino)-4-trifluoromethylpyrimidine-5-carboxylic acid cyclohexylmethylamide

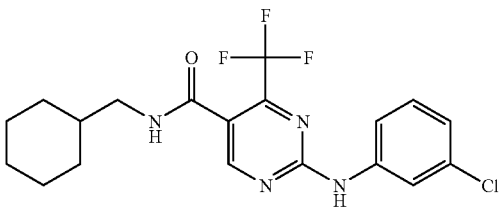

In a manner similar to Reference Example 1(c) 2-(3-chlorophenylamino)-4-trifluoromethylpyrimidine-5-carboxylic acid (35 mg) and cyclohexanemethylamine (15 mg) afforded the title compound (27 mg).

NMR (DMSO-d6) δ 0.85-1.0 (2H, m), 1.1-1.3 (3H, m), 1.5 (1H, m), 1.55-1.8 (5H, m), 3.06 (2H, t), 7.09 (1H, d), 7.37 (1H, t), 7.68 (1H, d), 7.97 (1H, s), 8.58 (1H, t), 8.79 (1H, s), 10.6 (1H, s).
LC/MS, t=3.87 min, [MH+] 413 and 415.

EXAMPLE 5

2-Phenylamino-4-trifluoromethylpyrimidine-5-carboxylic acid cyclohexyl-1-methyl-amide

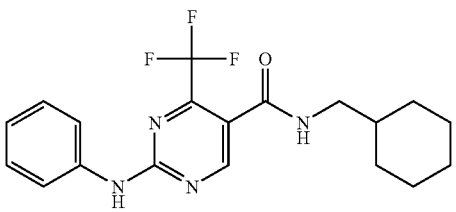

In a manner similar to Reference Example 1(c) 2-phenylamino-4-trifluoromethylpyrimidine-5-carboxylic acid (32 mg) and cyclohexanemethylamine (15 mg) afforded the title compound (33 mg).

NMR (DMSO-d6) δ 0.85-1.0 (2H, m), 1.05-1.3 (3H, m), 1.5 (1H, m), 1.55-1.8 (5H, m), 3.08 (2H, t), 7.06 (1H, d), 7.35 (2H, t), 7.76 (2H, d), 8.56 (1H, t), 8.74 (1H, s), 10.4 (1H, s).
LC/MS, t=3.66 min, [MH+] 379.

EXAMPLE 6

1-[2-(2,3-Dichlorophenylamino)-4-trifluoromethylpyrimidin-5-yl]-1-morpholin-4-yl-methanone

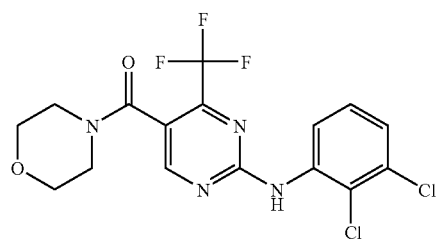

In a manner similar to Reference Example 1(c) 2-(2,3-dichlorophenylamino)-4-trifluoromethyl-pyrimidine-5-carboxylic acid (24 mg) and morpholine (10 μl) afforded the title compound (17 mg).

NMR (DMSO-d6) δ 3.4-3.8 (8H, m), 7.40 (1H, t), 7.54 (1H, d), 7.60 (1H, d), 8.78 (1H, s), 10.15 (1H, s).
LC/MS, t=3.32 min, [MH+] 421 and 423.

EXAMPLE 7

1-[2-(2,4-Dichlorophenylamino)-4-trifluoromethylpyrimidin-5-yl]-1-morpholin-4-yl-methanone

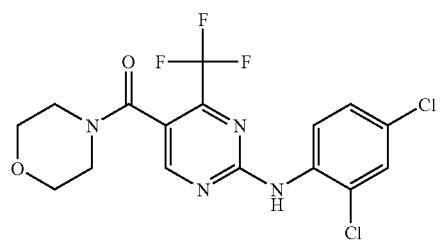

In a manner similar to Reference Example 1(c) 2-(2,4-dichlorophenylamino)-4-trifluoromethyl-pyrimidine-5-carboxylic acid (30 mg) and morpholine (10 μl) afforded the title compound (31 mg).

NMR (DMSO-d6) δ 3.3-3.8 (8H, m), 7.52 (1H, d of d), 7.68 (1H, d), 7.76 (1H, d), 8.73 (1H, s), 10.05 (1H, s).
LC/MS, t=3.37 min, [MH+] 421 and 423.

EXAMPLE 8

1-[2-(3,4-Dichlorophenylamino)-4-trifluoromethylpyrimidin-5-yl]-1-morpholin-4-yl-methanone

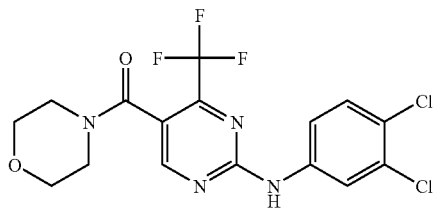

In a manner similar to Reference Example 1(c) 2-(3,4-dichlorophenylamino)-4-trifluoromethyl-pyrimidine-5-carboxylic acid (30 mg) and morpholine (10 μl) afforded the title compound (36 mg).

NMR (DMSO-d6) δ 3.35-3.8 (8H, m), 7.67 (1H, d), 7.76 (1H, d of d), 8.22 (1H, s), 8.90 (1H, s), 10.80 (1H, s).

LC/MS, t=3.45 min, [MH+] 421 and 423.

EXAMPLE 9

1-[2-(2,5-Dichlorophenylamino)-4-trifluoromethylpyrimidin-5-yl]-1-morpholin-1-4-yl-methanone

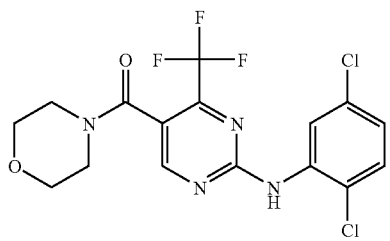

In a manner similar to Reference Example 1(c) 2-(2,5-dichlorophenylamino)-4-trifluoromethyl-pyrimidine-5-carboxylic acid (35 mg) and morpholine (14.5 μl) afforded the title compound (27 mg).

NMR (DMSO-d6) δ 3.4-3.75 (8H, m), 7.32 (1H, d of d), 7.66 (1H, d), 7.78 (1H, d), 8.71 (1H, s), 10.05 (1H, s).

LC/MS, t=3.31 min. [MH+] 421 and 423.

EXAMPLE 10

1-[2-(3-Fluorophenylamino)-4-trifluoromethylpyrimidin-5-yl]-1-morpholin-4-yl-methanone

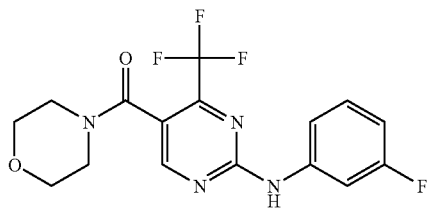

In a manner similar to Reference Example 1(c) 2-(3-fluorophenylamino)-4-trifluoromethylpyrimidine-5-carboxylic acid (35 mg) and morpholine (12 μl) afforded the title compound (31 mg).

NMR (DMSO-d6) δ 3.4-3.8 (8H, m), 6.85 (1H, t of d), 7.37 (1H, q), 7.52 (1H, d), 7.77 (1H, d of t), 8.80 (1H, s), 10.65 (1H, s).

LC/MS, t=3.06 min, [MH+] 371.

EXAMPLE 11

1-[2-(3-Bromophenylamino)-4-trifluoromethylpyrimidin-5-yl]-1-morpholin-4-yl-methanone

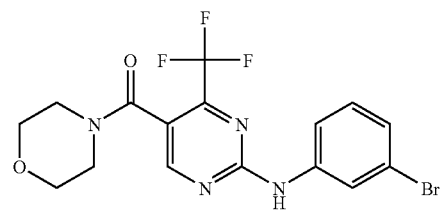

In a manner similar to Reference Example 1(c) 2-(3-bromophenylamino)-4-trifluoromethylpyrimidine-5-carboxylic acid (35 mg) and morpholine (10 μl) afforded the title compound (31 mg).

NMR (DMSO-d6) δ 3.4-3.8 (8H, m), 7.22 (1H, d), 7.30 (1H, t), 7.71 (1H, d), 8.11 (1H, s), 8.81 (1H, s), 10.60 (1H, s).

LC/MS, t=3.25 min, [MH+] 431 and 433.

EXAMPLE 12

1-[2-(3-Bromophenylamino)-4-trifluoromethylpyrimidin-5-yl]-1-piperidin-4-ylmethanone

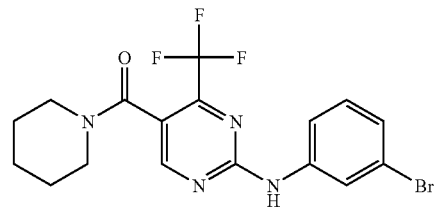

In a manner similar to Reference Example 1(c) 2-(3-bromophenylamino)-4-trifluoromethylpyrimidine-5-carboxylic acid (35 mg) and piperidine (12 μl) afforded the title compound (31 mg).

NMR (DMSO-d6) δ 1.3-1.7 (6H, m), 3.26 (2H, s), 3.60 (2H, br s), 7.21 (1H, d), 7.30 (1H, t), 7.70 (1H, d), 8.11 (1H, s), 8.78 (1H, s), 10.55 (1H, s).

LC/MS, t=3.57 min, [MH+] 429 and 431.

EXAMPLE 13

1-[2-(3,5-Dichlorophenylamino)-4-trifluoromethylpyrimidin-5-yl]-1-morpholin-4-yl-methanone

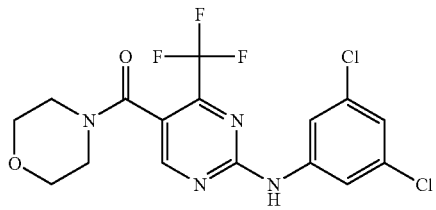

In a manner similar to Reference Example 1(c) 2-(3,5-dichlorophenylamino)-4-trifluoromethyl-pyrimidine-5-carboxylic acid (35 mg) and morpholine (14.5 µl) afforded the title compound (42 mg).

NMR (DMSO-d6) δ 3.4-3.75 (8H, m), 7.35 (1H, s), 7.89 (2H, s), 8.87 (1H, s), 10.80 (1H, s).

LC/MS, t=3.52 min, [MH$^+$] 421 and 423.

EXAMPLE 14

2-(3-Chlorophenylamino)-4-trifluoromethylpyrimidine-5-carboxylic acid cyclopentylamide

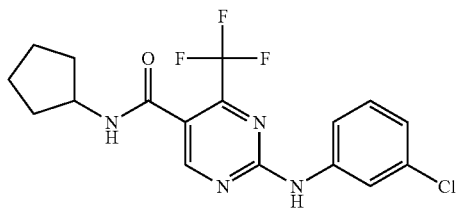

In a manner similar to Reference Example 1(c) 2-(3-chlorophenylamino)-4-trifluoromethylpyrimidine-5-carboxylic acid (35 mg) and cyclopentylamine (13 µl) afforded the title compound (34 mg).

NMR (DMSO-d6) δ 1.5 (4H, m), 1.65 (2H, m), 1.85 (2H, m), 4.15 (1H, m), 7.09 (1H, d), 7.36 (1H, t), 7.67 (1H, d), 7.97 (1H, s), 8.55 (1H, d), 8.79 (1H, s), 10.60 (1H, s).

LC/MS, t=3.55 min, [MH$^+$] 385 and 387.

EXAMPLE 15

2-(2,3-Dichlorophenylamino)-4-trifluoromethylpyrimidine-5-carboxylic acid cyclohexylmethyl-amide

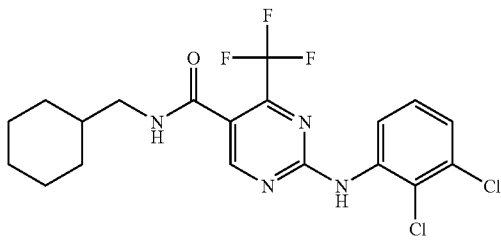

In a manner similar to Reference Example 1(c) 2-(2,3-dichlorophenylamino)-4-trifluoromethyl-pyrimidine-5-carboxylic acid (35 mg) and cyclohexanemethylamine (16 µl) afforded the title compound (30 mg).

NMR (DMSO-d6) δ 0.85-1.0 (2H, m), 1.1-1.3 (3H, m), 1.45 (1H, m), 1.55-1.8 (5H, m), 3.05 (2H, t), 7.40 (1H, t), 7.55 (2H, d), 8.53 (1H, t), 8.65 (1H, s), 10.15 (1H, s).

LC/MS, t=3.84 min, [MH$^+$] 447 and 449.

EXAMPLE 16

2-(2,4-Dichlorophenylamino)-4-triflouromethylpyrimidine-5-carboxylic acid cyclohexylmethyl-amide

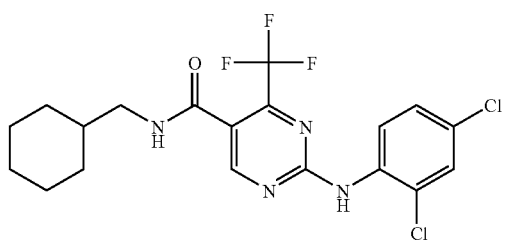

In a manner similar to Reference Example 1(c) 2-(2,4-dichlorophenylamino)-4-trifluoromethyl-pyrimidine-5-carboxylic acid (35 mg) and cyclohexanemethylamine (16 µl) afforded the title compound (14 mg).

NMR (DMSO-d6) δ 0.85-1.0 (2H, m), 1.1-1.3 (3H, m), 1.45 (1H, m), 1.55-1.75 (5H, m), 3.05 (2H, t), 7.46 (1H, d), 7.57 (1H, d), 7.72 (1H, s), 8.53 (1H, t), 8.64 (1H, s), 10.00 (1H, s).

LC/MS, t=3.90 min, [MH$^+$] 447 and 449.

EXAMPLE 17

2-(3,4-Dichlorophenylamino-4-trifluoromethylpyrimidine-5-carboxylic acid cyclohexylmethyl-amide

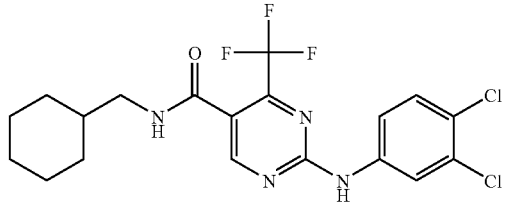

In a manner similar to Reference Example 1(c) 2-(3,4-dichlorophenylamino)-4-trifluoromethyl-pyrimidine-5-carboxylic acid (35 mg) and cyclohexanemethylamine (16 µl) afforded the title compound (31 mg).

NMR (DMSO-d6) δ 0.8-1.0 (2H, m), 1.1-1.3 (3H, m), 1.5 (1H, m), 1.55-1.8 (5H, m), 3.06 (2H, t), 7.62 (1H, d), 7.69 (1H, d), 8.18 (1H, s), 8.59 (1H, t), 8.82 (1H, s), 10.70 (1H, s).

LC/MS, t=4.01 min, [MH$^+$] 447 and 449.

EXAMPLE 18

2-(3,5-Dichlorophenylamino)-4-trifluoromethylpyrimidine-5-carboxylic acid cyclohexylmethyl-amide

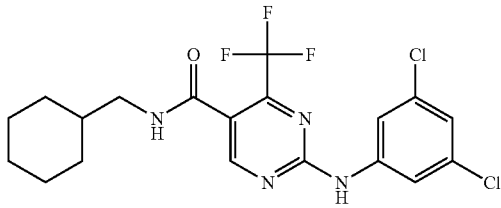

In a manner similar to Reference Example 1(c) 2-(3,5-dichlorophenylamino)-4-trifluoromethyl-pyrimidine-5-carboxylic acid (35 mg) and cyclohexanemethylamine (16 μl) afforded the title compound (30 mg).

NMR (DMSO-d6) δ 0.85-1.0 (2H, m), 1.1-1.3 (3H, m), 1.5 (1H, m), 1.55-1.8 (5H, m), 3.07 (2H, t), 726 (1H, s), 7.89 (2H, s), 8.58 (1H, t), 8.86 (1H, s), 10.80 (1H, s).

LC/MS, t=4.08 min [MH$^+$] 447 and 449.

EXAMPLE 19

2-(3-Fluorophenylamino)-4-trifluoromethylpyrimidine-5-arboxylic acid cyclohexylmethyl-amide

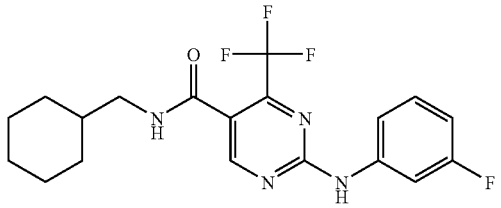

In a manner similar to Reference Example 1(c) 2-(3-fluorophenylamino)-4-trifluoromethyl-pyrimidine-5-carboxylic acid (35 mg) and cyclohexanemethylamine (18 μl) afforded the title compound (38 mg).

NMR (DMSO-d6) δ 0.85-1.0 (2H, m), 1.1-1.3 (3H, m), 1.5 (1H, m), 1.55-1.8 (5H, m), 3.09 (2H, t), 6.87 (1H, t of d), 7.39 (1H, q), 7.53 (1H, d), 7.78 (1H, d of t), 8.59 (1H, t), 8.80 (1H, s), 10.60 (1H, s).

LC/MS, t=3.68 min, [MH$^+$] 397.

EXAMPLE 20

2-(3-Bromophenylamino)-4-trifluoromethylpyrimidine-5-carboxylic acid cyclohexylmethyl-amide

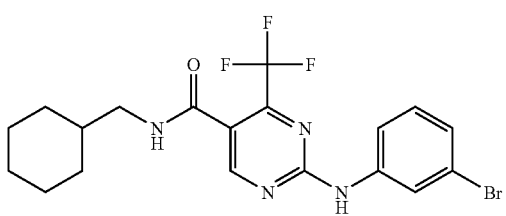

In a manner similar to Reference Example 1(c) 2-(3-bromophenylamino)-4-trifluoromethyl-pyrimidine-5-carboxylic acid (35 mg) and cyclohexanemethylamine (15 μl) afforded the title compound (36 mg).

NMR (DMSO-d6) δ 0.85-1.0 (2H, m), 1.1-1.3 (3H, m), 1.5 (1H, m), 1.55-1.8 (5H, m), 3.08 (2H, t), 7.23 (1H, d), 7.31 (1H, t), 7.71 (1H, d), 8.10 (1H, s), 8.57 (1H, t), 8.80 (1H, s), 10.60 (1H, s).

LC/MS, t=3.85 min, [MH$^+$] 457 and 459.

EXAMPLE 21

2-(2,6-Dichlorophenylamino)-4-trifluoromethylpyrimidine-5-carboxylic acid cyclohexylmethyl-amide

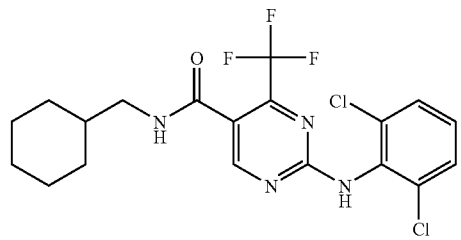

In a manner similar to Reference Example 1(c) 2-(2,6-dichlorophenylamino)-4-trifluoromethyl-pyrimidine-5-carboxylic acid (33 mg) and cyclohexanemethylamine (15 μl) afforded the title compound (9 mg).

NMR (DMSO-d6) δ 0.85-1.0 (2H, m), 1.05-1.25 (3H, m), 1.46 (1H, m), 1.55-1.8 (5H, m), 3.04 (2H, t), 7.39 (1H, t), 7.59 (2H, d), 8.56 (2H, m), 10.10 (1H, s).

LC/MS, t=3.84 min, [MH$^+$] 447 and 449.

EXAMPLE 22

2-(3-Chlorophenylamino)-4-trifluoromethylpyrimidine-5-carboxylic acid (tetrahydro-pyran-4-ylmethyl)-amide

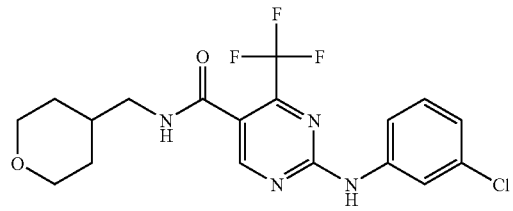

In a manner similar to Reference Example 1(c) 2-(3-chlorophenylamino)-4-trifluoromethyl-pyrimidine-5-carboxylic acid (30 mg) and 4-aminomethyltetrahydropyran (13 mg) afforded the title compound (25 mg).

NMR (DMSO-d6) δ 1.15-1.3 (2H, m), 1.62 (2H, d), 1.74 (1H, m), 3.13 (2H, t), 3.27 (2H, t), 3.86 (2H, d), 7.10 (1H, d), 7.37 (1H, t), 7.66 (1H, d), 7.97 (1H, s), 8.63 (1H, t), 8.82 (1H, s), 10.60 (1H, s).

LC/MS, t=3.22 min, [MH$^+$] 415 and 417.

EXAMPLE 23

2-(3-Chlorophenylamino)-4-trifluoromethylpyrimidine-5-carboxylic acid cyclobutyl-amide

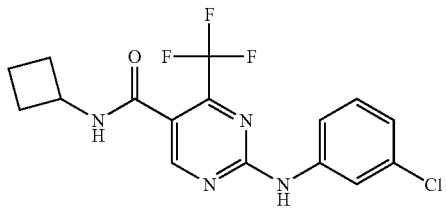

In a manner similar to Reference Example 1(c) 2-(3-chlorophenylamino)-4-trifluoromethyl-pyrimidine-5-carboxylic acid (35 mg) and cyclobutylamine (10 μl) afforded the title compound (28 mg).

NMR (DMSO-d6) δ 1.6-1.75 (2H, m), 1.9-2.05 (2H, m), 2.2-2.3 (2H, m), 4.32 (1H, m), 7.10 (1H, d), 7.37 (1H, t), 7.67 (1H, d), 7.96 (1H, s), 8.82 (2H, s), 10.60 (1H, s).
LC/MS, t=3.45 min, [MH$^+$] 371 and 373.

EXAMPLES 24 TO 30

Table 1) gives examples 24 to 30, column 1 gives the precursors that were reacted with methyl 2-chloro-4-trifluoromethyl-pyrimidine-5-carboxylate in a manner similar to that in Reference example 1(a). In a manner similar to that in Reference example 1(b), the carboxylic acid of the resultant ester was prepared. Finally, in a manner similar to that of Reference example 1(c), the resultant acid product was reacted with the precursor of column 2 to provide the final product of column 3.

TABLE 1

| Ex | 1 | 2 | 3 - Product | Structure | LC/MS 1 Retention time (min) 2 MH$^+$ 3 Formula |
|---|---|---|---|---|---|
| 24 | Aniline | Piperidine | 1-(2-Phenylamino-4-trifluoromethyl-pyrimidin-5-yl)-1-piperidin-1-yl-methanone | 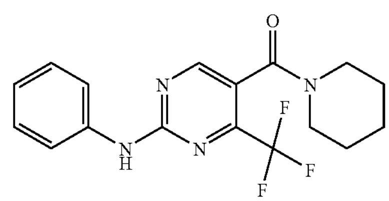 | 3.38 351 $C_{17}H_{17}F_3N_4O$ |
| 25 | Aniline | Morpholine | 1-Morpholin-4-yl-1-(2-phenylamino-4-trifluoromethyl-pyrimidin-5-yl)-methanone | 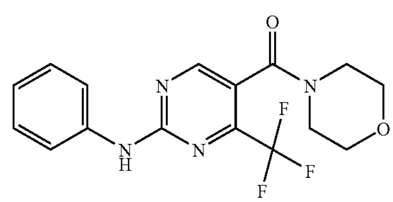 | 3.04 353 $C_{16}H_{15}F_3N_4O_2$ |
| 26 | 3-Chloroaniline | Aminoacetonitrile | 2-(3-Chloro-phenylamino)-4-trifluoromethyl-pyrimidine-5-carboxylic acid cyanomethyl-amide | 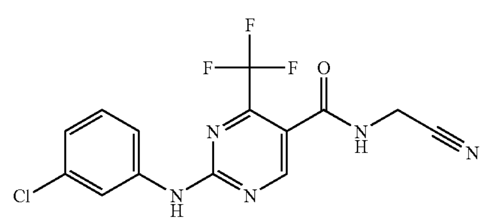 | 3.27 356 $C_{14}H_9{}^{35}ClF_3N_5O$ |
| 27 | 3-Chloroaniline | 3,3-Dimethylbutyl amine | 2-(3-Chloro-phenylamino)-4-trifluoromethyl-pyrimidine-5-carboxylic acid (3,3-dimethyl-butyl)-amide | 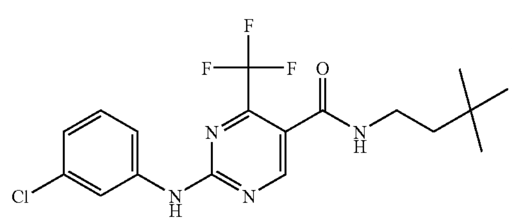 | 3.80 401 $C_{18}H_{20}{}^{35}ClF_3N_4O$ |

TABLE 1-continued

| Ex | 1 | 2 | 3 - Product | Structure | LC/MS 1 Retention time (min) 2 MH+ 3 Formula |
|---|---|---|---|---|---|
| 28 | 3-Chloroaniline | Neopentylamine | 2-(3-Chloro-phenylamino)-4-trifluoromethyl-pyrimidine-5-carboxylic acid (2,2-dimethyl-propyl)-amide | 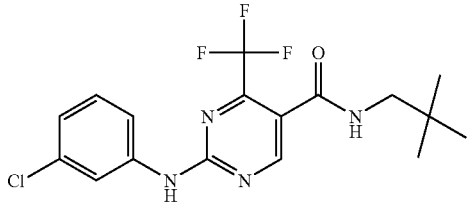 | 3.69<br>387<br>$C_{17}H_{18}{}^{35}ClF_3N_4O$ |
| 29 | 3-Fluoroaniline | Cyclobutylamine | 2-(3-Fluoro-phenylamino)-4-trifluoromethyl-pyrimidine-5-carboxylic acid cyclobutylamide | 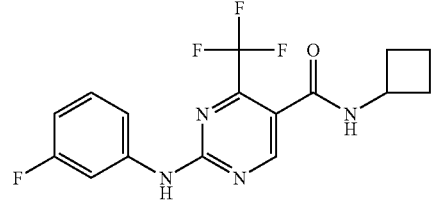 | 3.29<br>355<br>$C_{16}H_{14}F_4N_4O$ |
| 30 | 3,4-Dichloroaniline | Cyclobutylamine | 2-(3,4-Dichloro-phenylamino)-4-trifluoromethyl-pyrimidine-5-carboxylic acid cyclobutylamide | 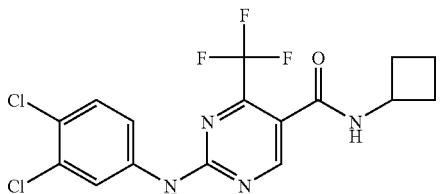 | 3.66<br>405<br>$C_{16}H_{13}{}^{35}Cl_2F_3N_4O$ |

EXAMPLE 31

2-(3-Fluorophenylamino)-4-trifluoromethylpyrimidine-5-carboxylic acid (tetrahydropyran-4-ylmethyl) amide

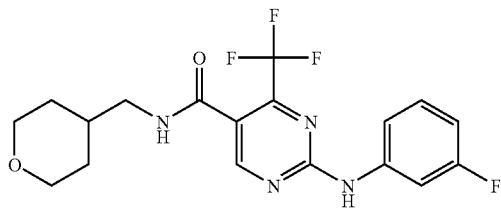

In a manner similar to Reference Example 1(c) 2-(3-fluorophenylamino)-4-trifluoromethyl-pyrimidine-5-carboxylic acid (35 mg) and 4-aminomethyltetrahydropyran (16 mg) afforded the title compound (38 mg).

NMR (DMSO-d6) δ 1.15-1.3 (2H, m), 1.63 (2H, d), 1.75 (1H, m), 3.15 (2H, t), 3.29 (2H, t), 3.86 (2H, d), 6.88 (1H, td), 7.38 (1H, q), 7.51 (1H,d), 7.76 (1H, dt), 8.64 (1H, t), 8.82 (1H, s), 10.60 (1H, s).

LC/MS, t=3.08 min, [MH+] 399.

EXAMPLE 32

2-(3-Bromophenylamino)-4-trifluoromethylpyrimidine-5-carboxylic acid (tetrahydropyran-4-ylmethyl) amide

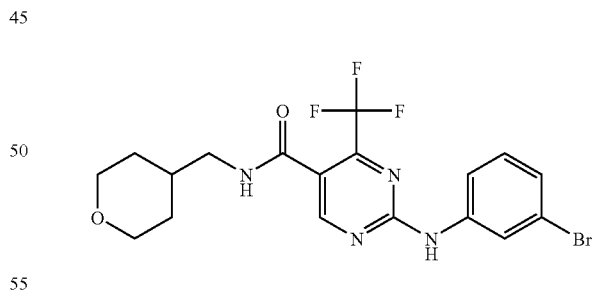

In a manner similar to Reference Example 1(c) 2-(3-bromophenylamino)-4-trifluoromethyl-pyrimidine-5-carboxylic acid (35 mg) and 4-aminomethyltetrahydropyran (13 5 mg) afforded the title compound (36 mg).

NMR (DMSO-d6) δ 1.15-1.3 (2H, m), 1.62 (2H, d), 1.74 (1H, m), 3.13 (2H, t), 3.27 (2H, t), 3.86 (2H, d), 7.23 (1H, d), 7.31 (1H, t), 7.71 (1H, d), 8.11 (1H, s), 8.63 (1H, t), 8.82 (1H, s), 10.60 (1H, s).

LC/MS, t=3.26 min, [MH+] 459 and 461.

EXAMPLE 33

2-(2,3-Dichlorophenylamino)-4-trifluoromethylpyrimidine-5-carboxylic acid (tetrahydropyran-4-ylmethyl)amide

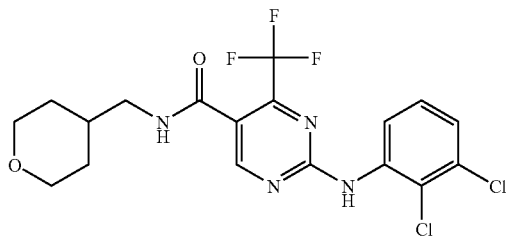

In a manner similar to Reference Example 1(c) 2-(2,3-dichlorophenylamino)-4-trifluoromethyl-pyrimidine-5-carboxylic acid (30 mg) and 4-aminomethyltetrahydropyran (12 mg) afforded the title compound (25 mg).

NMR (DMSO-d6) δ 1.1-1.25 (2H, m), 1.60 (2H, d), 1.72 (1H, m), 3.11 (2H, t), 3.26 (2H, t), 3.85 (2H, d), 7.40 (1H, t), 7.55 (2H, d), 8.60 (1H, t), 8.66 (1H, s), 10.10 (1H, s).

LC/MS, t=3.29 min, [MH$^+$] 449 and 451.

EXAMPLE 34

2-(2,4-Dichlorophenylamino)-4-trifluoromethylpyrimidine-5-carboxylic acid (tetrahydropyran-4-ylmethyl)-amide

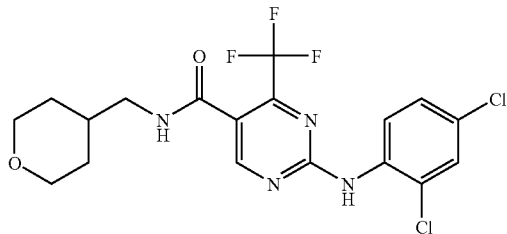

In a manner similar to Reference Example 1(c) 2-(2,4-dichlorophenylamino)-4-trifluoromethyl-pyrimidine-5-carboxylic acid (30 mg) and 4-aminomethyltetrahydropyran (12 mg) afforded the title compound (34 mg).

NMR (DMSO-d6) δ 1.1-1.25 (2H, m), 1.59 (2H, d), 1.72 (1H, m), 3.11 (2H, t), 3.26 (2H, t), 3.85 (2H, d), 7.47 (1H, dd), 7.57 (1H, d), 7.72 (1H, s), 8.60 (1H, t), 8.65 (1H, s), 10.05 (1H, s).

LC/MS, t=3.33 min, [MH$^+$] 449 and 451.

Additional Synthesis of Example 34

2-(2,4-Dichlorophenylamino)-4-trifluoromethyl-pyrimidine-5-carboxylic acid (tetrahydro-pyran-4-ylmethyl)-amide (a). To a solution of methyl 2-chloro-4-trifluoromethyl-pyrimidine-5-carboxylate (0.50 g, ex Maybridge) in 1,4-dioxan (5 ml) was added 2,4-dichloroaniline (1.7 g) and the solution stirred under reflux for 7 h. 1,4-Dioxan was removed under reduced pressure and ethyl acetate (15 ml) added. The solution was washed sequentially with 2N hydrochloric acid (10 ml) and water (3×10 ml), dried (MgSO$_4$), evaporated and triturated with hexane to afford methyl 2-(2,4-dichlorophenylamino)-4-trifluoromethylpyrimidine-5-carboxylate (358 mg).

NMR (CDCl$_3$) δ 3.95 (3H, s), 7.30 (1H, dd), 7.45 (1H, d), 8.00 (1H, s), 8.5 (1H, d), 9.05 (1H, s).

LC/MS, t=3.74 min, [MH$^+$]366.

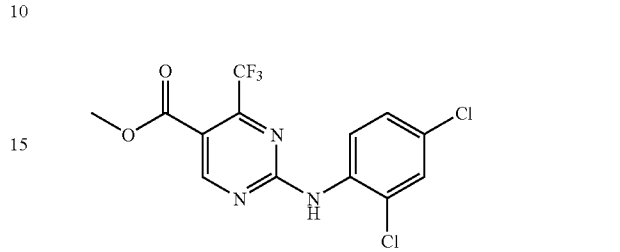

(b). To a solution of methyl 2-(2,4-dichlorophenylamino)-4-trifluoromethyl-pyrimidine-5-carboxylate (0.358 g) in ethanol (8 ml) was added a solution of potassium hydroxide (190 mg) in ethanol (8 ml) and the solution stirred at reflux for 24 h. Ethanol was removed under reduced pressure and water (15 ml) added. The solution was washed with ether and concentrated hydrochloric acid was added to adjust the acidity to pH 1. The precipitated solid was filtered, washed with water and dried in vacuo at 50° C. to afford 2-(2,4-dichlorophenylamino)-4-trifluoromethyl-pyrimidine-5-carboxylic acid (262 mg).

NMR (DMSO-d6) δ 7.48 (1H, dd), 7.60 (1H, d), 7.73 (1H, d), 8.95 (1H, s), 10.3 (1H, s), 13.6 (1H, s).

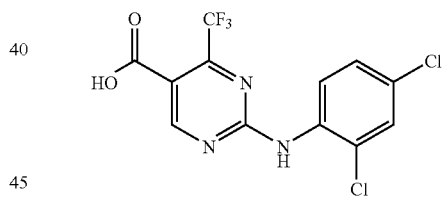

(c). To a solution of 2-(2,4-dichlorophenylamino)-4-trifluoromethyl-pyrimidine-5-carboxylic acid (30 mg) in dimethylformamide (2 ml) was added successively N-ethylmorpholine (33 μl), 4-aminomethyltetrahydropyran (12 mg), 1-hydroxybenzotriazole hydrate (18 mg) and 1-(3-dimethylamino-propyl)-3-ethylcarbodiimide hydrochloride (20 mg). The solution was stirred for 3 h and allowed to stand overnight. Dimethylformamide was removed under reduced pressure and ethyl acetate (5 ml) added. The solution was washed sequentially with 5% sodium bicarbonate solution (2.5 ml), water (2.5 ml), 5% citric acid solution (2.5 ml) and brine (2×2.5 ml), dried (MgSO$_4$) and evaporated to afford the title compound (34 mg) NMR (DMSO-d6) δ 1.20 (2H, m), 1.58 (2H, d), 1.70 (1H, m), 3.10 (2H, t), 3.23 (2H, t), 3.84 (2H, dd), 7.46 (1H, dd), 7.57 (1H, d), 7.71 (1H, d), 8.59 (1H, t), 8.63 (1H, s), 10.00 (1H, s).

LC/MS, t=3.33 min, [MH$^+$] 449.

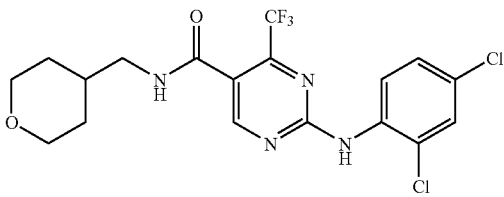

Additional Synthesis of Example 34

2-(2,4-Dichlorophenylamino)-4-trifluoromethyl-pyrimidine-5-carboxylic acid (tetrahydro-pyran-4-ylmethyl)-amide (a). To a solution of methyl 2-chloro-4-trifluoromethylpyrimidine-5-carboxylate (70 g, ex Maybridge 22 g, ex Fluorochem 48 g) in 1,4-dioxan (100 n–1) was added 2,4-dichloroaniline (142 g) and the solution stirred under reflux for 10.5 h. 1,4-Dioxan was partially removed (approx 50 ml) under reduced pressure and 2N HCl (800 ml) added. The mixture was stirred with overhead stirring for 3 h and the resulting solid filtered onto a sinter. The solid was washed with 2N HCl (2×300 ml) and water (4×400 ml) then dried over sodium hydroxide in vacuo at 50° C. to afford methyl 2-(2,4-dichlorophenylamino)-4-trifluoromethyl-pyrimidine-5-carboxylate. The solid contained approximately 5% 2,4-dichloroaniline.

NMR (DMSO-d6) δ 3.84 (3H, s), 7.47 (1H, dd), 7.49 (1H, d), 7.74 (1H, d), 8.96 (1H, s), 10.45 (1H, s).

LC/MS, t=3.66 min, [MH$^+$] 366.

(b). To a solution of methyl 2-(2,4-dichlorophenylamino)-4-trifluoromethyl-pyrimidine-5-carboxylate (107 g) in methanol (700 ml) was added a solution of potassium hydroxide (50 g) in methanol (700 ml) and the solution stirred at reflux for 24 h. Methanol was removed under reduced pressure and water (800 ml) added. The solution was washed with ether (3×400 ml, which removed the remaining 2,4-dichloroaniline) and concentrated hydrochloric acid added to adjust the acidity to pH 1. The precipitated solid was filtered, washed with 2N HCl and water until the pH of the filtrate was neutral. The solid was dried in vacuo at 50° C. to afford 2-(2,4-dichlorophenylamino)-4-trifluoromethyl-pyrimidine-5-carboxylic acid (86.9 g)

NMR (DMSO-d6) δ 7.48 (1H, dd), 7.60 (1H, d), 7.73 (1H, d), 8.95 (1H, s), 10.3 (1H, s), 13.6 (1H, s).

LC/MS, t=4.35 min, [MH$^+$] 352

(c). To a solution of 2-(2,4-dichlorophenylamino)-4-trifluoromethyl-pyrimidine-5-carboxylic acid (86 g) in dimethylformamide (800 ml) was added successively N-ethylmorpholine (93 ml), 4 aminomethyltetrahydropyran (29.5 g), 1-hydroxybenzotriazole hydrate (51.5 g) and 1-(3-dimethylamino-propyl)-3-ethylcarbodiimide hydrochloride (56.2 g). The solution was stirred for 24 h. Dimethylformamide was partially removed (approx 650 ml) under reduced pressure and 5% sodium bicarbonate solution added (3×500 ml, added portionwise to control the release of carbon dioxide). The mixture was stirred with overhead stirring for 3 h and the resulting solid filtered onto a sinter. The solid was washed with 5% sodium bicarbonate (4×400 ml) and water (3×400 ml) then dried over sodium hydroxide in vacuo at 50° C. to afford the title compound (109.1 g)

NMR (DMSO-d6) δ 1.20 (2H, m), 1.58 (2H, d), 1.70 (1H, m), 3.10 (2H, t), 3.23 (2H, t), 3.84 (2H, dd), 7.46 (1H, dd), 7.57 (1H, d), 7.71 (1H, d), 8.59 (1H, t), 8.63 (1H, s), 10.00 (1H, s).

LC/MS, t=3.41 min, [MH$^+$]449.

EXAMPLE 35

2-(2,5-Dichlorophenylamino)-4-trifluoromethylpyrimidine-5-carboxylic acid (tetrahydropyran-4-ylmethyl)-amide

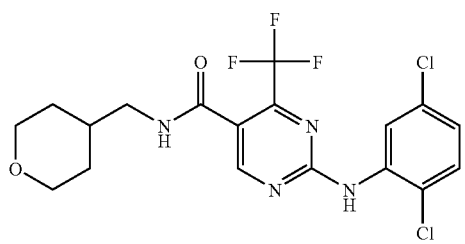

In a manner similar to Reference Example 1(c) 2-(2,5-dichlorophenylamino)-4-trifluoromethyl-pyrimidine-5-carboxylic acid (50 mg) and 4-aminomethyltetrahydropyran (25 mg) afforded the title compound (63 mg).

NMR (DMSO-d6) δ 1.15-1.3 (2H, m), 1.60 (2H, d), 1.72 (1H, m), 3.12 (2H, t), 3.27 (2H, t), 3.85 (2H, d), 7.35 (1H, dd), 7.59 (1H, d), 7.73 (1H, s), 8.62 (1H, t), 8.70 (1H, s), 10.05 (1H, s).

LC/MS, t=3.30 min, [MH$^+$] 449 and 451.

EXAMPLE 36

2-(3,5-Dichlorophenylamino)-4-trifluoromethylpyrimidine-5-carboxylic acid (tetrahydropyran-4-ylmethyl)-amide

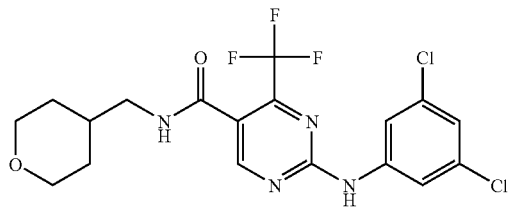

In a manner similar to Reference Example 1(c) 2-(3,5-Dichlorophenylamino)-4-trifluoromethyl-pyrimidine-5-carboxylic acid (50 mg) and 4-aminomethyltetrahydropyran (25 mg) afforded the title compound (68 mg).

NMR (DMSO-d6) δ 1.15-1.35 (2H, m), 1.62 (2H, d), 1.72 (1H, m), 3.14 (2H, t), 3.28 (2H, t), 3.86 (2H, d), 7.25 (1H, s), 7.88 (2H, s), 8.66 (1H, t), 8.88 (1H, s), 10.75 (1H, s).

EXAMPLE 37

2-(3-Methoxyphenylamino)-4-trifluoromethylpyrimidine-5-carboxylic acid (tetrahydropyran-4-ylmethyl)-amide

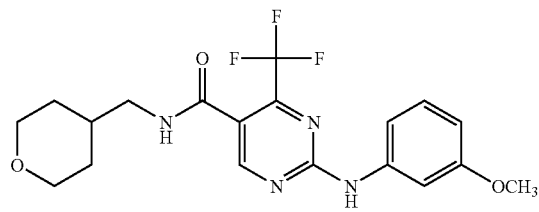

In a manner similar to Reference Example 1(c) 2-(3-methoxyphenylamino)-4-trifluoromethyl-pyrimidine-5-carboxylic acid (32 mg) and 4-aminomethyltetrahydropyran (14.5 mg) afforded the title compound (29 mg).

NMR (DMSO-d6) δ 1.1-1.25 (2H, m), 1.61 (2H, d), 1.74 (1H, m), 3.13 (2H, t), 3.27 (2H, t), 3.74 (3H, s), 3.86 (2H, d), 6.63 (1H, d), 7.25 (2H, m), 7.53 (1H, s), 8.62 (1H, t), 8.76 (1H, s), 10.35 (1H, s).

LC/MS, t=2.97 min, [MH+]411.

EXAMPLE 38

2-(3-Fluorophenylamino)-4-trifluoromethylpyrimidine-5-carboxylic acid cyclopentylmethyl-amide

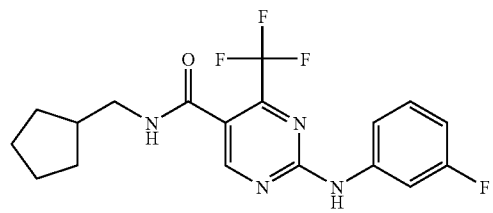

In a manner similar to Reference Example 1(c) 2-(3-fluorophenylamino)-4-trifluoromethyl-pyrimidine-5-carboxylic acid (30 mg) and cyclopentylmethylamine hydrochloride (17 mg, prepared as described in Kelley et al., J. Med. Chem., 40, 3207, (1997)) afforded the title compound (17 mg).

NMR (DMSO-d6) δ 1.20-1.30 (2H, m), 1.45-1.68 (4H, m), 1.68-1.77 (2H, m), 2.1 (1H, quintuplet), 3.19 (2H, t), 6.89 (1H, dt), 7.40 (1H, q), 7.54 (1H, d), 7.78 (1H, d), 8.64 (1H, t), 8.80 (1H, s), 10.70 (1H, s).

LC/MS, t=3.53 min, [MH+] 383.

EXAMPLE 39

2-(3-Bromophenylamino)-4-trifluoromethylpyrimidine-5-carboxylic acid cyclopentylmethyl-amide

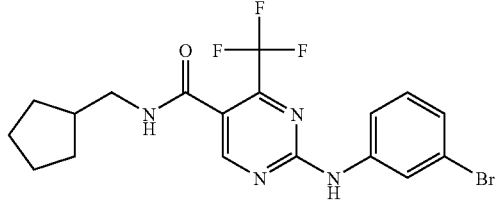

In a manner similar to Reference Example 1(c) 2-(3-bromophenylamino)-4-trifluoromethyl-pyrimidine-5-carboxylic acid (36.5 mg) and cyclopentylmethylamine hydrochloride (17 mg) afforded the title compound (28 mg).

NMR (DMSO-d6) δ 1.39-1.52 (2H, m), 1.69-1.90 (4H, m), 1.90-2.02 (2H, m), 2.34 (1H, quintuplet), 3.4 (2H, t), 7.48 (1H, d), 7.57 (1H, t), 7.95 (1H, d), 8.37 (1H, s). 8.86 (1H, t), 9.02 (1H, s), 10.80 (1H, s).

LC/MS, t=3.33 min, [MH+] 443 and 445.

EXAMPLE 40

2-(2,3-Dichlorophenylamino)-4-trifluoromethylpyrimidine-5-carboxylic acid cyclopentylmethyl-amide

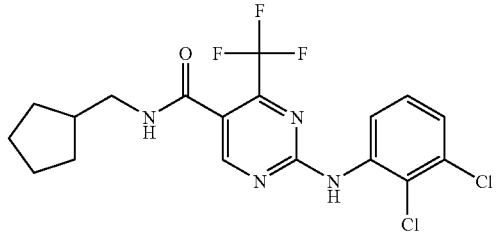

In a manner similar to Reference Example 1(c) 2-(2,3-dichlorophenylamino)-4-trifluoromethyl-pyrimidine-5-carboxylic acid (32 mg) and cyclopentylmethylamine hydrochloride (15 mg) afforded the title compound (30 mg).

NMR (DMSO-d6) δ 1.15-1.30 (2H, m), 1.44-1.78 (6H, m), 2.10 (1H, quintuplet), 3.16 (2H, t), 7.41 (2H, t), 7.54 (1H, m), 8.58 (1H, br t), 8.78 (1H, s), 10.10 (1H, s).

LC/MS, t=3.71 min, [MH+] 433 and 435.

EXAMPLE 41

2-(2,4-Dichlorophenylamino)-4-trifluoromethylpyrimidine-5-carboxylic acid cyclopentylmethyl-amide

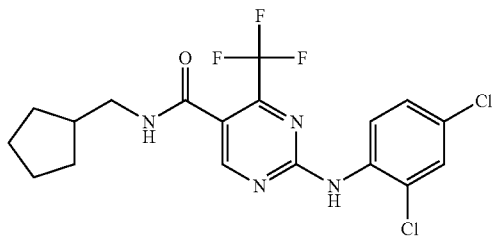

In a manner similar to Reference Example 1(c) 2-(2,4-dichlorophenylamino)-4-trifluoromethyl-pyrimidine-5-carboxylic acid (32 mg) and cyclopentylmethylamine hydrochloride (15 mg) afforded the title compound (27 mg).

NMR (DMSO-d6) δ 1.2-1.3 (2H, m), 1.4-1.79 (6H, m), 2.10 (1H, quintuplet), 3.17 (2H, t), 7.50 (1H, d), 7.60 (1H, d), 7.75 (1H, d), 8.68 (1H, t), 8.78 (1H, s), 10.10 (1H, s).

LC/MS, t=3.76 min, [MH$^+$] 433 and 435.

EXAMPLE 42

2-(2,5-Dichlorophenylamino)-4-trifluoromethylpyrimidine-5-carboxylic acid cyclopentylmethyl-amide

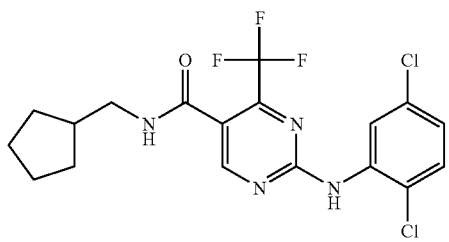

In a manner similar to Reference Example 1(c) 2-(2,5-dichlorophenylamino)-4-trifluoromethyl-pyrimidine-5-carboxylic acid (32 mg) and cyclopentylmethylamine hydrochloride (15 mg) afforded the title compound (23 mg).

NMR (DMSO-d6) δ 1.15-1.30 (2H, m), 1.45-1.79 (6H, m), 2.08 (1H, quintuplet), 3.18 (2H, t), 7.38 (1H, d), 7.62 (1H, d), 7.75 (1H, s), 8.61 (1H, br t), 8.71 (1H, s), 10.05 (1H, s).

LC/MS, t=3.76 min, [MH$^+$] 433 and 435.

EXAMPLE 43

2-(2,6-Dichlorophenylamino)-trifluoromethylpyrimidine-5-carboxylic acid cyclopentylmethyl-amide

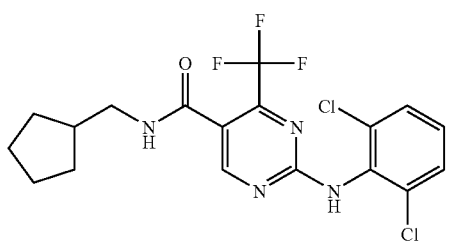

In a manner similar to Reference Example 1(c) 2-(2,6-dichlorophenylamino)-4-trifluoromethyl-pyrimidine-5-carboxylic acid (32 mg) and cyclopentylmethylamine hydrochloride (15 mg) afforded the title compound (25 mg).

NMR (DMSO-d6) δ 1.15-1.30 (2H, m), 1.45-1.78 (6H, m), 2.08 (1H, quintuplet), 3.15 (2H, t), 7.4 (1H, t), 7.6-7.68 (2H, m), 8.5-8.7 (2H, m), 10.20 (1H, s).

LC/MS, t=3.49 min, [MH$^+$] 433 and 435.

EXAMPLE 44

2-(3,4-Dichlorophenylamino)-4-trifluoromethylpyrimidine-5-carboxylic acid cyclopentylethyl-amide

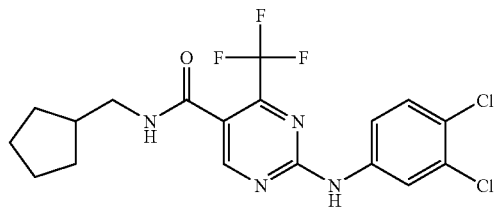

In a manner similar to Reference Example 1(c) 2-(3,4-dichlorophenylamino)-4-trifluoromethyl-pyrimidine-5-carboxylic acid (32 mg) and cyclopentylmethylamine hydrochloride (15 mg) afforded the title compound (29 mg).

NMR (DMSO-d6) δ 1.12-1.3 (2H, m), 1.44-1.8 (6H, m), 2.1 (1H, quintuplet). 3.17 (2H, t), 7.62 (1H, br d), 7.72 (1H, d), 8.18 (1H, d), 8.60-8.69 (1H, br t), 8.83 (1H, s), 10.80 (1H, s).

LC/MS, t=3.87 min, [MH$^+$] 433 and 435.

EXAMPLE 45

2-(3,5-Dichlorophenylamino)-4-trifluoromethylpyrimidine-5-carboxylic acid cyclopentylmethyl-amide

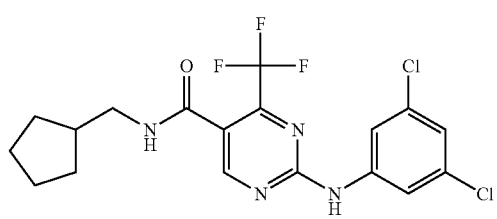

In a manner similar to Reference Example 1(c) 2-(3,5-dichlorophenylamino)-4-trifluoromethyl-pyrimidine-5-arboxylic acid (32 mg) and cyclopentylmethylamine hydrochloride (15 mg) afforded the title compound (27 mg).

NMR (DMSO-d6) 1.14-1.34 (2H, m), 1.45-1.8 (6H, m), 2.10 (1H, quintuplet), 3.20 (2H, t), 7.28 (1H, s), 7.91 (2H, s), 8.6-8.7 (1H, br t), 8.9 (1H, s), 10.75 (1H, s).

LC/MS, t=3.94 min, [MH$^+$] 433 and 435.

EXAMPLE 46

2-(3-Methoxyphenylamino)-4-trifluoromethylpyrimidine-5-carboxylic acid cyclopentylmethyl-amide

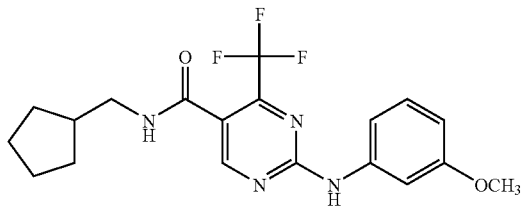

In a manner similar to Reference Example 1(c) 2-(3-methoxyphenylamino)-4-trifluoromethyl-pyrimidine-5-carboxylic acid (32 mg) and cyclopentylmethylamine hydrochloride (17 mg) afforded the title compound (21 mg).

NMR (DMSO-d6) 1.25-1.38 (2H, m), 1.50-1.85 (6H, m), 2.15 (1H, quintuplet), 3.25 (2H, t), 3.85 (3H, s), 6.70 (1H, br d), 7.26-7.37 (2H, m), 7.60 (1H, m), 8.68 (1H, t), 8.80 (1H, s), 10.50 (1H, s).

LC/MS, t=3.46 min, [MH$^+$] 395.

EXAMPLE 47

2-(3-Bromophenylamino)-4-trifluoromethylpyrimidine-5-carboxylic acid cyclobutylamide

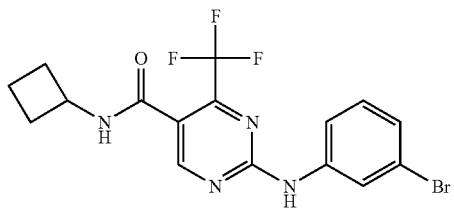

In a manner similar to Reference Example 1(c) 2-(3-bromophenylamino)-4-trifluoromethyl-pyrimidine-5-carboxylic acid (35 mg) and cyclobutylamine (10 μl) afforded the title compound (30 mg).

NMR (DMSO-d6) δ 1.70 (2H, m), 1.97 (2H, m), 2.22 (2H, m), 4.32 (1H, m), 7.22-7.33 (2H, m), 7.70 (1H, d), 8.10 (1H, s), 8.81-8.83 (2H, m), 10.60 (1H, s).

LC/MS, t=3.47 min, [MH$^+$] 415 and 417.

EXAMPLE 48

2-(2,3-Dichlorophenylamino)-4-trifluoromethylpyrimidine-5-carboxylic acid cyclobutylamide

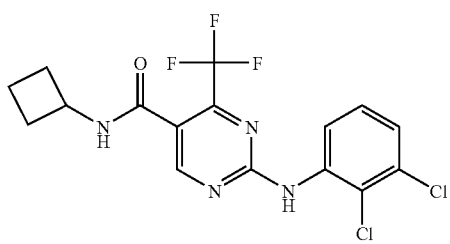

In a manner similar to Reference Example 1(c) 2-(2,3-Dichlorophenylamino)-4-trifluoromethyl-pyrimidine-5-carboxylic acid (25 mg) and cyclobutylamine (10 μl) afforded the title compound (20 mg).

NMR (DMSO-d6) δ 1.70 (2H, m), 1.97 (2H, m), 2.22 (2H, m), 4.32 (1H, m), 7.38-7.56 (3H, m), 8.65 (1H, s), 8.80 (1H, d), 10.10 (1H, s).

LC/MS, t=3.48 min, [MH$^+$] 405 and 407.

EXAMPLE 49

2-(2,4-Dichlorophenylamino)-4-trifluoromethylpyrimidine-5-carboxylic acid cyclobutylamide

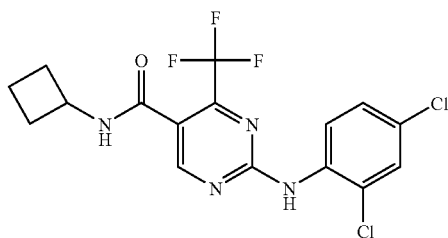

In a manner similar to Reference Example 1(c) 2-(2,4-dichlorophenylamino)-4-trifluoromethyl-pyrimidine-5-carboxylic acid (30 mg) and cyclobutylamine (10 μl) afforded the title compound (26 mg).

NMR (DMSO-d6) δ 1.70 (2H, m), 1.97 (2H, m), 2.22 (2H, m), 4.32 (1H, m), 7.46-7.72 (3H, m), 8.64 (1H, s), 8.80 (1H, d), 10.00 (1H, s).

LC/MS, t=3.54 min, [MH$^+$] 405 and 407.

EXAMPLE 50

2-(2,5-Dichlorophenylamino)-4-trifluoromethylpyrimidine-5-carboxylic acid cyclobutylamide

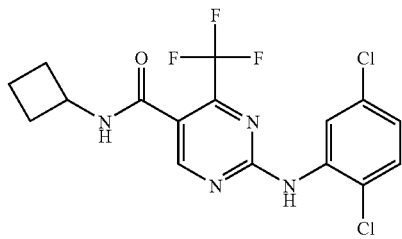

In a manner similar to Reference Example 1(c) 2-(2,5-dichlorophenylamino)-4-trifluoromethyl-pyrimidine-5-carboxylic acid (50 mg) and cyclobutylamine (19 μl)-afforded the title compound (56 mg).

NMR (DMSO-d6) δ 1.70 (2H, m), 1.97 (2H, m), 2.22 (2H, m), 4.30 (1H, m), 7.33-7.73 (3H, m), 8.70 (1H, s), 8.80 (1H, d), 10.00 (1H, s).

LC/MS, t=3.52 min, [MH$^+$] 405 and 407.

EXAMPLE 51

2-(2,6-Dichlorophenylamino)-4-trifluoromethylpyrimidine-5-carboxylic acid N-cyclobutylamide

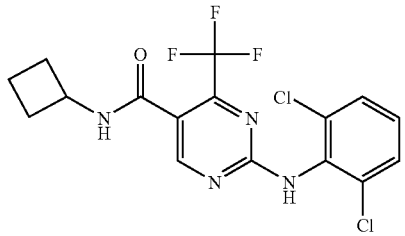

In a manner similar to Reference Example 1(c) 2-(2,6-dichlorophenylamino)-4-trifluoromethyl-pyrimidine-5-carboxylic acid (30 mg) and cyclobutylamine (10 μl) afforded the title compound (34 mg).

NMR (DMSO-d6) δ 1.70 (2H, m), 1.97 (2H, m), 2.22 (2H, m), 4.30 (1H, m), 7.36-7.60 (3H, m), 8.59 (1H, s), 8.80 (1H, d), 10.15 (1H, s).
LC/MS, t=3.24 min, [MH$^+$] 405 and 407.

EXAMPLE 52

2-(3,5-Dichlorophenylamino)-4-trifluoromethylpyrimidine-5-carboxylic acid cyclobutylamide

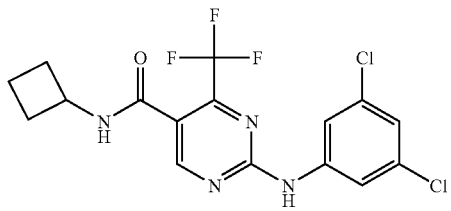

In a manner similar to Reference Example 1(c) 2-(3,5-dichlorophenylamino)-4-trifluoromethyl-pyrimidine-5-carboxylic acid (50 mg) and cyclobutylamine (19 μl) afforded the title compound (56 mg).

NMR (DMSO-d6) δ 1.70 (2H, m), 1.97 (2H, m), 2.22 (2H, m), 4.32 (1H, m), 7.25-7.87 (3H, m), 8.85 (1H, d), 8.88 (1H, s), 10.80 (1H, s).
LC/MS, t=3.73 min, [MH$^+$] 405 and 407.

EXAMPLE 53

2-(3-Methoxyphenylamino)-4-trifluoromethylpyrimidine-5-carboxylic acid cyclobutylamide

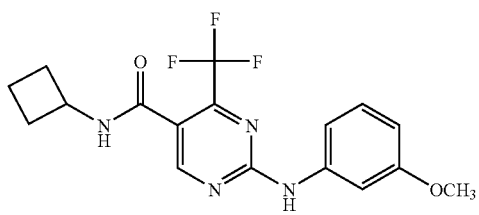

In a manner similar to Reference Example 1(c) 2-(3-methoxyphenylamino)-4-trifluoromethyl-pyrimidine-5-carboxylic acid (32 mg) and cyclobutylamine (10.5 μl) afforded the title compound (27 mg).

NMR (DMSO-d6) δ 1.70 (2H, m), 1.97 (2H, m), 2.22 (2H, m), 3.75 (3H, s), 4.32 (1H, m), 7.53-7.87 (4H, m), 8.76 (1H, s), 8.81 (1H, d), 10.40 (1H, s).
LC/MS, t=3.20 min, [MH$^+$] 367.

EXAMPLE 54

2-(3 Chlorophenylamino)-4-trifluoromethylpyrimidine-5-carboxylic acid cyclobutylmethyl-amide (a) A solution of borane-tetrahydrofuran complex (1M in tetrahydrofuran, 120 ml) was added over 10 min to a solution of cyclobutane carbonitrile (8.1 g) [Lancaster] in dry tetrahydrofuran (20 ml) under nitrogen at room temperature. The solution was refluxed overnight then cooled to 20°. Methanol (150 ml) was added dropwise over 15 mins keeping the temperature below 25°, then the mixture was cooled to 0° and dry hydrogen chloride was bubbled through for 30 min. The resulting mixture was refluxed for 90 min, evaporated and the residue re-evaporated twice from methanol. Ether (150 ml) was added and the resulting solid was filtered off. It was taken up in hot isopropanol (50 ml), filtered, and hot acetonitrile (30 ml) added. The mixture was cooled and the solid filtered off to give the C-cyclobutylmethylamine hydrochloride (5.7 g)

NMR (400 MHz, DMSO-d6) F6382 1.8 (4H, m), 2.0 (2H, m), 2.54 (1H, m), 2.80 (2H, d), 8.0 (3H, br s).

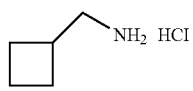

(b) In a manner similar to Reference Example 1(c) 2-(3-chlorophenylamino)-4-trifluoromethyl-pyrimidine-5-carboxylic acid (32 mg) and C-cyclobutylmethylamine hydrochloride (13 mg) afforded the title compound (28 mg).

NMR (DMSO-d6) δ 1.70 (2H, m), 1.82 (2H, m), 2.00 (2H, m), 2.50 (1H, m), 3.26 (2H, m), 7.08-7.95 (4H, m), 8.55 (1H, t), 8.77 (1H, s), 10.60 (1H, s).
LC/MS, t=3.56 min, [MH$^+$] 385.

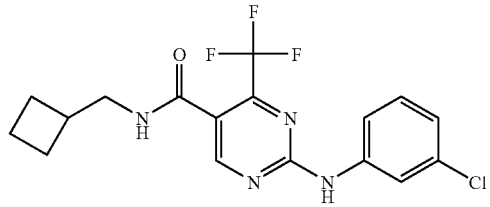

EXAMPLE 55

2-(2,6-Dichlorophenylamino)-4-trifluoromethyl-pyrimidine-5-carboxylic acid (tetrahydro-pyran-4-ylmethyl)-amide

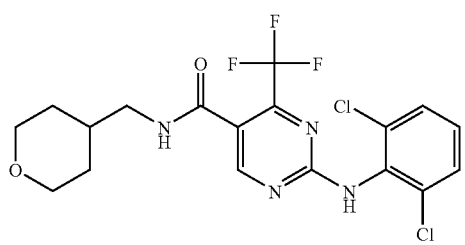

In a manner similar to Reference Example 1(c) 2-(2,6-dichlorophenylamino)-4-trifluoromethyl-pyrimidine-5-carboxylic acid (30 mg) and 4-aminomethyltetrahydropyran (20 mg, ex CombiBlocks) afforded the title compound (32 mg).

NMR (DMSO-d6) δ 1.16-1.22 (2H, m), 1.58 (2H, d), 1.70 (1H, m), 3.09 (2H, t), 3.23 (2H, m), 3.84 (2H, d), 7.38 (1H, t), 7.59 (2H, d), 8.61 (2H, m), 10.10 (1H, s)

LC/MS, t=3.02 min, Molecular ion observed (MH+)=449 consistent with the molecular formula $C_{18}H_{17}{}^{35}Cl_2F_3N_4O_2$

EXAMPLE 56

2-(3,4-Dichlorophenylamino)-4-trifluoromethylpyrimidine-5-carboxylic acid (tetrahydro-pyran-4-ylmethyl)-amide

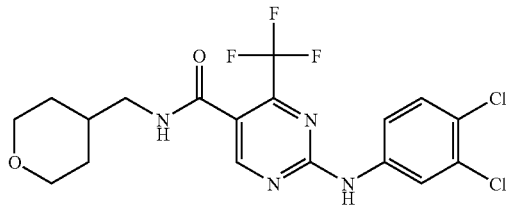

In a manner similar to Reference Example 1(c) 2-(3,4-dichlorophenylamino)-4-trifluoromethyl-pyrimidine-5-carboxylic acid (30 mg) and 4-aminomethyltetrahydropyran (20 mg, ex CombiBlocks) afforded the title compound (38 mg).

NMR (DMSO-d6) δ 1.18-1.25 (2H, m), 1.62 (2H, d), 1.74 (1H, m), 3.1 (2H, t), 3.25 (2H, m), 3.85 (2H, d), 7.60 (1H, t), 7.69 (1H, m), 8.16 (1H, dd), 8.64 (1H, t), 8.84 (1H, s), 10.70 (1H, s)

LC/MS, t=3.45 min, Molecular ion observed (MH+)=449 consistent with the molecular formula $C_{18}H_{17}N_4O_2{}^{35}Cl_2F_3$

EXAMPLE 68

1-[2-(3,4-Dichlorophenylamino)-4-trifluoromethylpyrimidin-5-yl]-1-(morpholin-4-yl)-methanone

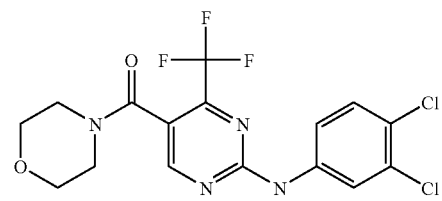

In a manner similar to Reference Example 1(c) 2-(3,4-dichlorophenylamino)-4-trifluoromethyl-pyrimidine-5-carboxylic acid (30 mg) and morpholine (15 mg, ex Aldrich) afforded the title compound (36 mg).

NMR (DMSO-d6) δ) 3.7 (8H, s), 7.65 (1H, d), 7.75 (1H, dd), 8.2 (1H, d), 8.9 (1H, s), 10.80 (1H, s)

LC/MS, t=3.45 min, Molecular ion observed (MH+)=421 consistent with the molecular formula $C_{16}H_{13}N_4O_2{}^{35}Cl_2F_3$ Table 2:

Example 57-67 and 69-73 were prepared in a corresponding fashion to the above compounds.

TABLE 2

| Compound Name | Structure | Mass spec details<br>1 Retention Time<br>2 MH+<br>3 Formula consistent with MH+ |
|---|---|---|
| 57 2-(3-Chloro-phenylamino)-4-trifluoromethyl-pyrimidine-5-carboxylic acid cycloheptylamide | 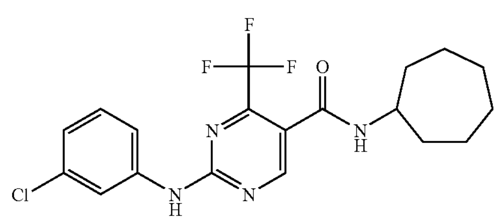 | 3.78<br>413<br>$C_{19}H_{20}{}^{35}ClF_3N_4O$ |
| 58 2-(3-Chloro-phenylamino)-4-trifluoromethyl-pyrimidine-5-carboxylic acid [(S)-1-(tetrahydro-furan-2-y-l)methyl]-amide | 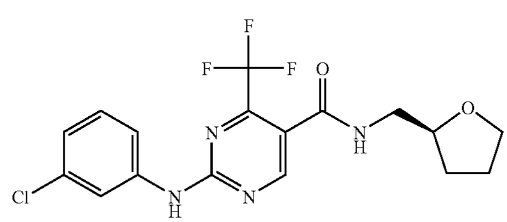 | 3.25<br>401<br>$C_{17}H_{16}{}^{35}ClF_3N_4O_2$ |

TABLE 2-continued

| Compound Name | Structure | Mass spec details<br>1 Retention Time<br>2 MH+<br>3 Formula consistent with MH+ |
|---|---|---|
| 59 2-(3-Fluoro-phenylamino)-4-trifluoromethyl-pyrimidine-5-carboxylic acid [(S)-1-(tetrahydro-furan-2-y-l)methyl]-amide | | 3.10<br>385<br>$C_{17}H_{16}F_4N_4O_2$ |
| 60 2-(3-Bromo-phenylamino)-4-trifluoromethyl-pyrimidine-5-carboxylic acid [(S)-1-(tetrahydro-furan-2-yl)methyl]-amide | | 3.29<br>447<br>$C_{17}H_1{}^{81}BrF_3N_4O_2$ |
| 61 2-(3-Chloro-phenylamino)-4-trifluoromethyl-pyrimidine-5-carboxylic acid (1-methanesulfonyl-piperidin-4-ylmethyl)-amide | | 3.22<br>492<br>$C_{19}H_{21}{}^{35}ClF_3N_5O_3S$ |
| 62 2-(2,5-Dichloro-phenylamino)-4-trifluoromethyl-pyrimidine-5-carboxylic acid cyclohexylmethyl-amide | | 3.90<br>447<br>$C_{19}H_{19}{}^{35}Cl_2F_3N_4O$ |
| 63 2-(3-Chloro-phenylamino)-4-trifluoromethyl-pyrimidine-5-carboxylic acid (1-ethyl-propyl)-amide | | 3.60<br>387<br>$C_{17}H_{18}{}^{35}ClF_3N_4O$ |

TABLE 2-continued

| Compound Name | Structure | Mass spec details<br>1 Retention Time<br>2 MH+<br>3 Formula consistent with MH+ |
|---|---|---|
| 64 2-(3-Chloro-phenylamino)-4-trifluoromethyl-pyrimidine-5-carboxylic acid (tert-butyl)-amide | | 3.55<br>373<br>$C_{16}H_{16}{}^{35}ClF_3N_4O$ |
| 65 2-(3-Chloro-phenylamino)-4-trifluoromethyl-pyrimidine-5-carboxylic acid (tetrahydro-pyran-4-yl)-amide | | 3.18<br>401<br>$C_{17}H_{16}{}^{35}ClF_3N_4O_2$ |
| 66 2-(3-Chloro-phenylamino)-4-trifluoromethyl-pyrimidine-5-carboxylic acid cyclohexyl-amide | | 3.67<br>399<br>$C_{18}H_{18}{}^{35}ClF_3N_4O$ |
| 67 1-[2-(3,5-Dichloro-phenylamino)-4-trifluoromethyl-pyrimidin-5-yl]-1-(piperidin-1-yl)-methanone | | 3.84<br>419<br>$C_{17}H_{15}{}^{35}Cl_2F_3N_4O$ |
| 69 2-Phenylamino-4-trifluoromethyl-pyrimidine-5-carboxylic acid (2,2-dimethyl-propyl)-amide | | 3.48<br>353<br>$C_{17}H_{19}F_3N_4O$ |

TABLE 2-continued

| Compound Name | Structure | Mass spec details 1 Retention Time 2 MH+ 3 Formula consistent with MH+ |
|---|---|---|
| 70 2-Phenylamino-4-trifluoromethyl-pyrimidine-5-carboxylic acid (3,3-dimethyl-butyl)-amide | | 3.60<br>367<br>$C_{18}H_{21}F_3N_4O$ |
| 71 2-(3-Chloro-phenylamino)-4-trifluoromethyl-pyrimidine-5-carboxylic acid (piperidin-4-ylmethyl)-amide trifluoroacetate | | 2.46<br>414<br>$C_{18}H_{19}{}^{35}ClF_3N_5O$ |
| 72 1-[2-(3-Chloro-phenylamino)-4-trifluoromethyl-pyrimidin-5-yl]-1-(piperazin-1-yl)-methanone | | 2.42<br>386<br>$C_{16}H_{15}{}^{35}ClF_3N_5O$ |
| 73 2-(3-Fluoro-phenylamino)-4-trifluoromethyl-pyrimidine-5-carboxylic acid [(R)-1-(tetrahydro-furan-2-yl)methyl]-amide | | 3.10<br>385<br>$C_{17}H_{16}F_4N_4O_2$ |

Table 3

Compounds 74 to 87 were prepared according to the conditions described for table 1, and purified by the method given in column P as follows:

Method A: refers to the procedure in part (b) of Example 166.

Method B: Mass-directed autopurification using the procedures detailed at the beginning of the experimental Method C: Purification using Biotage Chromatography over Merck 9385 Silica Gel (25 g) eluting with 1-2% methanol in dichloromethane.

Intermediate A: 4-Aminomethyltetrahydropyran-4-ol hydrochloride

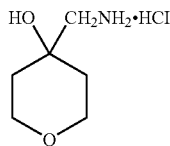

To a solution of 1.0M lithium aluminium hydride in tetrahydrofuran (20 ml) was added under a nitrogen atmosphere a solution of 4-hydroxytetra-hydropyran-4-carbonitrile (0.50 g, prepared as described in Eiden et al., Arch. Pharm., 320, 348, (1987)) in tetrahydrofuran (2 ml) and the solution stirred at reflux for 6 hours. Water (1 ml) and 2N sodium hydroxide solution (1 ml) were added cautiously and the resultant solid filtered and washed with ether. The filtrate was dried ($MgSO_4$), evaporated and the residue dissolved in ethanol (3 ml) and concentrated hydrochloric acid (0.5 ml) added. Solvent was removed under reduced pressure and the resultant solid washed with ether and dried in vacuo at 40° C. to afford the title compound (234 mg).

NMR (DMSO-d6) 1.45-1.6 (4H, m), 2.78 (2H, q), 3.61 (4H, m). 5.07 (1H, br s), 7.89 (3H, br s).

| Ex 1 | 2 | 3-Product | P | LC/MS 1 Retention time (min) 2 MH+ 3 Formula |
|---|---|---|---|---|
| 74 3,4-Dichloro-aniline (Lancaster) | Cyclo-pentylamine (Aldrich) | 3,4-Dichlorophenylamino-4-trifluoromethyl-pyrimidine-5-carboxylic acid cyclopentylamide | A | 3.53 419 $C_{17}H_{15}{}^{35}Cl_2F_3N_4O$ |
| 75 3,5-Dichloro-aniline (Lancaster) | Cyclo-pentylamine (Aldrich) | 3,5-Dichlorophenylamino-4-trifluoromethyl-pyrimidine-5-carboxylic acid cyclopentylamide | A | 3.60 419 $C_{17}H_{15}{}^{35}Cl_2F_3N_4O$ |
| 76 3-Methoxy-aniline (Lancaster) | Cyclo-pentylamine (Aldrich) | 3-Methoxyphenylamino-4-trifluoromethyl-pyrimidine-5-carboxylic acid cyclopentylamide | A | 3.08 381 $C_{18}H_{19}F_3N_4O_2$ |

-continued

| Ex | 1 | 2 | 3-Product | | LC/MS<br>1 Retention time (min)<br>2 MH+<br>P 3 Formula |
|---|---|---|---|---|---|
| 77 | 2,3-Dichloro-aniline (Lancaster) | Cyclo-pentylamine (Aldrich) | 2,3-Dichlorophenylamino-4-trifluoromethyl-pyrimidine-5-carboxylic acid cyclopentylamide | 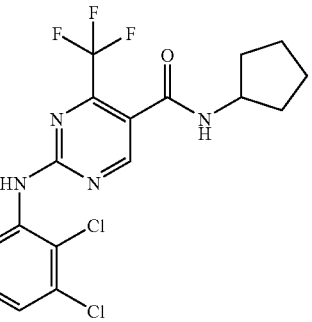 | A 3.60<br>419<br>$C_{17}H_{15}{}^{35}Cl_2F_3N_4O$ |
| 78 | 3-fluoro-aniline (Lancaster) | Piperidine (Aldrich) | 1-[2-(3-fluorophenylamino)-4-trifluoromethyl-pyrimidin-5-yl]-1-piperidin-1-yl-methanone | 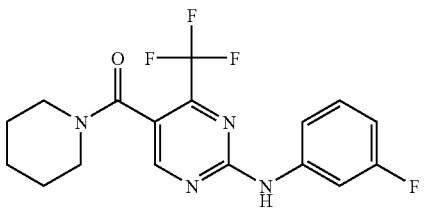 | A 3.39<br>369<br>$C_{17}H_{16}N_4F_4O$ |
| 79 | 3-chloro-aniline (Lancaster) | 1-methane-sulfonyl-piperazine (US 5081147) | 1-[2-(3-chlorophenylamino)-4-trifluoromethyl-pyrimidin-5-yl]-1-(4-methanesulfonyl-piperazin-1-yl)-methanone | 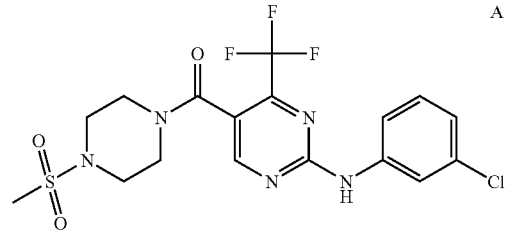 | A 3.21<br>464<br>$C_{17}H_{17}Cl^{35}F_3N_5O_3S$ |
| 80 | 3-bromo-aniline (Lancaster) | R-1-(tetra-hydrofuran-2-yl) methylamine (Lancaster) | 2-(3-bromophenylamino)-4-trifluoromethyl-pyrimidine-5-carboxylic acid [R-1-(tetrahydrofuran-2-yl)methyl]-amide | 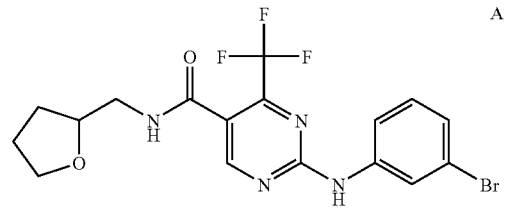 | A 3.29<br>447<br>$C_{17}H_{16}{}^{81}BrF_3N_4O_2$ |
| 81 | 2,3-dichloro-aniline | tetrahydro-thiopyran-4-ylamine JOC 46(22), 4376-83 1981 | 2-(2,3-Dichlorophenylamino)-4-trifluoromethyl-pyrimidine-5-carboxylic acid (tetrahydro-thiopyran-4-yl)-amide | 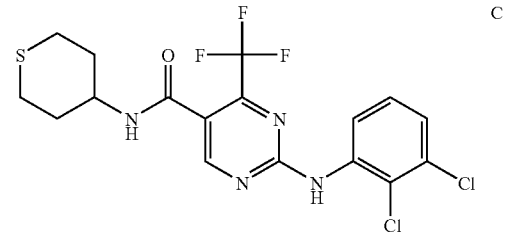 | C 3.74<br>451<br>$C_{17}H_{15}{}^{35}Cl_2F_3N_4OS$ |
| 82 | 2,3-dichloro-aniline | (1,1-dioxo-tetrahydro-2H-thiopyran-4-yl)amine hydro-chloride WO 0218380 | 2-(2,3-Dichlorophenylamino)-4-trifluoromethyl-pyrimidine-5-carboxylic acid (1,1-dioxo-tetrahydro-2H-thiopyran-4-yl)-amide | 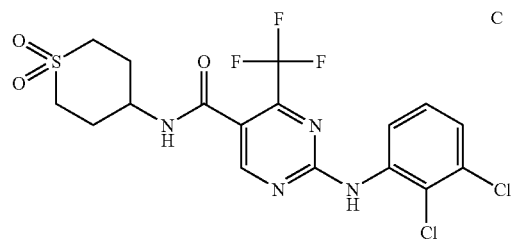 | C 3.29<br>483<br>$C_{17}H_{15}{}^{35}Cl_2F_3N_4O_3S$ |

-continued

| Ex | 1 | 2 | 3-Product | | LC/MS 1 Retention time (min) P | 2 MH+ 3 Formula |
|---|---|---|---|---|---|---|
| 83 | 3-fluoro-aniline (Lancaster) | cyclo-propyl-methyl-amine (Lancaster) | 2-(3-Fluoro-phenylamino)-4-trifluoromethyl-pyrimidine-5-carboxylic acid cyclopropylmethyl-amide | | A | 3.32 355 $C_{16}H_{14}F_4N_4O$ |
| 84 | 3-chloro-aniline (Lancaster) | cyclo-propyl-methyl-amine (Lancaster) | 2-(3-Chloro-phenylamino)-4-trifluoromethyl-pyrimidine-5-carboxylic acid cyclopropylmethyl-amide | | B | 3.46 371 $C_{16}H_{14}{}^{35}ClF_3N_4O$ |
| 85 | 2,5-Di-chloro-aniline (ex Lancaster) | Morpholine (ex Aldrich) | 1-[2-(2,5-Dichloro-phenylamino)-4-tri-fluoromethyl-pyrimidin-5-yl]-1-piperidin-1-yl-methanone | | A | 3.64 419 $C_{17}H_{15}{}^{35}Cl_2F_3N_4O$ |
| 86 | 3-Fluoro-aniline (ex Lancaster) | 1-Amino-methyl-1-cyclohexanol hydro-chloride (ex Aldrich) | 2-(3-Fluorophenyl-amino)4-trifluoro-methyl-pyrimidine-5-carboxylic acid(1-hydroxy-cyclohexyl-methyl)amide | | A | 3.25 411 $C_{19}H_{20}F_4N_4O_2$ |
| 87 | 3-Bromo-aniline (ex Lancaster) | 4-Amino-methyl-tetrahydro-4H-pyran-4-ol hydrochloride (Intermediate A) 2-(3-Bro-mophenyl-amino)-4-trifluorom-ethyl-pyrimi-dine-5-carboxylic acid (4-hydroxytet-rahydropyran-4-ylmethyl)a-mide | | | A | 3.05 473 $C_{18}H_{18}{}^{79}BrF_3N_4O_3$ |

Table 4

In the following table 4, column 2 gives precursors $R^2NH_2$ that were reacted with 2-chloro (trifluoromethyl)pyrimidine-5-carbonyl chloride in a manner similar to that in part (a) of Example 166. The resultant product was reacted with the precursor YNH2 of column 3 in a manner similar to that in part (b) of Example 166, to provide the final product in column 4.

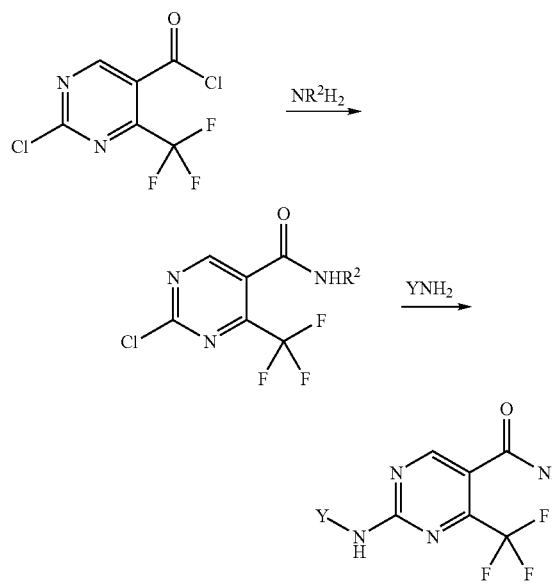

Preparation Method A: refers to the procedure give in part (b) of Example 166.

Preparation Method B: This is exemplified by the by Example 109, 2-chloro-4-trifluoromethyl-pyrimidin-5-carboxylic acid (tetrahydropyran-4-ylmethyl)amide (50 mg) and 2-chloro-2-cyanoaniline (118 mg) were irradiated in a microwave apparatus (the model used was the 'Creator', supplied by 'Personal Chemistry', operating at 300 Watts), at 190° C. for 30 min. For examples using this method, the equivalents of substituted aniline YNH2 used, and duration of irradiation follow in brackets after the method B.

The column entitled "Prep" refers to the preparation method used.

The product was then purified according to on of the following methods described below. The column entitled "Pure" refers to the purification method used Purification method A: refers to the procedure give in part (b) of Example 166

Purification method B: mass directed autopurification using the procedures detailed at the beginning of the experimental.

Purification method C: The reaction was worked up as for part (b) of Example 166, and the crude product further purified by Biotage chromatography over Merck 9385 silica gel, eluting with isohexane/ethyl acetate.

TABLE 4

| | Cyclo-hexanemet hanamine NR²H₂ | YNH₂ | Compound | Prep | Pure | Structure | LCMS 1 Retention time 2 MH+ 3 Formula consistent with MH+ |
|---|---|---|---|---|---|---|---|
| 88 | Cyclo-hexanemet hanamine (Aldrich) | 3,5-Bis-trifluoro-methyl-phenyl-amine (Aldrich) | 2-(3,5-Bis-trifluoro-methyl-phenylamino)-4-trifluoro-methyl-pyrimidine-5-carboxylic acid cyclohexyl-methyl-amide | A | B | 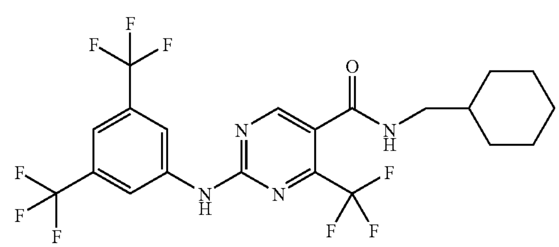 | 4.09 515 $C_{21}H_{19}F_9N_4O$ |
| 9 | Cyclo-hexanemet hanamine | 5-Amino-isophtha-lonitrile | 2-(3,5-Dicyano-phenylamino)-4-trifluoro-methyl-pyrimidine-5-carboxylic acid cyclo-hexylmethyl-amide | A | B | 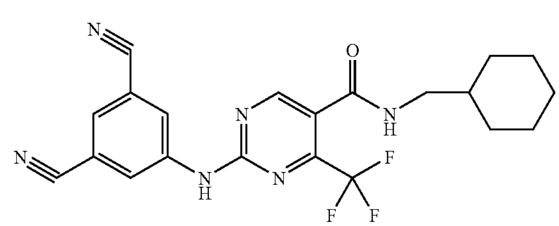 | 3.59 429 $C_{21}H_{19}F_3N_4O$ |

TABLE 4-continued

| | Cyclo-hexanemet hanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 90 | Cyclo-hexanemet hanamine | 3-Fluoro-5-tri-fluoro-methyl-phenyl-amine (Supplier Apollo) | 2-(3-Fluoro-5-trifluoro-methyl-phenylamino)-4-trifluoro-methyl-pyrimidine-5-carboxylic acid cyclohexyl-methyl-amide | A | B | 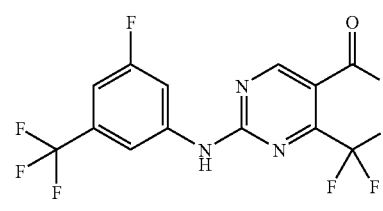 | 3.96 465 C₂₀H₁₉F₇N₄O |
| 91 | Cyclo-hexanemet hanamine | 3-Bromo-5-tri-fluoro-methyl-phenyl-amine (Supplier Avacado) | 2-(3-Bromo-5-trifluoro-methyl-phenylamino)-4-trifluoro methyl pyrimidine-5-carboxylic acid cyclohexyl-methyl-amide | A | B | 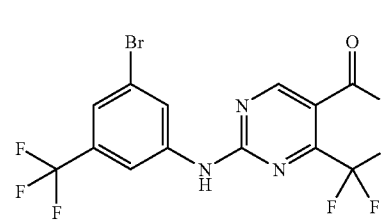 | 4.13 524 C₂₀H₁₉⁷⁹BrF₆N₄O |
| 92 | Cyclo-hexanemet hanamine | 2-Chloro-3-methyl-phenyl-amine (WO 97/41846-hydro-genate 2-chloro-3-nitroto-luene) | 2-(2-Chloro-3-methyl-phenylamino)-4-trifluoro-me-thyl-pyrimidine-5-carboxylic acid cyclohexyl-methyl-amide | A | B | 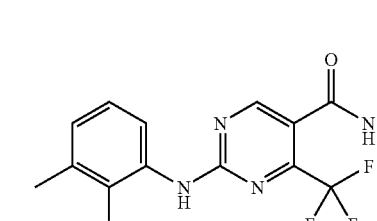 | 3.82 427 C₂₀H₂₂³⁵ClF₃N₄O |
| 93 | Cyclo-hexanemet hanamine | 3-Chloro-2-methyl-phenyl-amine (Supplier Aldrich) | 2-(3-Chloro-2-methyl-phenylamino)-4-trifluoro-methyl-pyrimidine-5-carboxylic acid | A | B | 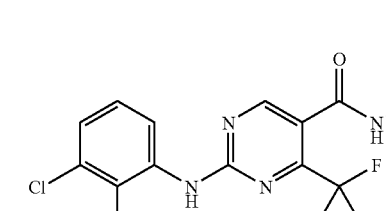 | 3.76 427 C₂₀H₂₂³⁵ClF₃N₄O |
| 94 | Cyclo-hexanemet hanamine | 4-Chloro-2-methyl-phenyl-amine (Supplier Aldrich) | 2-(4-Chloro-2-methyl-phenylamino)-4-trifluoro-methyl-pyrimidine-5-carboxyl acid cyclohexyl-methyl-amide | A | B | 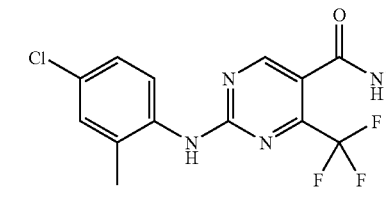 | 3.77 427 C₂₀H₂₂³⁵ClF₃N₄O |

TABLE 4-continued

| | Cyclo-hexanemethanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 95 | Cyclohexanemethanamine | 4-Chloro-2,6-dimethyl-phenylamine (Supplier Davos) | 2-(4-Chloro-2,6-dimethyl-phenylamino)-4-trifluoromethyl-pyrimidine-5-carboxylic acid pyrimidine-5-carboxylic acid | A | B | 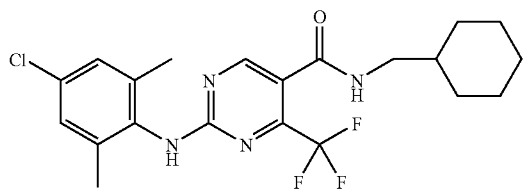 | 3.79 441 C₂₁H₂₄³⁵ClF₃N₄O |
| 96 | Cyclopentanemethanamine | 3,5-difluoroaniline (Aldrich) | 2-(3,5-Difluoro-phenylamino)-4-trifluoromethyl-pyrimidine-5-carboxylic acid cyclopentyl-methyl-amide | A | C | 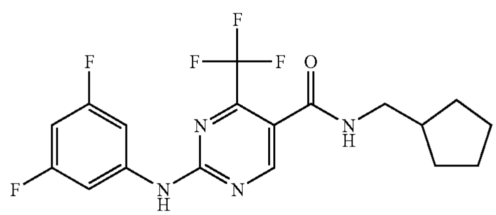 | 3.70 401 C₁₈H₁₇F₅N₄O |
| 97 | Cyclopentanemethanamine | 3-Fluoro-4-(trifluoromethy)aniline (Fluorochem) | 2-(4-Trifluoromethyl-3-fluorophenyl-amino)-4-trifluoromethyl-pyrimidine-5-carboxylic acid cyclopentyl-methyl-amide | A | B | 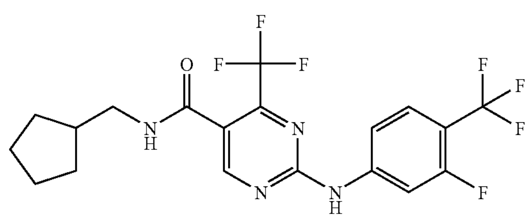 | 3.86 451 C₁₉H₁₇F₇N₄O |
| 98 | 4-Amino-methyl-tetrahydropyran (Combi-Blocks) | 2,4-Difluoroaniline (Lancaster) | 2-(2,4-Difluorophenyl-amino)-4-trifluoromethyl-pyrimidine-5-carboxylic acid (tetrahydropyran-4-ylmethyl)-amide | A | A | 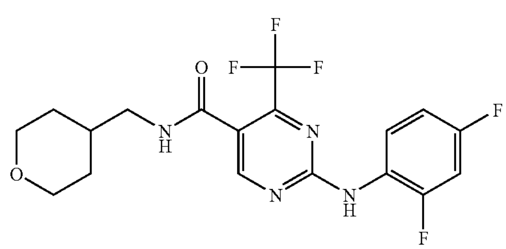 | 3.03 417 C₁₈H₁₇F₅N₄O₂ |
| 99 | 4-Amino-methyl-tetrahydropyran (Combi-Blocks) | 2-Fluoro-4-chloroaniline (Lancaster) | 2-(2-Fluoro-4-chlorophenyl-amino)-4-trifluoromethyl-pyrimidine-5-carboxylic acid (tetrahydropyran-4-ylmethyl)-amide | A | A | 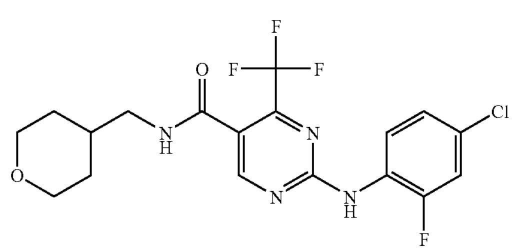 | 3.23 433 C₁₈H₁₇³⁵ClF₄N₄O₂ |

TABLE 4-continued

| | Cyclohexanemethanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 100 | Cyclohexane-methanamine (Lancaster) | 2-Trifluoromethyl-4-fluoroaniline (Lancaster) | 2-(2-Trifluoromethyl-4-fluorophenylamino)-4-trifluoromethyl-pyrimidine-5-carboxylic acid cyclohexyl-methyl-amide | A | B | 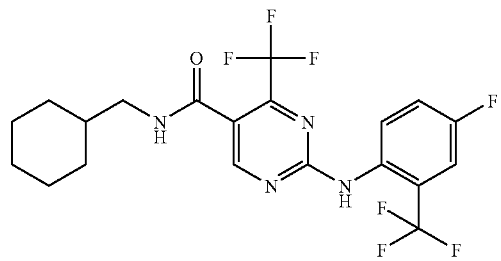 | 3.69 465 $C_{20}H_{19}F_7N_4O$ |
| 101 | Cyclobutane-methamine | 2-Trifluoromethyl-4-fluoroaniline (Lancaster) | 2-(2-Trifluoromethyl-4-fluorophenylamino)-4-trifluoromethyl-pyrimidine-5-carboxylic acid cyclobutyl-methyl-amide | A | B | 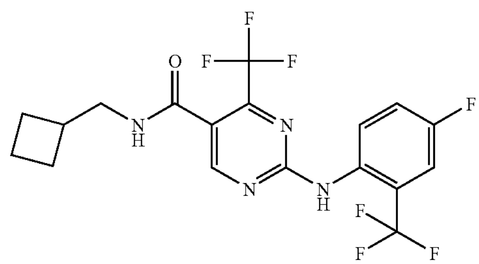 | 3.49 437 $C_{18}H_{15}F_7N_4O$ |
| 102 | Cyclobutane-methamine | 2-Chloro-4-trifluoromethylaniline (Lancaster) | 2-(2-Chloro-4-trifluoromethylphenyl-amino)-4-trifluoromethyl-pyrimidine-5-carboxylic acid cyclobutyl-methyl-amide | A | B | 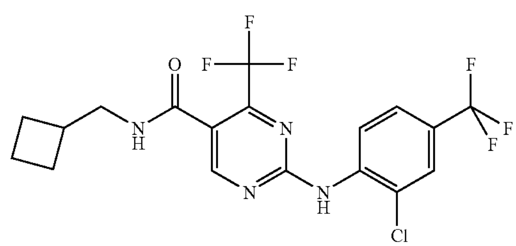 | 3.79 453 $C_{18}H_{15}{}^{35}ClF_6N_4O$ |
| 103 | Cyclobutane-methamine | 2-Chloro-4-cyanoaniline (Lancaster) | 2-(2-Chloro-4-cyano-phenyl-amino)-4-trifluoromethyl-pyrimidine-5-carboxylic acid cyclobutyl-methyl-amide | B | C | 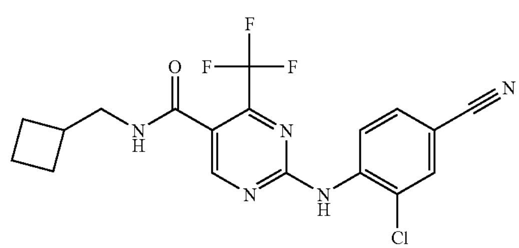 | 3.47 410 $C_{18}H_{15}{}^{35}ClF_3N_5O$ |
| 104 | 4-Aminomethyl-tetrahydropyran (Combi-Blocks) | 2-Trifluoromethyl-4-chloroaniline (Lancaster) | 2-(2-Trifluoromethyl-4-chlorophenyl-amino)-4-trifluoro-pyrimidine-5-carboxylic acid (tetrahydro-pyran-4-ylmethyl)-amdie | A | A | 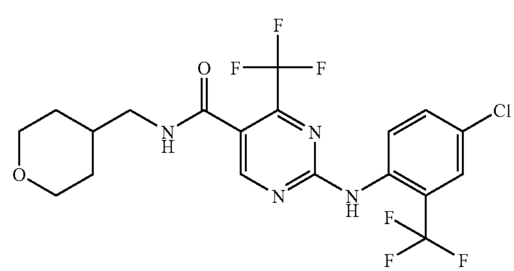 | 3.34 483 $C_{19}H_{17}{}^{35}ClF_6N_4O_2$ |

TABLE 4-continued

| | Cyclo-hexanemethanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 105 | Cyclobutyl-methyl-amine | 2-Tri-fluoro-methyl-4-bromo-aniline (Lancaster) | 2-(2-Trifluoro-methyl-4-bromophenyl-amino)-4-trifluoro-methyl-pyrimidine-5-carboxylic acid cyclobutyl-methyl-amide | B (5 equiv, 45 min) | B | 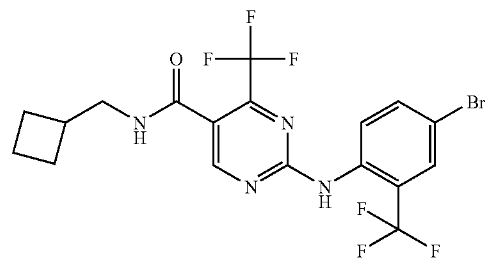 | 3.71 499 C₁₈H₁₅⁸¹BrF₆N₄O |
| 106 | Cyclohexyl-methyl-4-bromo-aniline (Lancaster) | 2-Tri-fluoro-methyl-4-bromo-aniline (Lancaster) | 2-(2-Trifluoro-methyl-4-bromophenyl-amino)-4-trifluoromethyl-pyrimidine-5-carboxylic acid cyclohexyl-methyl-amide | B (2.5 equiv, 45 min) | B | | 3.89 527 C₂₀H₁₉⁸¹BrF₆N₄O |
| 107 | 4-Amino-methyl-tetra-hydro-nl pyran (ex Combi Blocks) | 2,3-Di-fluoro-aniline (ex Aldrich) | 2-(2,3-Difluoro-phenyl-amino)-4-trifluoro-methyl-pyri-midine-5-carboxylic acid (tetrahydro-pyran-4-ylmethyl)-amide | A | B | 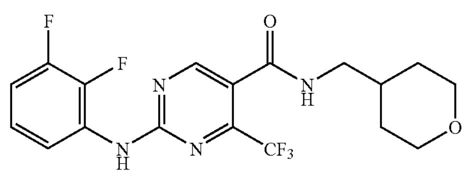 | 3.64 417 C₁₈H₁₇F₅N₄O₂ |
| 108 | 4-Amino-methyl-tetra-hydro-nl pyran (ex Combi Blocks) | 5-Chloro-2-methyl-aniline (ex Aldrich) | 2-(5-Chloro-2-methyl-phenyl-amino)-4-tri-fluoromethyl-pyrimidine-5-carboxylic acid (tetrahydro-pyran-4-yl-methyl)-amide | A | B | 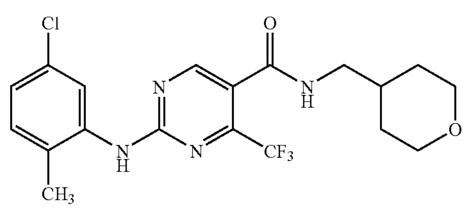 | 3.64 429 C₁₉H₂₀³⁵ClF₃N₄O₂ |
| 109 | 4-Amino-methyl-tetra-hydro-nl pyran (ex Combi Blocks) | 3-Chloro-2-cyano-aniline (ex Lancaster) | 2-(3-Chloro-2-cyano-phenyl-amino)-4-tri-fluoromethyl-pyrimidine-5-carboxylic acid (tetrahydro-pyran-4-yl-methyl)-amide | B | B | 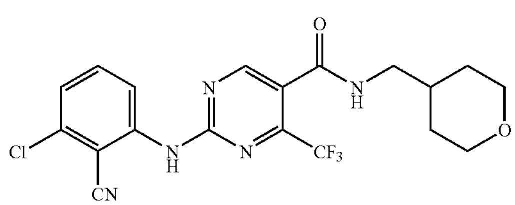 | 3.64 440 C₁₉H₁₇³⁵ClF₃N₅O₂ |

TABLE 4-continued

| | Cyclohexanemethanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 110 | 4-Aminomethyltetrahydro-nl pyran (ex Combi Blocks) | 2-Chloro-4-methylanilin | 2-(2-Chloro-4-methyl-phenyl-amino)-4-trifluoromethyl-pyrimidine-5-carboxylic acid (tetrahydro-pyran-4-yl-methyl)-amide | A | B | 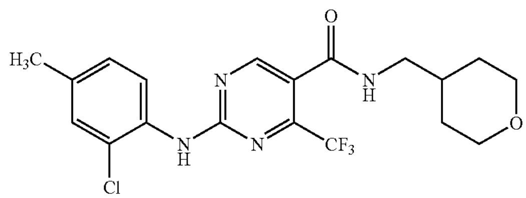 | 3.27 429 C₁₉H₂₀ ³⁵ClF₃N₄O₂ |
| 111 | 4-Aminomethyltetrahydro-nl pyran (ex Combi Blocks) | 4-Chloro-3-cyano-aniline | 2-(4-Chloro-3-cyano-phenyl-amino)-4-trifluoromethyl-pyrimidine-5-carboxylic acid (tetrahydro-pyran-4-yl-methyl)-amide | A | B | 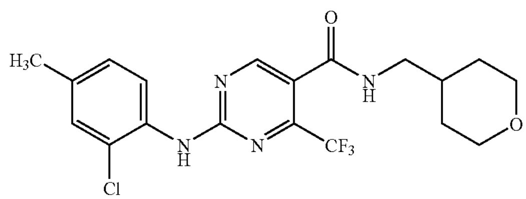 | 3.22 429 C₁₉H₂₀ ³⁵ClF₃N₄O₂ |
| 112 | 4-Aminomethyltetrahydro-nl pyran (ex Combi Blocks) | 4-Chloro-3-cyano-aniline | 2-(4-Chloro-3-cyano-phenyl-amino)-4-fluoromethyl-pyrimidine-5-carboxylic acid (tetrahydro-pyran-4-yl-methyl)-amide | A | B | 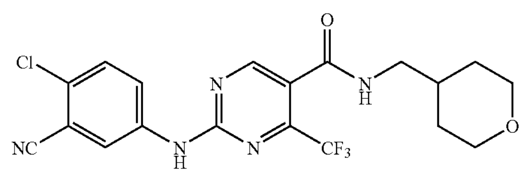 | 3.22 440 C₁₉H₁₇ ³⁵ClF₃N₅O₂ |
| 113 | 4-Aminomethyltetrahydro-nl pyran (ex Combi Blocks) | 2-Chloro-5-methyl-aniline (ex Aldrich) | 2-(2-Chloro-5-methyl-phenyl-amino)-4-trifluoromethyl-pyrimidine-5-carboxylic acid (tetrahydro-pyran-4-yl-methyl)-amide | A | B | 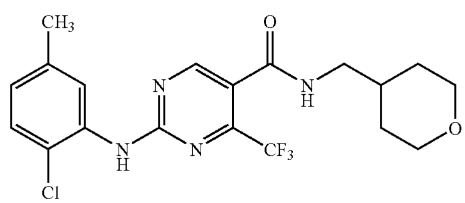 | 3.28 429 C₁₉H₂₀ ³⁵ClF₃N₄O₂ |
| 257 | (Cyclobutyl-methyl-amine | 2-Chloro-aniline | 2-(2-Chloro-phenyl-amino)-4-trifluoro-methyl-pyrimidine-5-carboxylic acid cyclobutyl-methyl-amid | C | B | 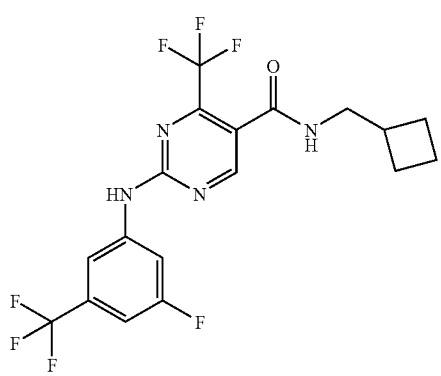 | 3.52 385 C₁₇H₁₆ ³⁵ClF₃N₄O |

TABLE 4-continued

| | Cyclo-hexanemet hanamine NR²H₂ | YNH₂ | Compound | Prep | Pure | Structure | LCMS 1 Retention time 2 MH⁺ 3 Formula consistent with MH⁺ |
|---|---|---|---|---|---|---|---|
| 258 | (Cyclo-butyl-methyl)-amime | 3-Fluoro-5-trifluoro-methyl-aniline | 2-(3-Fluoro-5-trifluoro-methylphenyl-amino)-4-tri-fluoromethyl-pyrimidine-5-carboxylic acid cyclobutyl-methyl-amide | C | B | 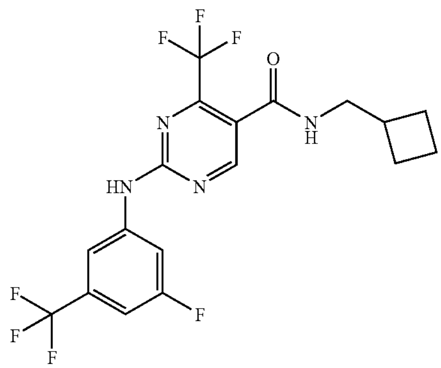 | 3.80 437 C₁₈H₁₅F₇N₄O |
| 259 | (Cyclo-butyl-methyl)-amime | 5-Chloro-2-methyl-aniline | 2-(5-Chloro-2-methylphenyl-amino)-4-tri-fluoromethyl-pyrimidine-5-carboxylic acid cyclobutyl-methyl-amide | C | B | 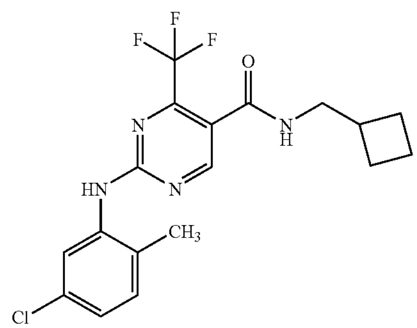 | 3.61 399 C₁₈H₁₈³⁵ClF₃N₄O |

**In Example 103 - Preparation Method B (5 equiv, 15 min)
N.B. Reaction mixture also contained 0.5 ml MeCN and purification method C The product was purified by trituration with isohexane after this.
Method C - As for method B, but the solvent used was 1,4-dioxan not MeCN

TABLE 5

| | Compound Name | Structure | Purification method | Mass spec details 1 Retention Time 2 MH⁺ 3 Formula consistent with MH⁺ |
|---|---|---|---|---|
| 114 | 3-Fluorophenylamino-4-trifluoromethyl-pyrimidine-5-carboxylic acid cyclopentyl-amide | 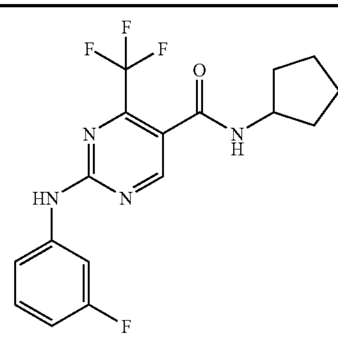 | A | 3.23 369 C₁₇H₁₆F₄N₄O |

TABLE 5-continued

| | Compound Name | Structure | Purification method | Mass spec details<br>1 Retention Time<br>2 MH+<br>3 Formula consistent with MH+ |
|---|---|---|---|---|
| 115 | 2,6-Dichlorophenylamino-4-trifluoromethyl-pyrimidine-5-carboxylic acid cyclopentyl-amide | 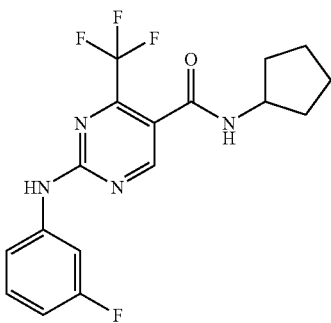 | A | 3.17<br>419<br>$C_{17}H_{15}{}^{35}Cl_2F_3N_4O$ |
| 116 | 3-Chlorophenylamino-4-trifluoromethylpyrimidine-5-carboxylic acid (2-ethylbutyl)-amide | 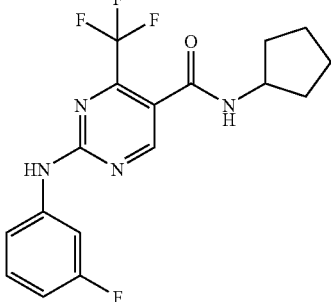 | A | 3.79<br>401<br>$C_{18}H_{20}{}^{35}ClF_3N_4O$ |
| 117 | 2-Phenylamino-4-trifluoromethyl-pyrimidin-5-carboxylic acid (2-methoxy-ethyl)-amide | 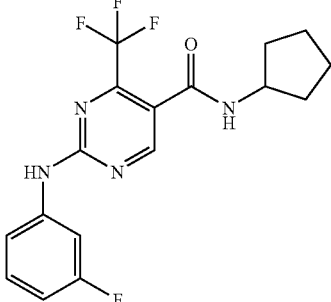 | A | 2.98<br>339<br>$C_{15}H_{15}F_3N_4O_2$ |
| 118 | 2-Phenylamino-4-trifluoromethyl-pyrimidin-5-carboxylic acid [2-(dimethyl-amino)ethyl]-amide | 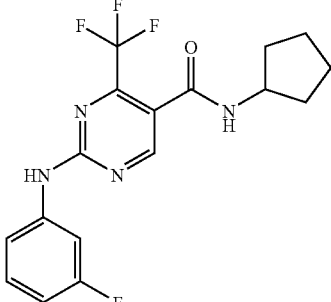 | A | 2.32<br>354<br>$C_{16}H_{18}F_3N_5O$ |

TABLE 5-continued

| Compound Name | Structure | Purification method | Mass spec details<br>1 Retention Time<br>2 MH+<br>3 Formula consistent with MH+ |
|---|---|---|---|
| 119 1-[2-(3-Chlorophenyl-amino)-4-trifluoro-methylpyrimidin-5-yl]-1-(4-methoxypiperin-1-yl)-methanone | 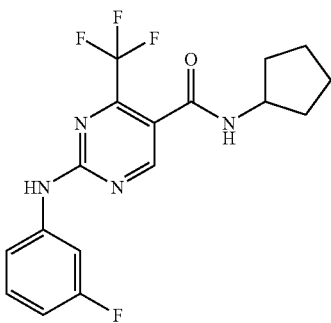 | A | 3.33<br>415<br>$C_{18}H_{18}{}^{35}ClF_3N_4O_2$ |
| 120 1-[2-(3-Chlorophenyl-amino)-4-trifluoro-methylpyrimidin-5-yl]-1-(1,1-dioxothiomorph-olin-4yl)-methanone | 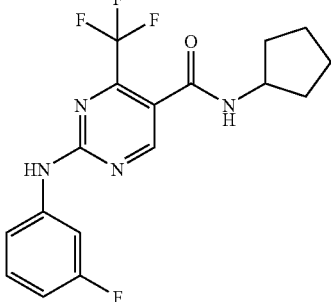 | A | 3.16<br>435<br>$C_{16}H_{14}{}^{35}ClF_3N_4O_3S$ |
| 121 N-((R)-1-{1-[2-(3-Chlorophenylamino)-4-trifluoromethyl-pyrimidin-5-yl]-methanoyl}-pyrrolidin-3-yl)-acetamide | 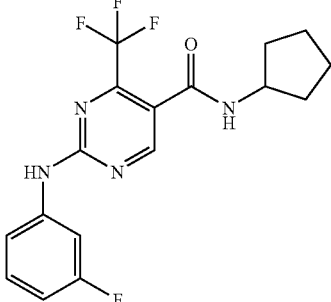 | A | 2.91<br>428<br>$C_{18}H_{17}{}^{35}ClF_3N_5O_2$ |
| 122 N-((S)-1-{1-[2-(3-Chlorophenylamino)-4-trifluoromethyl-pyrimidin-5-yl]-methanoyl}-pyrrolidin-3-yl)-acetamide | 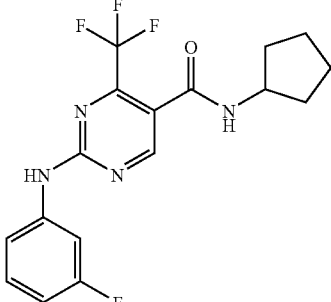 | A | 2.91<br>428<br>$C_{18}H_{17}{}^{35}ClF_3N_5O_2$ |

TABLE 5-continued

| | Compound Name | Structure | Purification method | Mass spec details<br>1 Retention Time<br>2 MH+<br>3 Formula consistent with MH+ |
|---|---|---|---|---|
| 123 | 1-{1-[2-(3-Chloro-phenylamino)-4-tri-fluoromethyl-pyrimidin-5-yl]-methanoyl}-piperidine-4-carboxylic acid methylamide | 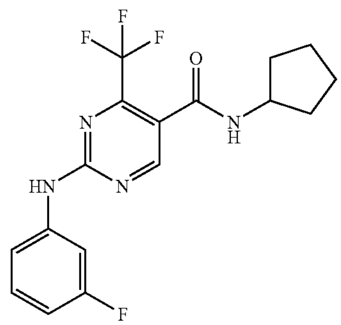 | C<br>Sol 1 | 2.98<br>442<br>$C_{19}H_{19}{}^{35}ClF_3N_5O_2$ |
| 124 | 2-(3-Chlorophenyl-amino)-4-trifluoromethylpyrimidine-5-carboxylic acid (4-hydroxytetrahydropyran-4-ylmethyl)-amide | 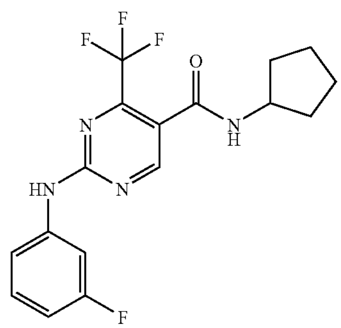 | A | 3.00<br>429<br>$C_{18}H_{18}{}^{35}ClF_3N_4O_3$ |
| 125 | 2-(3-Fluorophenyl-amino)-4-trifluoromethylpyrimidine-5-carboxylic acid (1-hydroxytetrahydropyran-4-ylmethyl)-amide | 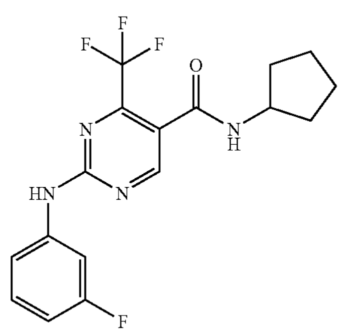 | A | 2.86<br>413<br>$C_{18}H_{18}F_4N_4O_3$ |
| 126 | 1-[2-(3-Chlorophenylamino)-4-trifluoromethylpyrimidin-5-yl]-1-(4-methylpiperazin-1-yl)-methanone | 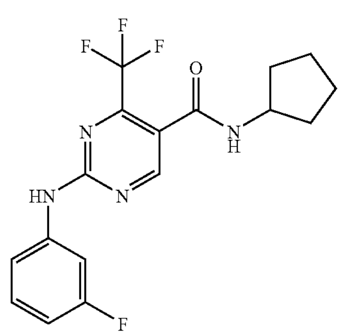 | A | 2.53<br>400<br>$C_{17}H_{17}{}^{35}ClF_3N_5O$ |

TABLE 5-continued

| | Compound Name | Structure | Purification method | Mass spec details<br>1 Retention Time<br>2 MH+<br>3 Formula consistent with MH+ |
|---|---|---|---|---|
| 127 | 2-(3-Chlorophenylamino)-4-trifluoromethylpyrimidine-5-carboxylic acid (2-methoxy-ethyl)-amide | 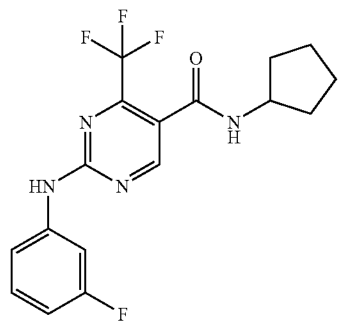 | A | 3.23<br>375<br>$C_{15}H_{14}{}^{35}ClF_3N_4O_2$ |
| 128 | 2-(3-Chlorophenylamino)-4-trifluoromethylpyrimidine-5-carboxylic acid (2-dimethylamino-ethyl)-amide | 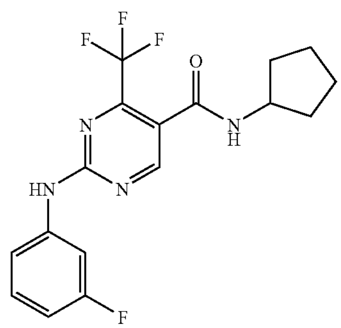 | A | 2.51<br>388<br>$C_{16}H_{17}{}^{35}ClF_3N_5O$ |
| 129 | 2-(3-chlorophenylamino)-4-trifluoromethylpyrimidine-5-carboxylic acid [R-1-(tetrahydrofuran-2-yl)methyl]-amide | 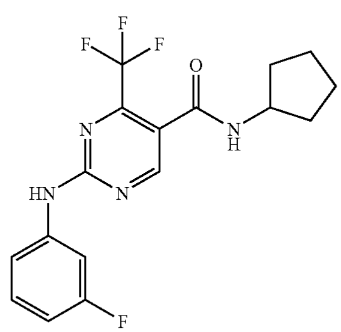 | A | 3.25<br>401<br>$C_{17}H_{16}{}^{35}ClF_3N_4O_2$ |
| 130 | 2-(Phenylamino)-4-trifluoromethylpyrimidine-5-carboxylic acid (tetrahydro-pyran-4-ylmethyl)-amide | 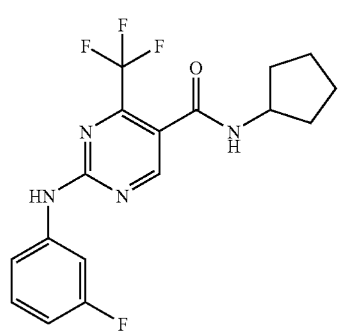 | A | 3.01<br>381<br>$C_{18}H_{19}F_3N_4O_2$ |

TABLE 5-continued

| | Compound Name | Structure | Purification method | Mass spec details<br>1 Retention Time<br>2 MH+<br>3 Formula consistent with MH+ |
|---|---|---|---|---|
| 131 | 2-(2,3-Dichlorophenylamino)-4-trifluoromethylpyrimidine-5-carboxylic acid cyclohexylamide | 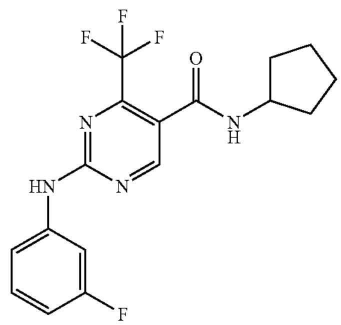 | C<br>Sol 2 | 3.74<br>433<br>$C_{18}H_{17}{}^{35}Cl_2F_3N_4O$ |
| 132 | 2-(3-Fluorophenylamino)-4-trifluoromethylpyrimidine-5-carboxylic acid cyclohexylamide | 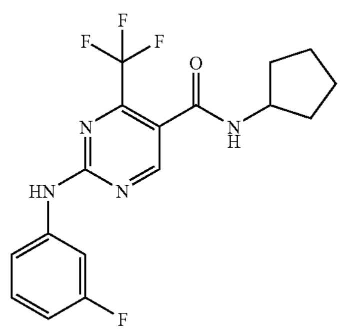 | A | 3.56<br>383<br>$C_{18}H_{18}F_4N_4O$ |
| 133 | 2-(3-Bromophenylamino)-4-trifluoromethylpyrimidine-5-carboxylic acid cyclohexylamide | 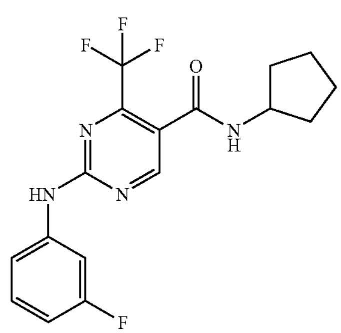 | A | 3.74<br>445<br>$C_{18}H_{18}{}^{81}BrF_3N_4O$ |
| 134 | 2-(3-Fluorophenylamino)-4-trifluoromethylpyrimidine-5-carboxylic acid (tetrahydropyran-4-yl)-amide | 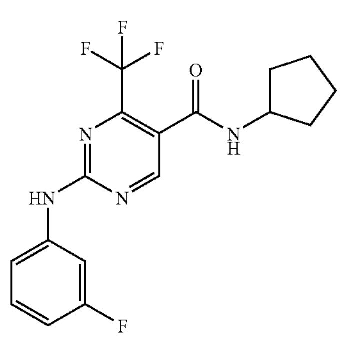 | A | 3.06<br>385<br>$C_{17}H_{16}F_4N_4O_2$ |

TABLE 5-continued

| Compound Name | Structure | Purification method | Mass spec details 1 Retention Time 2 MH+ 3 Formula consistent with MH+ |
|---|---|---|---|
| 135 2-(3-Bromophenylamino)-4-trifluoromethylpyrimidine-5-carboxylic acid (tetrahydropyran-4-yl)-amide | | A | 3.26<br>447<br>$C_{17}H_{16}{}^{81}BrF_3N_4O_2$ |
| 136 2-(2,4-Dichlorophenylamino)-4-trifluoromethylpyrimidine-5-carboxylic acid (tetrahydropyran-4-yl)-amide | | A | 3.33<br>435<br>$C_{17}H_{15}{}^{35}Cl_2F_3N_4O_2$ |
| 137 2-(2,4-Dichlorophenylamino)-4-trifluoromethylpyrimidine-5-carboxylic acid cyclohexylamide | | A | 3.79<br>433<br>$C_{18}H_{17}{}^{35}Cl_2F_3N_4O$ |
| 138 2-(3,4-Dichlorophenylamino)-4-trifluoromethylpyrimidine-5-carboxylic acid cyclohexylamide | | A | 3.90<br>433<br>$C_{18}H_{17}{}^{35}Cl_2F_3N_4O$ |

TABLE 5-continued

| Compound Name | Structure | Purification method | Mass spec details<br>1 Retention Time<br>2 MH+<br>3 Formula consistent with MH+ |
|---|---|---|---|
| 139  2-(2,3-Dichlorophenylamino)-4-trifluoromethylpyrimidine-5-carboxylic acid (tefrahydropyran-4-yl)-amide | | A | 3.26<br>435<br>$C_{17}H_{15}{}^{35}Cl_2F_3N_4O_2$ |
| 140  2-(3-Fluorophenylamino)-4-trifluoromethylpyrimidine-5-carboxylic acid-(tetrahydro-thiopyran-4-yl)-amide | | C<br>Sol 2 | 3.37<br>401<br>$C_{17}H_{16}F_4N_4OS$ |
| 141  2-(3-Chlorophenylamino)-4-trifluoromethylpyrimidine-5-carboxylic acid (tetrahydro-thiopyran-4-yl)-amide | | C<br>Sol 2 | 3.51<br>417<br>$C_{17}H_{16}{}^{35}ClF_3N_4OS$ |
| 142  2-(3-Bromophenylamino)-4-trifluoromethylpyrimidine-5-carboxylic acid (tetrahydro-thiopyran-4-yl)-amide | | C<br>Sol 2 | 3.55<br>463<br>$C_{17}H_{16}{}^{81}BrF_3N_4OS$ |

TABLE 5-continued

| | Compound Name | Structure | Purification method | Mass spec details<br>1 Retention Time<br>2 MH+<br>3 Formula consistent with MH+ |
|---|---|---|---|---|
| 143 | 2-(2,4-Dichlorophenylamino)-4-trifluoromethylpyrimidine-5-carboxylic acid (tetrahydro-thiopyran-4-yl)-amide | 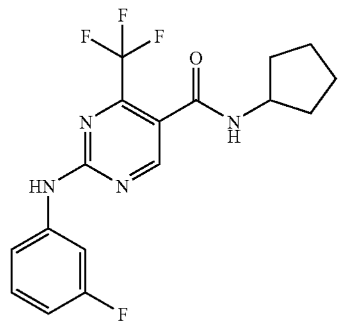 | C<br>Sol 2 | 3.61<br>451<br>$C_{17}H_{15}{}^{35}Cl_2F_3N_4OS$ |
| 144 | 2-(3,4-Dichlorophenylamino)-4-trifluoromethylpyrimidine-5-carboxylic acid (tetrahydro-thiopyran-4-yl)-amide | 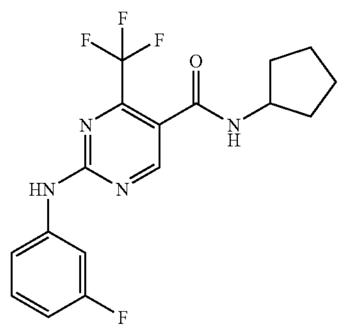 | C<br>Sol 2 | 3.72<br>451<br>$C_{17}H_{15}{}^{35}Cl_2F_3N_4OS$ |
| 145 | 2-(3,4-Dichlorophenylamino)-4-trifluoromethylpyrimidine-5-carboxylic acid (1,1-dioxo-hexahydro-1 l$^6$-thiopyran-4-yl)-amide | 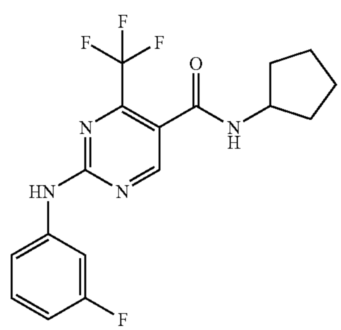 | C<br>Sol 3 | 3.32<br>483<br>$C_{17}H_{15}{}^{35}Cl_2F_3N_4O_3S$ |
| 260 | 3-Chlorophenylamino-4-trifluoromethyl-pyrimidine-5-carboxylic acid 2-(hydroxypropyl)amide | 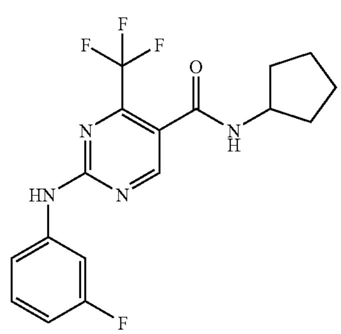 | A | 3.09<br>375<br>$C_{15}H_{14}{}^{35}ClF_3N_4O_2$ |

Compounds 114 to 145 were prepared as set out for table 2 and purified as follows:
Purification Method A: as for reference example 1c,
Purification Method C: The reaction was worked up as in example 1c, and the product purified by Biotage chromatography using the following solvent systems:
Sol 1 ethyl acetate
Sol 2 1% methanol in dichloromethane
Sol 3 2% methanol in dichloromethane Table 6

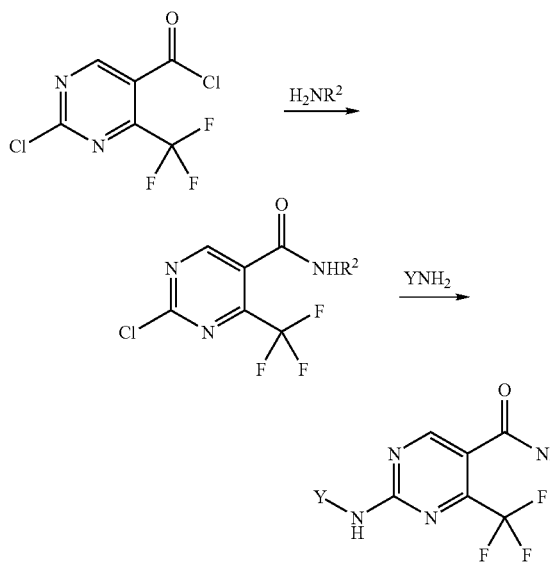

Preparation Method A: refers to the procedure give in part (b) of Example 166.

Preparation Method B: Exemplified by Example 154: A mixture of 2-chloro-4-trifluoromethyl-pyrimidin-5-carboxylic acid (tetrahydropyran-4-ylmethyl)-amide (50 mg), 3,5-dicyanoaniline (69 mg), and acetonitrile (0.5 ml) was irradiated in a microwave apparatus (the model used was the 'Creator', supplied by 'Personal Chemistry', operating at 300 Watts), at 180° C. for 60 min. The temperature, duration of irradiation, and number of equivalents of the substituted-aniline used are given after the method in the table.

Preparation Method C: exemplified by Example 162: A mixture of 2-chloro-4-trifluoromethyl-pyrimidin-5-carboxylic acid (tetrahydropyran-4-ylmethyl)-amide (80 mg) and 4-fluoro-2-(trifluoromethyl)aniline (111 mg) was irradiated in microwave apparatus (the model used was the 'Creator', supplied by 'Personal Chemistry', operating at 300 Watts), at 190° C. for 45 min.

Purification was carried out as detailed in the table to give the product.

Purification Method A: refers to the procedure give in part (b) of Example 166.

Purification Method B: mass directed autopurification using the procedures detailed at the beginning of the experimental.

Purification Method C: The reaction was worked up as for part (b) of Example 166, and the crude product further purified by Biotage chromatography over Merck 9385 silica gel, eluting with isohexane/ethyl acetate (7:3).

TABLE 6

| Ex. | Compound Name | Structure | Preparation Method | Purification method | LCMS 1 Retention time (min) 2 MH+ 3 Consistent Formula |
|---|---|---|---|---|---|
| 146 | 2-(3-Methoxy-5-trifluoromethyl-phenylamino)-4-trifluoromethyl-pyrimidine-5-carboxylic acid cyclohexylmethyl-amide | 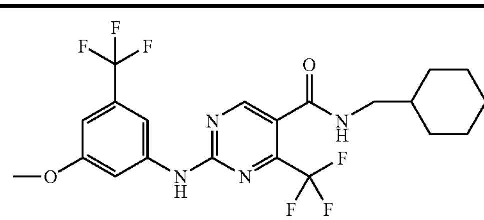 | A | B | 3.91 477 $C_{21}H_{22}F_6N_4O_2$ |
| 147 | 2-(4-Chloro-3-methyl-phenylamino)-4-trifluoromethyl-pyrimidine-5-carboxylic acid cyclohexylmethyl-amide | 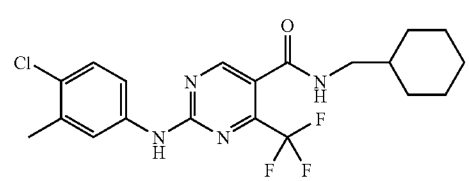 | A | B | 3.96 427 $C_{20}H_{22}{}^{35}ClF_3N_4O$ |
| 148 | 2-(3-Chloro-4-methyl-phenylamino)-4-trifluoromethyl-pyrimidine-5-carboxylic acid N-cyclohexylmethyl-amide | 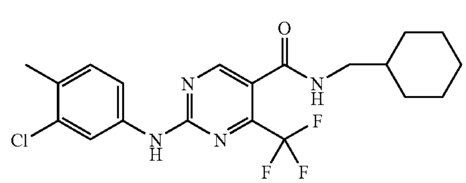 | A | B | 3.92 427 $C_{20}H_{22}{}^{35}ClF_3N_4O$ |
| 149 | 2-(4-Chloro-3-cyano-phenylamino)-4-trifluoromethyl-pyrimidine-5-carboxylic acid cyclohexylmethyl-amide | 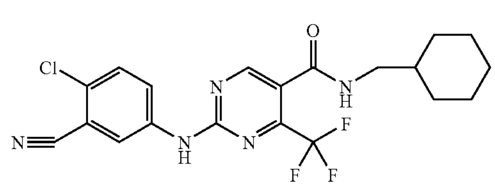 | A | B | 3.76 438 $C_{20}H_{19}{}^{35}ClF_3N_5O$ |

TABLE 6-continued

| Ex. | Compound Name | Structure | Preparation Method | Purification method | LCMS 1 Retention time (min) 2 MH+ 3 Consistent Formula |
|---|---|---|---|---|---|
| 150 | 2-(2-Chloro-5-methyl-phenylamino)-4-trifluoromethyl-pyrimidine-5-carboxylic acid cyclohexylmethyl-amide | 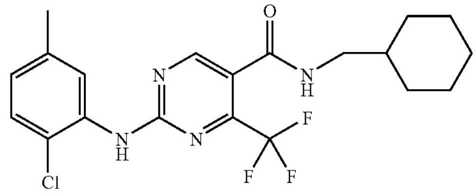 | A | B | 3.82<br>427<br>$C_{20}H_{22}{}^{35}ClF_3N_4O$ |
| 151 | 2(3-Chloro-2,6-dimethyl-phenylamino)-4-trifluoromethyl-pyrimidine-5-carboxylic acid cyclohexylmethyl-amide | 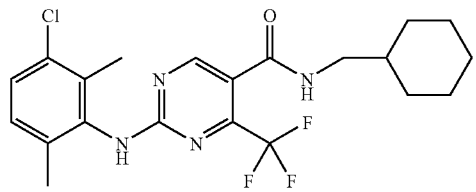 | A | B | 3.76<br>441<br>$C_{21}H_{24}{}^{35}ClF_3N_4O$ |
| 152 | 2-(3-Chloro-4-trifluoromethoxyphenyl-amino)-4-trifluoromethyl-pyrimidine-5-carboxylic acid cyclo-hexylmethyl-amide | 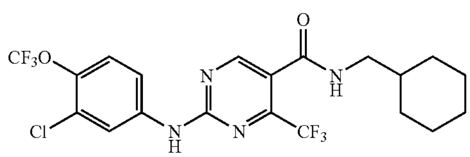 | A | A | 4.00<br>497<br>$C_{20}H_{19}{}^{35}ClF_6N_4O_2$ |
| 153 | 2-(3-Fluoro-4-trifluoromethylphenyl-amino)-4-trifluoromethyl-pyrimidine-5-carboxylic acid cyclo-hexylmethyl-amide | 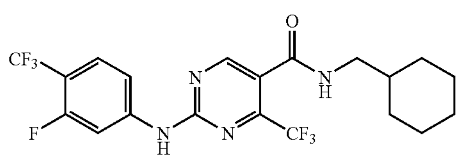 | A | C | 3.89<br>465<br>$C_{20}H_{19}F_7N_4O$ |
| 154 | 2-(3,5-Dicyano-phenylamino)-4-trifluoromethyl-pyrimidine-5-carboxylic acid (tetrahydropyran-4-ylmethyl)-amide | 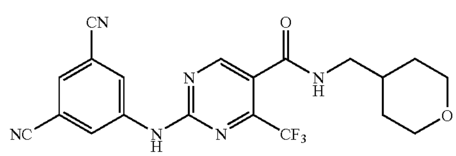 | B (180°, 60 mins, 3 equiv) | B | 3.01<br>431<br>$C_{20}H_{17}F_3N_6O_2$ |
| 155 | 2-(3-Chloro-2,6-di-methylphenylamino)-4-trifluoromethyl-pyrimidine-5-carboxylic acid (tetrahydro-pyran-4-ylmethyl)-amide | 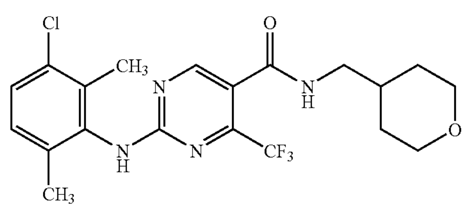 | A | B | 3.22<br>443<br>$C_{20}H_{22}{}^{35}ClF_3N_4O_2$ |
| 156 | 2-(2-Chloro-6-methyl-phenylamino)-4-tri-fluoromethyl-pyrimidine-5-carboxylic acid (tetrahydropyran-4-ylmethyl)-amide | 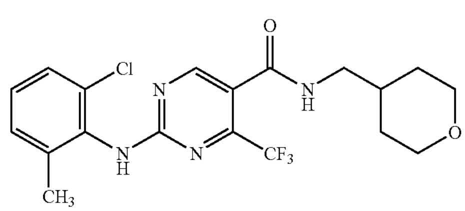 | B (180°, 60 mins, 5 equiv) | B | 3.05<br>429<br>$C_{19}H_{20}{}^{35}ClF_3N_4O_2$ |
| 157 | 2-(2-Chloro-3-methyl-phenylamino)-4-tri-fluoromethyl-pyrimidine-5-carboxylic acid (tetrahydropyran-4-ylmethyl)-amide | 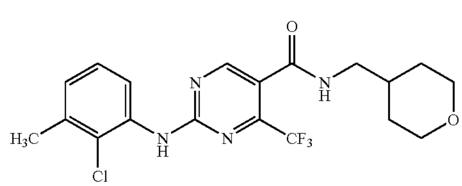 | A | B | 3.27<br>429<br>$C_{15}H_{20}{}^{35}ClF_3N_4O_2$ |

TABLE 6-continued

| Ex. | Compound Name | Structure | Preparation Method | Purification method | LCMS 1 Retention time (min) 2 MH+ 3 Consistent Formula |
|---|---|---|---|---|---|
| 158 | 2-(4-Chloro-2,6-dimethylphenylamino)-4-trifluoromethyl-pyrimidine-5-carboxylic acid (tetrahydropyran-4-ylmethyl)-amide | 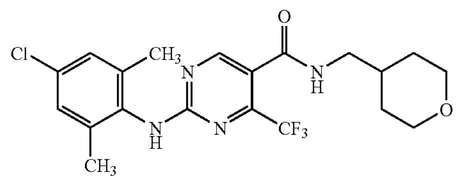 | A | B | 3.26<br>443<br>$C_{20}H_{22}{}^{35}ClF_3N_4O_2$ |
| 159 | 2-(5-Chloro-2-sulfamoylphenyl-amino)-4-amino)-4-trifluoromethyl-pyrimidine-5-carboxylic acid (tetrahydropyran-4-ylmethyl)-amide | 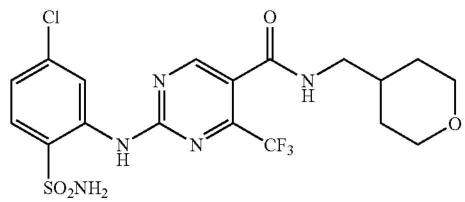 | B (180°, 60 mins, 5 equiv) | B | 3.08<br>494<br>$C_{18}H_{19}{}^{35}ClF_3N_5O_4S$ |
| 160 | 2-(2-Fluoro-4-trifluoromethylphenylamino)-4-trifluoromethyl-pyrimidine-5-carboxylic acid cyclobutylmethyl-amide | 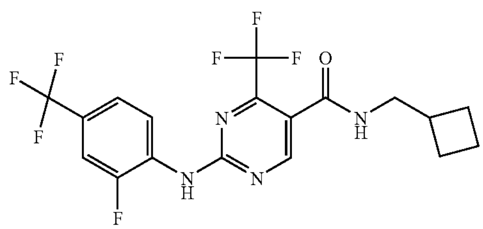 | A | A | 3.67<br>437<br>$C_{18}H_{15}F_7N_4O$ |
| 161 | 2-(2-Chloro-4-trifluoromethylphenylamino)-4-trifluoromethyl-pyrimidine-5-carboxylic acid cyclohexylmethyl-amide | 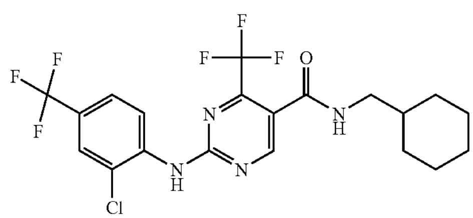 | A | B | 3.97<br>481<br>$C_{20}H_{19}{}^{35}ClF_6N_4O$ |
| 162 | 2-(2-Trifluoromethyl-4-fluorophenylamino)-4-trifluoromethyl-pyrimidine-5-carboxylic acid (tetrahydro-pyran-4-ylmethyl)amide | 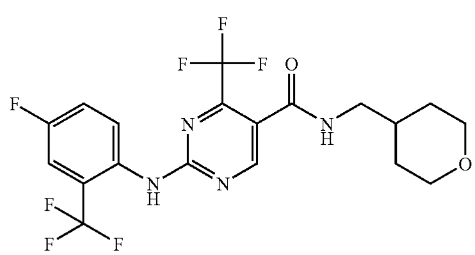 | C | B | 3.16<br>467<br>$C_{19}H_{17}N_4O_2F_7$ |
| 261 | 2-(2-Fluoro-4-trifluoromethylphenylamino)4-trifluoromethyl-pyrimidine-5-carboxylic acid (tetrahydropyran-4-ylmethyl)-amide | 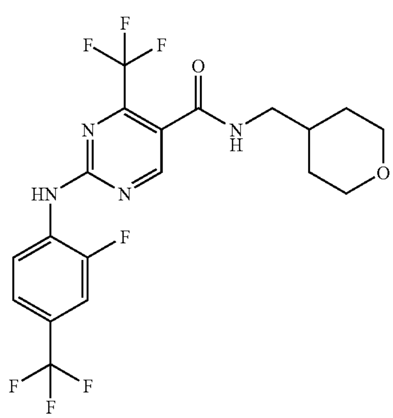 | B 180°, 2 × 42 min, 5 equivalents | B | 3.37<br>467<br>$C_{19}H_{17}F_7N_4O_2$ |

TABLE 6-continued

| Ex. | Compound Name | Structure | Preparation Method | Purification method | LCMS 1 Retention time (min) 2 MH+ 3 Consistent Formula |
|---|---|---|---|---|---|
| 262 | 2-(3,5-Bistrifluoromethylphenylamino)-4-trifluoromethyl-pyrimidine-5-carboxylic acid cyclobutylmethyl-amide | 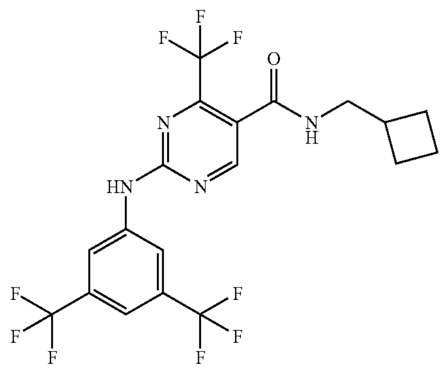 | B 180°, 30 min, 5 equivalents | B | Molecular ion observed [M − H]− 485 consistent with molecular formula $C_{19}H_{15}F_9N_4O$ |

EXAMPLE 163

2-(3-Methoxyphenylamino)-4-trifluoromethyl-pyrimidine-5-carboxylic acid cyclohexylmethyl-amide

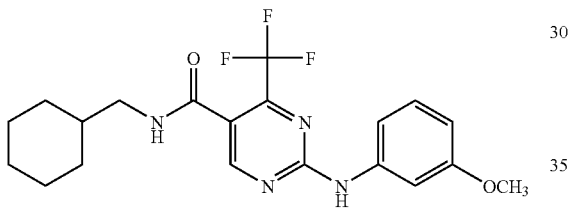

In a manner similar to Reference Example 1(c) 2-(3-methoxyphenylamino)-4-trifluoro-methylpyrimidine-5-carboxylic acid (32 mg) and cyclohexanemethanamine (16 µl, ex Lancaster) afforded the title compound (28 mg).

NMR (DMSO-d6) δ 0.85-1.0 (2H, m), 1.1-1.25 (3H, m), 1.5 (1H, m), 1.55-1.75 (5H, m), 3.06 (2H, t), 3.74 (3H, s), 6.63 (1H, d), 7.2-7.3 (2H, m), 7.54 (1H, s), 8.57 (1H, t), 8.74 (1H, s), 10.35 (1H, s).

LC/MS, t=3.57 min, Molecular ion observed [MH+]=409 consistent with the molecular formula $C_{20}H_{23}F_3N_4O_2$.

EXAMPLE 164

2-(3-Chlorophenylamino)-4-trifluoromethyl-pyrimidine-5-carboxylic acid (1-hydroxycyclohexylmethyl)-amide

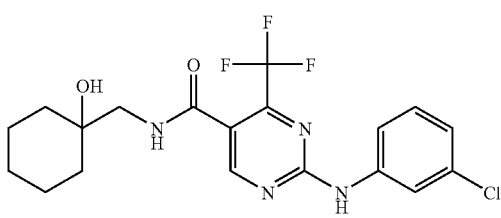

In a manner similar to Reference Example 1(c) 2-(3-chlorophenylamino)-4-trifluoro-methylpyrimidine-5-carboxylic acid (32 mg) and 1-aminomethyl-1-cyclohexanol hydrochloride (20 mg, ex Aldrich) afforded the title compound (29 mg).

NMR (DMSO-d6) δ 1.3 (1H, m), 1.4-1.5 (7H, m), 1.6 (2H, m), 3.28 (2H, d), 4.34 (1H, s), 7.16 (1H, d), 7.43 (1H, t), 7.73 (1H, d), 8.04 (1H, t), 8.51 (1H, t), 8.91 (1H, s), 10.65 (1H, s).

LC/MS, t=3.39 min, Molecular ion observed [M-H]−=427 consistent with the molecular formula $C_{19}H_{20}{}^{35}ClF_3N_4O_2$

EXAMPLE 165

2-(3-Bromophenylamino)-4-trifluoromethyl-pyrimidine-5-carboxylic acid (1-hydroxycyclohexylmethyl)-amide

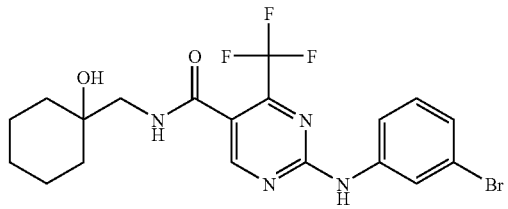

In a manner similar to Reference Example 1(c) 2-(3-bromophenylamino)-4-trifluoro-methylpyrimidine-5-carboxylic acid (36.5 mg) and 1-aminomethyl-1-cyclohexanol hydrochloride (20 mg, ex Aldrich) afforded the title compound (28 mg).

NMR (DMSO-d6) δ 1.25 (1H, m), 1.35-1.45 (7H, m), 1.6 (2H, m), 3.23 (2H, d), 4.28 (1H, s), 7.23 (1H, d), 7.31 (1H, t), 7.71 (1H, d), 8.12 (1H, s), 8.45 (1H, t), 8.85 (1H, s), 10.55 (1H, s).

LC/MS, t=3.43 min, Molecular ion observed [M-H]−=471 consistent with the molecular formula $C_{19}H_{20}{}^{79}BrF_3N_4O_2$.

EXAMPLE 166

2-(3 Chloro-4-fluorophenylamino)-4-trifluoromethyl-pyrimidine-5-carboxylic acid cyclohexylmethyl-amide (a). To a solution of 2-chloro-4-trifluoromethyl-pyrimidin-5-carbonyl chloride (750 mg, ex Maybridge) in dichloromethane (15 ml) at −400 was added dropwise over 30 minutes a solution of cyclohexanemethanamine (0.35 ml, ex Lancaster) and triethylamine (0.41 ml) in dichloromethane (15 ml). Dichloromethane was removed under reduced pressure and ethyl acetate (20 ml) added. The solution was washed sequentially with water, 5% sodium bicarbonate solution and water, dried (MgSO$_4$), evaporated and triturated with ether:hexane to afford 2-chloro-trifluoromethyl-pyrimidine-5-carboxylic acid cyclohexylmethyl-amide (666 mg).

NMR (DMSO-d6) δ 0.85-1.0 (2H, m), 1.1-1.25 (3H, m), 1.5 (1H, m), 1.55-1.75 (5H, m), 3.12 (2H, t), 8.75 (1H, t), 9.18 (1H, s).

LC/MS, t=3.31 min, Molecular ion observed [MH$^+$]=322 consistent with the molecular formula $C_{13}H_{15}{}^{35}ClF_3N_3O$.

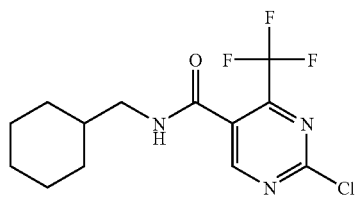

(b). To a solution of 2-chloro-4-trifluoromethyl-pyrimidine-5-carboxylic acid cyclohexylmethyl-amide (100 mg) in 1,4-dioxan (1 ml) was added 3-chloro-4-fluoroaniline (228 mg, ex Lancaster) and the solution stirred at reflux for 4 hours. Dioxan was removed under reduced pressure and ethyl acetate (5 ml) added. The solution was washed sequentially with 2N hydrochloric acid (2×3 ml) and water (3×3 ml), dried MgSO$_4$), evaporated and triturated with isohexane to afford the title compound (107 mg).

NMR (DMSO-d6) δ 0.85-1.0 (2H, m), 1.1-1.25 (3H, m), 1.45 (1H, m), 1.6-1.75 (5H, m), 3.06 (2H, t), 7.25 (1H, t), 7.43 (1H, t), 7.56 (1H, t), 8.56 (1H, t), 8.69 (1H, s), 10.20 (1H, s).

LC/MS, t=3.81 min, Molecular ion observed [MH$^+$]=431 consistent with the molecular formula $C_{19}H_{19}{}^{35}ClF_4N_4O$.

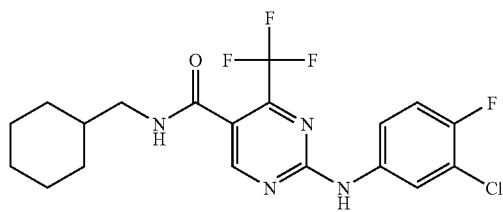

EXAMPLE 167

2-(3-Chloro-2-fluorophenylamino)-4-trifluoromethyl-pyrimidine-5-carboxylic acid cyclohexlmethyl-amide

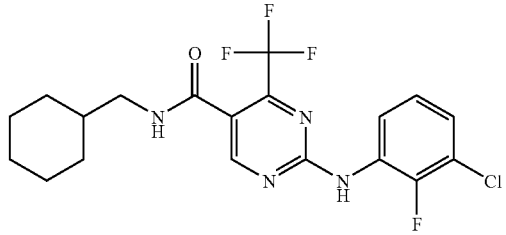

In a manner similar to Example 166(b), 2-chloro-4-trifluoromethyl-pyrimidine-5-carboxylic acid cyclohexylmethyl-amide (100 mg) and 3-chloro-2-fluoroaniline (230 mg, ex Acros) afforded the title compound (101 mg).

NMR (DMSO-d6) δ 0.85-1.0 (2H, m), 1.1-1.25 (3H, m), 1.5 (1H, m), 1.6-1.8 (5H, m), 3.08 (2H, t), 7.43 (1H, t), 7.67 (1H, m), 8.07 (1H, d), 8.58 (1H, t), 8.80 (1H, s), 10.60 (1H, s).

LC/MS, t=3.71 min, Molecular ion observed [MH$^+$]=431 consistent with the molecular formula $C_{19}H_{19}{}^{35}ClF_4N_4O$.

EXAMPLE 168

2-(5-Chloro-2-fluorophenylamino)-4-trifluoromethyl-pyrimidine-5-carboxylic acid cyclohexylmethyl-amide

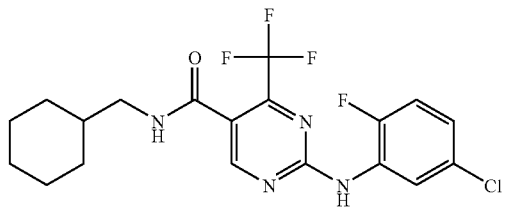

In a manner similar to Example 166(b), 2-chloro-4-trifluoromethyl-pyrimidine-5-carboxylic acid cyclohexylmethyl-amide (100 mg) and 5-chloro-2-fluoroaniline (230 mg, ex Avocado) afforded the title compound (116 mg).

NMR (DMSO-d6) δ 0.85-1.0 (2H, m), 1.1-1.25 (3H, m), 1.5 (1H, m), 1.6-1.75 (5H, m), 3.07 (2H, t), 7.29 (1H, m), 7.36 (1H, t), 7.77 (1H, d of d), 8.57 (1H, t), 8.72 (1H, s), 10.15 (1H, s).

LC/MS, t=3.73 min, Molecular ion observed [MH$^+$]=431 consistent with the molecular formula $C_{19}H_{19}{}^{35}ClF_4N_4O$.

EXAMPLE 169

2-(3,5-Difluorophenylamino)-4-trifluoromethyl-5-carboxylic acid cyclohexylmethyl-amide

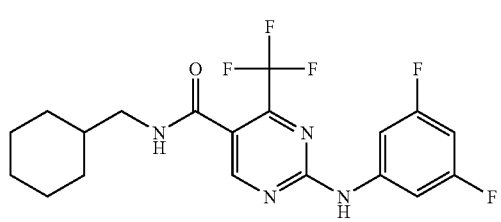

In a manner similar to Example 166(b) 2-chloro-4-trifluoromethyl-pyrimidine-5-carboxylic acid cyclohexylmethyl-amide (100 mg) and 3,5-difluoroaniline (200 mg, ex Lancaster) afforded the title compound (110 mg).

NMR (DMSO-d6) δ 0.85-1.0 (2H, m), 1.1-1.25 (3H, m), 1.5 (1H, m), 1.6-1.75 (5H, m), 3.09 (2H, t), 6.89 (1H, t), 7.54 (2H, d), 8.60 (1H, t), 8.85 (1H, s), 10.80 (1H, s).

LC/MS, t=3.74 min, Molecular ion observed [MH$^+$]=415 consistent with the molecular formula $C_{19}H_{19}F_5N_4O$.

EXAMPLE 170

2-(4-Chloro-2-trifluoromethylphenylamino)-4-trifluoromethyl-pyrimidine-5-carboxylic acid cyclohexylmethyl-amide

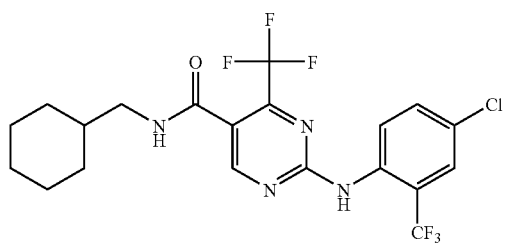

In a manner similar to Example 166(b) 2-chloro-4-trifluoromethyl-pyrimidine-5-carboxylic acid cyclohexylmethyl-amide (80 mg) and 4-chloro-2-trifluoromethylaniline (107 mg, ex Lancaster) afforded, after purification by mass-directed autopreparation technique, the title compound (6 mg).

NMR (DMSO-d6) δ 0.85-1.0 (2H, m), 1.1-1.25 (3H, m), 1.5 (1H, m), 1.55-1.75 (5H, m), 3.06 (2H, t), 7.76 (1H, d), 7.88 (1H, d), 7.97 (1H, s), 8.56 (1H, t), 8.70 (1H, s), 10.15 (1H, s).

LC/MS, t=3.97 min, Molecular ion observed [MH$^+$]=481 consistent with the molecular formula $C_{20}H_{19}{}^{35}ClF_6N_4O$.

EXAMPLE 171

2-(3-Cyanophenylamino)-4-trifluoromethyl-pyrimidine-5-carboxylic acid cyclohexylmethyl-amide

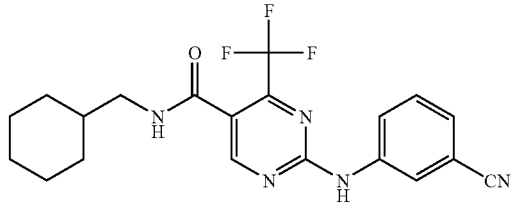

To a solution of 2-chloro-4-trifluoromethyl-pyrimidine-5-carboxylic acid cyclohexylmethyl-amide (50 mg) in acetonitrile (0.5 ml) was added 3-aminobenzonitrile (92 mg, ex Aldrich) and the solution heated at 200° C. under microwave conditions for 45 minutes. Acetonitrile was removed under reduced pressure and ethyl acetate (5 ml) added. The solution was washed sequentially with 2N hydrochloric acid (2×3 ml) and water (3×3 ml), dried (MgSO$_4$), evaporated and the residue purified using silica gel chromatography with 1:1 ethyl acetate:isohexane to afford the title compound (37 mg).

NMR (DMSO-d6) δ 0.85-1.0 (2H, m), 1.1-1.25 (3H, m), 1.5 (1H, m), 1.6-1.8 (5H, m), 3.08 (2H, t), 7.50 (1H, d), 7.57 (1H, t), 8.00 (1H, d), 8.25 (1H, s), 8.59 (1H, t), 8.83 (1H, s), 10.75 (1H, s).

LC/MS, t=3.51 min, Molecular ion observed [MH$^+$]=404 consistent with the molecular formula $C_{20}H_{20}F_3N_5O$.

EXAMPLE 172

2-(3-Cyanophenylamino)-4-trifluoromethyl-pyrimidine-5-carboxylic acid (tetrahydropyran-4-ylmethyl)-amide

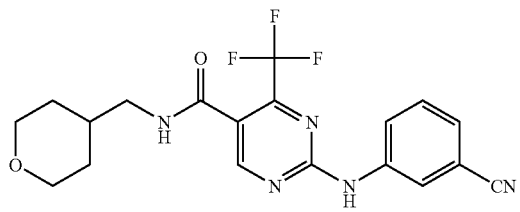

In a manner similar to Reference Example 1(c) 2-(3-cyanophenylamino)-4-trifluoro-methylpyrimidine-5-carboxylic acid (32 mg) and 4-aminomethyltetrahydropyran (14 mg, ex Combi Blocks) afforded the title compound (26 mg).

NMR (DMSO-d6) δ 1.15-1.25 (2H, m), 1.62 (2H, d), 1.74 (1H, m), 3.14 (2H, t), 3.27 (2H, t), 3.86 (2H, d of d), 7.50 (1H, d), 7.57 (1H, t), 8.00 (1H,d), 8.26 (1H, s), 8.65 (1H, t), 8.85 (1H, s), 10.70 (1H, s).

LC/MS, t=2.94 min, Molecular ion observed [MH$^+$] 406 consistent with the molecular formula $C_{19}H_{18}F_3N_5O_2$.

EXAMPLE 173

2-(3-Cyanophenylamino)-4-trifluoromethyl-pyrimidine-5-carboxylic acid cyclopentylmethyl-amide

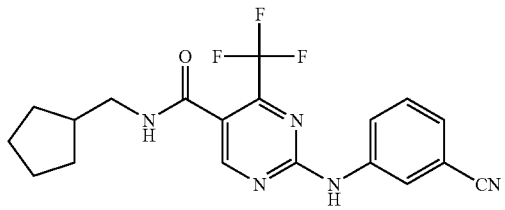

In a manner similar to Reference Example 1(c) 2-(3-cyanophenylamino)-4-trifluoro-methylpyrimidine-5-carboxylic acid (32 mg) and cyclopentanemethanamine hydrochloride (17 mg) afforded the title compound (16 mg).

NMR (DMSO-d6) δ 1.20-1.30 (2H, m), 1.45-1.6 (4H, m), 1.65-1.75 (2H, m), 2.08 (1H, quintuplet), 3.19 (2H, t), 7.50 (1H, d), 7.57 (1H, t), 8.00 (1H, d), 8.25 (1H, s), 8.63 (1H, t), 8.82 (1H, s), 10.70 (1H, s).

LC/MS, t=3.42 min, Molecular ion observed [MH$^+$]=390 consistent with the molecular formula $C_{19}H_{18}F_3N_5O$.

EXAMPLE 174

2-(4-Cyanophenylamino)-4-trifluoromethyl-pyrimidine-5-carboxylic acid cyclohexylmethyl-amide

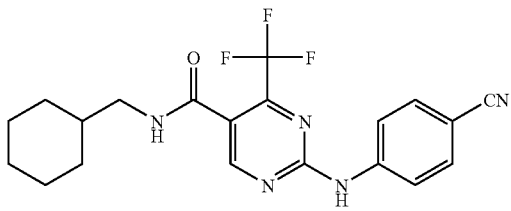

In a manner similar to Reference Example 1(c) 2-(4-cyanophenylamino)-4-trifluoro-methylpyrimidine-5-carboxylic acid (32 mg) and cyclohexanemethanamine (16 µl, ex Lancaster) afforded the title compound (18 mg).

NMR (DMSO-d6) δ 0.85-1.0 (2H, m), 1.1-1.25 (3H, m), 1.5 (1H, m), 1.6-1.8 (5H, m), 3.08 (2H, t), 7.81 (2H, d), 7.97 (2H, d), 8.61 (1H, t), 8.85 (1H, s), 10.90 (1H, s).

LC/MS, t=3.51 min, Molecular ion observed [MH$^+$]=404 consistent with the molecular formula $C_{20}H_{20}F_3N_5O$.

EXAMPLE 175

2-(4-Cyanophenylamino)-4-trifluoromethyl-pyrimidine-5-carboxylic acid (tetrahydropyran-4-ylmethyl)-amide

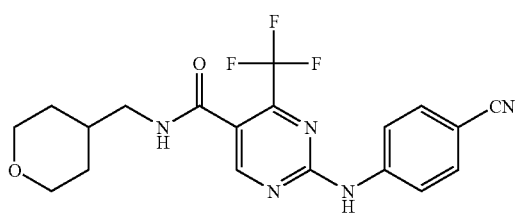

In a manner similar to Reference Example 1(c) 2-(4-cyanophenylamino)-4-trifluoro-methylpyrimidine-5-carboxylic acid (32 mg) and 4-aminomethyltetrahydropyran (14 mg, ex Combi Blocks) afforded the title compound (6 mg).

NMR (DMSO-d6) δ 1.15-1.25 (2H, m), 1.60 (2H, d), 1.75 (1H, m), 3.14 (2H, t), 3.27 (2H, t), 3.86 (2H, d), 7.82 (2H, d), 7.97 (2H, d), 8.67 (1H, t), 8.87 (1H, s), 10.85 (1H, s).

LC/MS, t=2.92 min, Molecular ion observed [MH$^+$] 406 consistent with the molecular formula $C_{19}H_{19}F_3N_5O_2$.

EXAMPLE 176

2-(4-Cyanophenylamino)-4-trifluoromethyl-pyrimidine-5-carboxylic acid cyclopentylmethyl-amide

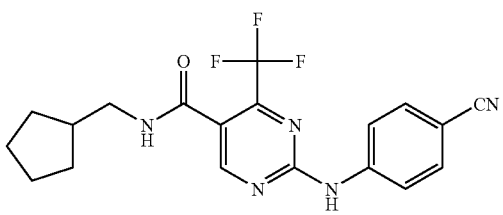

In a manner similar to Reference Example 1(c) 2-(4-cyanophenylamino)-4-trifluoro-methylpyrimidine-5-carboxylic acid (32 mg) and cyclopentanemethanamine hydrochloride (17 mg) afforded the title compound (22.5 mg).

NMR (DMSO-d6) δ 1.15-1.30 (2H, m), 1.45-1.65 (4H, m), 1.65-1.75 (2H, m), 2.08 (1H, quintuplet), 3.17 (2H, t), 7.82 (2H, d), 7.97 (2H, d), 8.64 (1H, t), 8.84 (1H, s), 10.90 (1H, s).

LC/MS, t=3.40 min, Molecular ion observed [MH$^+$]=390 consistent with the molecular formula $C_{19}H_{18}F_3N_5O$.

EXAMPLE 177

2-(3-Methoxy-5-(trifluoromethyl)phenylamino)-4-trifluoromethyl-pyrimidine-5-carboxylic acid (tetrahydropyran-4-ylmethyl)-amide (a). To a solution of 2-chloro-4-trifluoromethyl-pyrimidin-5-carbonyl chloride (1.5 g) in dichloromethane (20 ml) at −20 was added a dropwise a solution of 4-aminomethyltetrahydropyran (0.70 g, ex Combi Blocks) and triethylamine (1.05 ml) in dichloromethane (10 ml) and the solution stirred at 0° for 1 hour. Dichloromethane was removed under reduced pressure and ethyl acetate (30 ml) added. The solution was washed with 2N hydrochloric acid (3×20 ml), dried (MgSO$_4$), evaporated and the residue purified using silica gel chromatography with 1:1 ethyl acetate:isohexane to afford 2-chloro-4-trifluoromethyl-pyrimidin-5-carboxylic acid (tetrahydropyran-4-yl-methyl)-amide (1.20 g).

NMR (DMSO-d6) δ 1.15-1.3 (2H, m), 1.61 (2H, d), 1.74 (1H, m), 3.17 (2H, t), 3.25 (2H, t), 3.86 (2H, d of d), 8.81 (1H, t), 9.20 (1H, s).

LC/MS, t=2.54 min, Molecular ion observed [MH$^+$]=324 consistent with the molecular formula $C_{12}H_{13}^{35}ClF_3N_3O_2$.

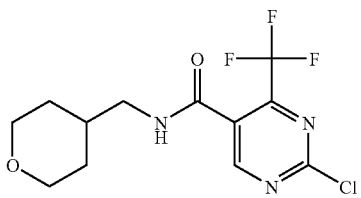

(b). In a manner similar to Example 166(b), 2-chloro-4-trifluoromethyl-pyrimidin-5-carboxylic acid (tetrahydropyran-4-ylmethyl)-amide (50 mg) and 3-methoxy-5-(trifluoromethyl)aniline (148 mg, ex Aldrich) afforded after stirring at reflux for 24 hours the title compound (51 mg).

NMR (DMSO-d6)δ 1.15-1.3 (2H, m), 1.62 (2H, d), 1.74 (1H, m), 3.13 (2H, t), 3.27 (2H, t), 3.83 (3H, s), 3.86 (2H, d), 6.92 (1H, s), 7.73 (1H, s), 7.80 (1H,s), 8.64 (1H, t), 8.85 (1H, s), 10.65 (1H, s).

LC/MS, t=3.38 min, Molecular ion observed [MH$^+$]=479 consistent with the molecular formula $C_{20}H_{20}F_6N_4O_3$.

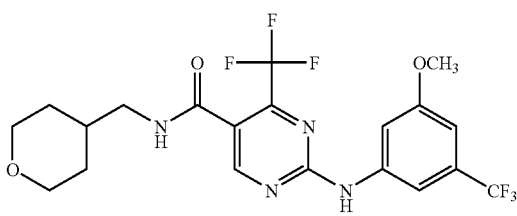

EXAMPLE 178

2-(3,5-Bis-trifluoromethylphenylamino)-4-trifluoromethyl-pyrimidine-5-carboxylic acid(tetrahydropyran-4-ylmethyl)-amide In a manner similar to Example 166(b) 2-chloro-4-trifluoromethyl-pyrimidin-5-carboxylic acid (tetrahydropyran-4-ylmethyl)-amide (50 mg) and 3,5-bis(trifluoromethyl)aniline (177 mg, ex Aldrich) afforded, after stirring at reflux for 80 hours and purification by mass-directed autopreparation technique, the title compound (24.5 mg).

NMR (DMSO-d6) δ 1.15-1.3 (2H, m), 1.62 (2H, d), 1.75 (1H, m), 3.14 (2H, t), 3.28 (2H, t), 3.86 (2H, d), 7.72 (1H, s), 8.49 (2H, s), 8.67 (1H, t), 8.93 (1H, s), 11.05 (1H, s).

LC/MS, t=3.62 min, Molecular ion observed [MH$^+$]=517 consistent with the molecular formula $C_{20}H_{17}F_9N_4O_2$.

EXAMPLE 179

2-(3-Bromo-5-(trifluoromethyl)phenylamino)-4-trifluoromethyl-pyrimidine-5-carboxylic acid (tetrahydropyran-4-methyl)-amide

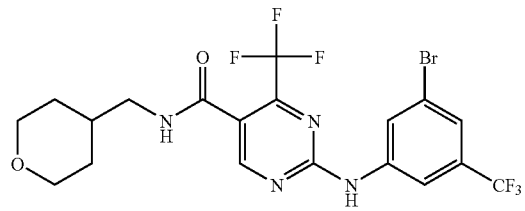

In a manner similar to Example 166(b) 2-chloro-4-trifluoromethyl-pyrimidin-5-carboxylic acid (tetrahydropyran-4-ylmethyl)-amide (50 mg) and 3-bromo-5-(trifluoro-methyl)aniline (185 mg, ex Avocado) afforded, after stirring at reflux for 80 hours and purification by mass-directed autopreparation technique, the title compound (28 mg).

NMR (DMSO-d6) δ 1.15-1.3 (2H, m), 1.62 (2H, d), 1.74 (1H, m), 3.14 (2H, t), 3.28 (2H, t), 3.86 (2H, d), 7.60 (1H, s), 8.24 (1H, s), 8.29 (1H, s), 8.66 (1H, t), 8.99 (1H, s), 10.90 (1H, s).

LC/MS, t=3.63 min, Molecular ion observed [M-H]$^-$=527 consistent with the molecular formula $C_{19}H_{17}^{79}BrF_6N_4O_2$.

EXAMPLE 180

2-(3-Fluoro-5-(trifluoromethyl)phenylamino)-4-trifluoromethyl-pyrimidine-5-carboxylic acid (tetrahydropyran-4-ylmethyl)-amide

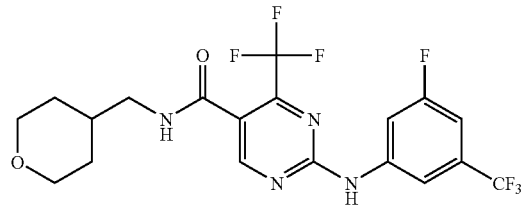

In a manner similar to Example 166(b) 2-chloro-4-trifluoromethyl-pyrimidin-5-carboxylic acid (tetrahydropyran-4-ylmethyl)-amide (50 mg) and 3-fluoro-5-trifluoromethyl) aniline (138 mg, ex Fluorochem) afforded after stirring at reflux for 24 hours the title compound (44 mg).

NMR (DMSO-d6) δ 1.15-1.3 (2H, m), 1.62 (2H, d), 1.75 (1H, m), 3.14 (2H, t), 3.28 (2H, t), 3.86 (2H, d), 7.32 (1H, d), 7.96 (1H, d), 8.06 (1H, s), 8.67 (1H, t), 8.90 (1H, s), 10.90 (1H, s).

LC/MS, t=3.45 min, Molecular ion observed [MH$^+$]=467 consistent with the molecular formula $C_{19}H_{17}F_7N_4O_2$.

EXAMPLE 181

2-(2-Fluoro-3-(trifluoromethyl)phenylamino)-4-trifluoromethyl-pyrimidine-5-carboxylic acid (tetrahydropyran-4-ylmethyl)-amide

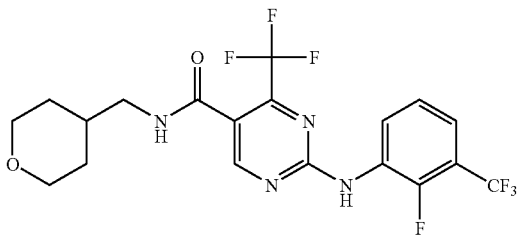

In a manner similar to Example 166(b) 2-chloro-4-trifluoromethyl-pyrimidin-5-carboxylic acid (tetrahydropyran-4-ylmethyl)-amide (50 mg) and 2-fluoro-3-(trifluoromethyl) aniline (138 mg, ex Aldrich) afforded, after stirring at reflux for 80 hours and purification by mass-directed autopreparation technique, the title compound (15 mg).

NMR (DMSO-d6) δ 1.1-1.25 (2H, m), 1.60 (2H, d), 1.73 (1H, m), 3.11 (2H, t), 3.26 (2H, t), 3.85 (2H, d), 7.43 (1H, t), 7.61 (1H, t), 7.92 (1H, s), 8.63 (1H, t), 8.72 (1H, s), 10.30 (1H, s).

LC/MS, t=3.28 min, Molecular ion observed [MH+]=467 consistent with the molecular formula $C_{19}H_{17}F_7N_4O_2$.

EXAMPLE 182

2-(2-Methylthio-3-(trifluoromethyl)phenylamino)-4-trifluoromethyl-pyrimidine-5-carboxylic acid (tetrahydropyran-4-ylmethyl)-amide

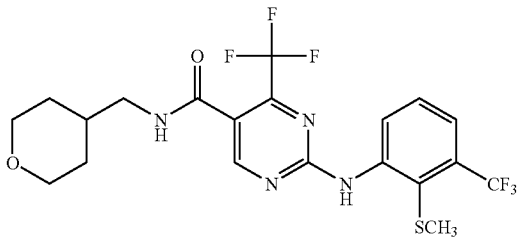

2-Chloro-4-trifluoromethyl-pyrimidin-5-carboxylic acid (tetrahydropyran-4-ylmethyl)-amide (50 mg), 2-methylthio-3-(trifluoromethyl)aniline (125 mg, ex Maybridge) and acetonitrile (0.5 ml) were heated at 190° under microwave irradiation for 30 minutes. The solvent was evaporated in vacuo and the residue purified by mass-directed autopreparation technique, to give the title compound (11 mg).

NMR (DMSO-d6) δ 1.1-1.25 (2H, m), 1.60 (2H, d), 1.73 (1H, m), 2.24 (3H, s), 3.12 (2H, t), 3.26 (2H, t), 3.85 (2H, d), 7.65 (2H, d), 8.11 (1H, t), 8.64 (1H, t), 8.72 (1H, s), 9.81 (1H, s).

LC/MS, t=3.53 min, Molecular ion observed [MH+]=495 consistent with the molecular formula $C_{20}H_{20}F_5N_4O_2S$.

EXAMPLE 183

2-(5-Chloro-2-methylphenylamino)-4-trifluoromethyl-pyrimidine-5-carboxylic acid (cyclopentylmethyl)-amide (a). To a solution of 2-chloro-4-trifluoromethyl-pyrimidin-5-carbonyl chloride (1.0 g, ex Maybridge) in dichloromethane (7 ml) at −2° was added a dropwise a solution of cyclopentanemethanamine hydrochloride (0.55 g) and triethylamine (1.4 ml) in dichloromethane (13 ml) and the solution stirred at 0° for 1 hour. Dichloromethane was removed under reduced pressure and ethyl acetate (20 ml) added. The solution was washed with 2N hydrochloric acid (3×15 ml), dried (MgSO4), evaporated and triturated with isohexane to afford 2-chloro trifluoromethyl-pyrimidin-5-carboxylic acid (cyclopentylmethyl)-amide (838 mg).

NMR (DMSO-d6) δ 1.1-1.3 (2H, m), 1.45-1.65 (4H, m), 1.65-1.8 (2H, m), 2.07 (1H, quintuplet), 3.20 (2H, t), 8.78 (1H, t), 9.17 (1H, s).

LC/MS, t=3.22 min, Molecular ion observed [M-H]−=306 consistent with the molecular formula $C_{12}H_{13}{}^{35}ClF_3N_3O$.

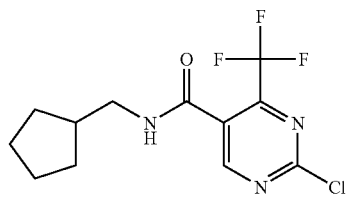

(b). In a manner similar to Example 166(b) 2-chloro-4-trifluoromethyl-pyrimidine-5-carboxylic acid cyclopentylmethylamide (47.5 mg) and 5-chloro-2-methylaniline (110 mg, ex Aldrich) afforded after stirring at reflux for 30 hours the title compound (41 mg).

NMR (DMSO-d6) δ 1.15-1.3 (2H, m), 1.4-1.6 (4H, m), 1.65-1.75 (2H, m), 2.06 (1H, quintuplet), 2.20 (3H, s), 3.14 (2H, t), 7.19 (1H, d), 7.29 (1H, d), 7.48 (1H, s), 8.55 (1H, t), 8.63 (1H, s), 9.83 (1H, s).

LC/MS, t=3.68 min, Molecular ion observed [MH+]=413 consistent with the molecular formula $C_{19}H_{20}{}^{35}ClF_3N_4O$.

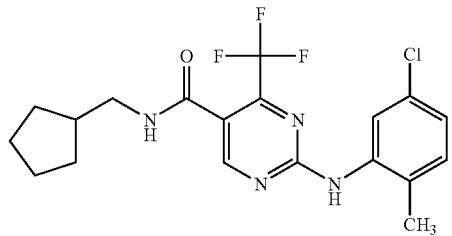

EXAMPLE 184

2-(3-Chloro-4-methylphenylamino)-4-trifluoromethyl-pyrimidine-5-carboxylic acid (tetrahydropyran-4-ylmethyl)-amide

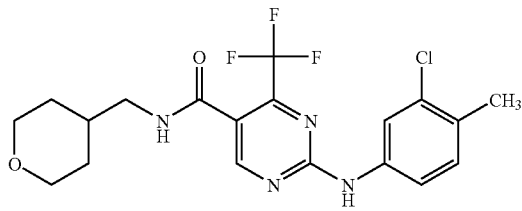

In a manner similar to Example 166(b) 2-chloro-trifluoromethyl-pyrimidine-5-carboxylic acid (tetrahydropyran-4-ylmethyl)-amide (50 mg) and 3-chloro-4-methyl-aniline (109 mg) afforded, after stirring at reflux for 24 hours and purification by mass-directed autopreparation technique, the title compound (35 mg).

NMR (DMSO-d6) δ 1.15-1.3 (2H, m), 1.61 (2H, d), 1.74 (1H, m), 2.28 (3H, s), 3.13 (2H, t), 3.27 (2H, t), 3.86 (2H, d of d), 7.31 (1H, d), 7.56 (1H, d), 7.94 (1H, s), 8.61 (1H, t), 8.79 (1H, s), 10.50 (1H, s).

LC/MS, Molecular ion observed [MH$^+$]=429 consistent with the molecular formula $C_{19}H_{20}{}^{35}ClF_3N_4O_2$.

EXAMPLE 185

2-(3-Chloro-2-methylphenylamino-4-trifluoromethyl-pyrimidine-5-carboxylic acid (tetrahydropyran-4-ylmethyl)-amide

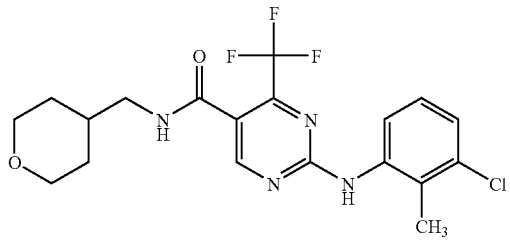

In a manner similar to Example 166(b) 2-chloro-4-trifluoromethyl-pyrimidine-5-carboxylic acid (tetrahydropyran-4-ylmethyl)-amide (50 mg) and 3-chloro-2-methyl-aniline (109 mg, known compound CAS No 87-60-5) afforded, after stirring at reflux for 24 hours and purification by mass-directed autopreparation technique, the title compound (30 mg).

NMR (DMSO-d6) δ 1.1-1.25 (2H, m), 1.59 (2H, d), 1.72 (1H, m), 2.21 (3H, s), 3.10 (2H, t), 3.26 (2H, t), 3.84 (2H, d of d), 7.24 (1H, t), 7.3 (2H, m), 8.56 (1H, t), 8.61 (1H, s), 9.99 (1H, s).

LC/MS, t=3.19 min, Molecular ion observed [MH$^+$]=429 consistent with the molecular formula $C_{19}H_{20}{}^{35}ClF_3N_4O_2$.

EXAMPLE 186

2-(4-Chloro-3-methoxyphenylamino)-4-trifluoromethyl-pyrimidine-5-carboxylic acid (tetrahydropyran-4-ylmethyl)-amide

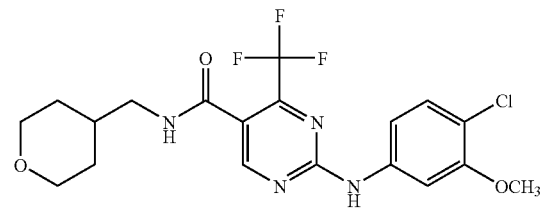

In a manner similar to Example 166(b) 2-chloro-4-trifluoromethyl-pyrimidine-5-carboxylic acid (tetrahydropyran-4-ylmethyl)-amide (50 mg) and 4-chloro-3-methoxy-aniline (122 mg) afforded, after stirring at reflux for 24 hours and purification by mass-directed autopreparation technique, the title compound (33 mg).

NMR (DMSO-d6) δ 1.1-1.25 (2H, m), 1.61 (2H, d), 1.73 (1H, m), 3.13 (2H, t), 3.27 (2H, t), 3.83 (3H, s), 3.86 (2H, d), 7.27 (1H, d), 7.37 (1H, d), 7.81 (1H, s), 8.63 (1H, t), 8.80 (1H, s), 10.50 (1H, s).

LC/MS, t=3.26 min, Molecular ion observed [MH$^+$]=445 consistent with the molecular formula $C_{19}H_{20}{}^{35}ClF_3N_4O_3$.

EXAMPLE 187

2-(4-Chloro-3-methylphenylamino)-4-trifluoromethyl-pyrimidine-5-carboxylic acid (tetrahydropyran-4-ylmethyl)-amide

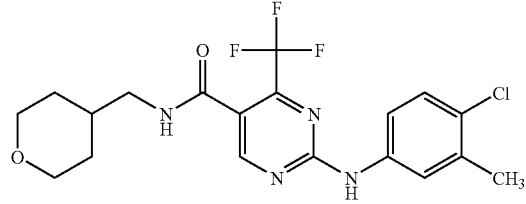

In a manner similar to Example 166(b) 2-chloro-4-trifluoromethyl-pyrimidine-5-carboxylic acid (tetrahydropyran-4-ylmethyl)-amide (50 mg) and 4-chloro-3-methyl-aniline (109 mg, ex Lancaster) afforded, after stirring at reflux for 24 hours and purification by mass-directed autopreparation technique, the title compound (33 mg).

NMR (DMSO-d6) δ 1.15-1.3 (2H, m), 1.61 (2H, d), 1.73 (1H, m), 2.31 (3H, s), 3.12 (2H, t), 3.27 (2H, t), 3.86 (2H, d), 7.37 (1H, d), 7.62 (1H, d), 7.72 (1H, s), 8.61 (1H, t), 8.77 (1H, s), 10.45 (1H, s).

LC/MS, t=3.41 min, Molecular ion observed [MH$^+$]=429 consistent with the molecular formula $C_{19}H_{20}{}^{35}ClF_3N_4O_2$.

EXAMPLE 188

2-(3-Chlorophenylamino)-4-trifluoromethyl-pyrimidine-5-carboxylic acid cyclobutylmethyl-methyl-amide a) N-Cyclobutylmethyl-2,2,2-trifluoroacetamide

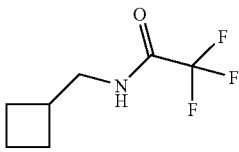

C-cyclobutyl-methylamine hydrochloride (1.82 g) was added to a solution of N,N-diisopropylethylamine (4.14 g) in dry tetrahydrofuran (30 ml) at 0° C. The mixture was stirred at 0° C. for 5 mins then cooled to −20° C. A solution of trifluoroacetic anhydride (3.57 g) in tetrahydrofuran (10 ml) was added dropwise over 10 mins and the mixture was then allowed to stir at room temperature for 1 hour. The solution was diluted with ether (100 ml) and water (75 ml), separated and the organic layer washed with water, dilute hydrochloric acid, water and brine, dried (MgSO$_4$) and evaporated to give the title compound (2.63 g)

NMR (CDCl$_3$) δ 1.70 (2H, m excess), 1.93 (2H, m), 2.10 (2H, m), 2.53 (1H, m), 3.39 (2H, t), 6.2 (1H, br s).

b) N-(Cyclobutylmethyl)-N-methylamine

N-Cyclobutylmethyl)-2,2,2-trifluoroacetamide (2.62 g) and iodomethane (3.6 ml) were dissolved in dry acetone (75 ml). Powdered potassium hydroxide (3.2 g) was added and the mixture heated at reflux for 5 mins. The excess iodomethane and acetone were removed under reduced pressure, water (75 ml) added and the solution heated at reflux for 1 hour. The mixture was cooled and ether (75 ml) added. The layers were separated and the organic layer was extracted with dilute hydrochloric acid (75 ml). The aqueous extract was washed with ether, then made strongly basic with sodium hydroxide and extracted with ether (2×75 ml). The extracts were dried (K$_2$CO$_3$) and evaporated to give the title compound (517 mg)

NMR (CDCl$_3$) δ 1.3 (1H, m excess), 1.65 (2H, m), 1.9 (2H, m), 2.05 (2H, m), 2.45 (4H, m), 2.55 (2H, d).

c) 2-(3-Chlorophenylamino)-4-trifluoromethyl-pyrimidine-5 boxylic acid cyclobutylmethyl-methyl-amide

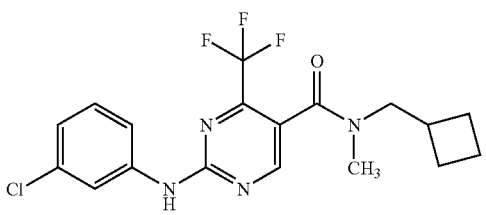

To a solution of N-(cyclobutylmethyl)-N-methylamine (17 mg) in dimethylformamide (1.5 ml) was added successively, 2-(3-chlorophenylamino)-4-trifluoromethyl-pyrimidine-5-carboxylic acid (35 mg), N,N-diisopropylethylamine (38 ul), 1-hydroxybenzotriazole hydrate (23 mg) and 1-(3-dimethylamino-propyl)-3-ethylcarbodiimide hydrochloride (25 mg). The solution was stirred overnight. Dimethylformamide was removed under reduced pressure and ethyl acetate (10 ml) added. The solution was washed sequentially with 10 ml portions of water, saturated sodium bicarbonate solution, water, dilute hydrochloric acid, water and brine, dried (MgSO$_4$) and evaporated to give the title compound (31 mg).

NMR (DMSO-d6) Rotamers in 60:40 ratio δ 1.5-2.1 (6H, m), 2.50 (0.4H, m-excess), 2.65 (0.6H, m), 2.84 (1.8H, s), 2.94 (1.2H, s), 3.22 (0.4H, d), 3.50 (1.6H, br s), 7.09 (1H, d), 7.36 (1H, m), 7.66 (1H, m), 7.96 (1H, s), 8.76 (1H, d), 10.5 (1H, s).

LC/MS t=3.66 min, Molecular ion observed (MH$^+$)=399 consistent with the molecular formula C$_{18}$H$_{18}$$^{35}$ClF$_3$N$_4$O

EXAMPLE 189

2-(3-Chlorophenylamino)-4-trifluoromethyl-pyrimidine-5-carboxylic acid cyclohexylmethyl-methyl-amide a) N-(Cyclohexylmethyl)-2,2,2-trifluoroacetamide

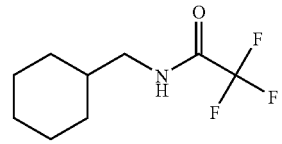

In a manner similar to Example 188a) cyclohexanemethanamine (2.83 g) (Lancaster) gave the title compound (5.09 g).

NMR (CDCl$_3$) δ 0.95 (2H, m), 1.22 (3H, m), 1.54 (1H, m excess), 1.70 (5H, m), 3.21 (2H, t), 6.3 (1H, br s).

b) N-(Cyclohexylmethyl)-N-methylamine

In a manner similar to Example 188b) N-(cyclohexylmethyl)-2,2,2-trifluoroacetamide (2.98 g) gave the title compound (1.41 g).

NMR (CDCl$_3$) δ 0.9 (2H, m), 1.23 (4H, m), 1.46 (1H, m excess), 1.72 (5H, m), 2.4 (5H, m).

c) 2-(3-Chlorophenylamino)-4-trifluoromethyl-pyrimidine-5-carboxylic acid cyclohexylmethyl-methyl-amide In a manner similar to Example 188c) 2-(3-chlorophenylamino)-4-trifluoromethyl-pyrimidine-5-carboxylic acid (35 mg) and N-(cyclohexylmethyl)-N-methylamine (21 mg) gave the title compound.

NMR (DMSO-d6) Rotamers in 63:37 ratio δ 0.65-1.30 (5H, m), 1.5-1.8 (6H, m), 2.87 (1.9H, s), 2.97 (1.1H, s), 3.03 (0.7H, d), 3.30 (1.3H, d excess), 7.09 (1H, d), 7.36 (1H, m), 7.66 (1H, d), 7.96 (1H, m), 8.73 (0.37H H, s), 8.78 (0.63H, s), 10.6 (1H, s).

LC/MS t=3.87 min, Molecular ion observed (MH$^+$)=427 consistent with the molecular formula C$_{20}$H$_{22}$$^{35}$ClF$_3$N$_4$O

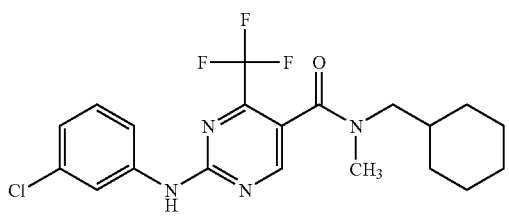

EXAMPLE 190

2-(3-Chlorophenylamino)-4-trifluoromethyl-pyridine-5-carboxylic acid cyclopentylmethyl-methyl-amide a) N-(Cyclopentylmethyl)-2,2,2-trifluoroacetamide

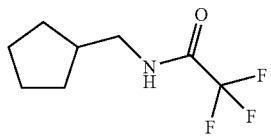

In a manner similar to Example 188a) (cyclopentylmethyl) amine (1.02 g) (Example 2) gave the title compound (1.47 g).

NMR (CDCl$_3$) δ 1.21 (2H, m), 1.4 (4H, m), 1.78 (2H, m), 2.10 (1H,m), 3.31 (2H, t), 6.3 (1H, br s).

b) N-(Cyclopentylmethyl)-N-methylamine hydrochloride

In a manner similar to Example 188b) N-cyclopentylmethyl)-2,2,2-trifluoroacetamide (1.46 g) gave, after treatment with hydrogen chloride in 1,4-dioxan, the title compound (0.77 g).

NMR (D$_2$O) δ 1.12 (2H, m), 1.5 (4H, m), 1.75 (2H, m), 2.08 (1H, m), 2.61 (3H, s), 2.90 (2H, d).

c) 2-(3-Chlorophenylamino)-4-trifluoromethyl-pyrimidine-5-carboxylic acid cyclopentylmethyl-methyl-amide

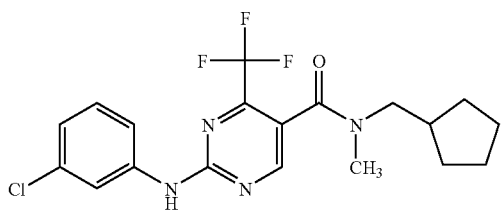

In a manner similar to Example 188c) 2-(3-chlorophenylamino)-4-trifluoromethyl-pyrimidine-5-carboxylic acid (35 mg) and N-(cyclopentylmethyl)-N-methylamine hydrochloride (21 mg) together with an additional equivalent of N,N-diisopropylethylamine gave the title compound (42 mg)

NMR (DMSO-d6) Rotamers in 65:35 ratio δ 1.0-1.8 (8H, m), 2.13 (0.35H, m), 2.27 (0.65H, m), 2.88 (1.95H, s), 2.99 (1.05H, s), 3.14 (0.7H, d), 3.41 (1.3H, br s), 7.09 (1H, d), 7.36 (1H, t), 7.66 (1H, d), 7.96 (1H, m), 8.77 (1H, s), 10.6 (1H, s).

LC/MS t=3.77 min, Molecular ion observed (MH$^+$)=413 consistent with the molecular formula C$_{19}$H$_{20}$$^{35}$ClF$_3$N$_4$O

EXAMPLE 191

2-(5-Chloro-2-fluorophenylamino)-4-trifluoromethyl-pyrimidine-5-carboxylic acid cyclobutylmethyl-amide a)
2-Chloro-4-trifluoromethyl-pyrimidine-5-carboxylic acid cyclobutylmethyl-amide

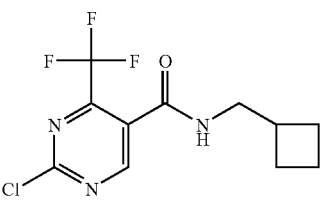

A mixture of 2-chloro-4-trifluoromethyl-pyrimidine-5-carbonyl chloride (613 mg) (Maybridge) and C-cyclobutyl-methylamine hydrochloride (304 mg) in dry dichloromethane (10 ml) was cooled to −30° C. and N,N-diisopropylethylamine (958 ul) was added dropwise. The mixture was stirred at room temp for 1 hour. Water (10 ml) was added, the layers separated and the organic layer was washed sequentially with 10 ml portions of water, dilute hydrochloric acid, water, dilute sodium bicarbonate solution and water, dried (MgSO$_4$) and evaporated. Purification by chromatography on silica gel (dichloromethane/ether 25:1) gave the title compound (449 mg).

NMR (CDCl$_3$) δ 1.75 (2H, m), 1.93 (2H, m), 2.10 (2H, m), 2.57 (1H, m), 3.50 (2H, t), 5.86 (1H, br s), 8.90 (1H, s).

b) 2-(5-Chloro-2-fluorophenylamino)-4-trifluoromethyl-pyrimidine-5-carboxylic acid cyclobutylmethyl-amide

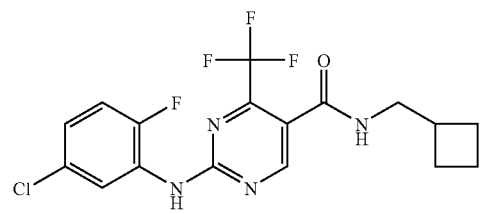

In a manner similar to Example 166, 5-chloro-2-fluoroaniline (109 mg) (Avacado) and 2-chloro-4-trifluoromethyl-pyrimidine-5-carboxylic acid cyclobutylmethyl-amide (44 mg) gave the title compound (45 mg).

NMR (DMSO-d6) δ 1.7 (2H, m), 1.8 (2H, m), 1.99 (2H, m), 2.47 (1H, m excess), 3.25 (2H, t), 7.3 (2H, m), 7.76 (1H, m), 8.56 (1H, t), 8.70 (1H, s), 10.2 (1H, s)

LC/MS t=3.52 min, Molecular ion observed (MH$^+$)=403 consistent with the molecular formula C$_{17}$H$_{15}$$^{35}$ClF$_4$N$_4$O

EXAMPLE 192

2-(3,5-Difluorophenylamino)-4-trifluoromethyl-pyrimidine-5-carboxylic acid cyclobutylmethyl-amide

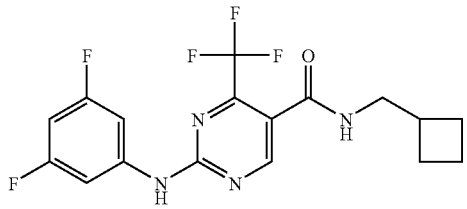

In a manner similar to Example 166, 3,5-difluoroaniline (97 mg) (Lancaster) and 2-chloro-4-trifluoromethyl-pyrimidine-5-carboxylic acid cyclobutylmethyl-amide (44 mg) gave the title compound (46 mg).

NMR (DMSO-d6) δ 1.7 (2H, m), 1.8 (2H, m), 2.0 (2H, m), 2.47 (1H, m excess), 3.27 (2H, t), 6.88 (1H, m), 7.55 (2H, m), 8.60 (1H, t), 8.83 (1H—, s), 10.8 (1H, s)

LC/MS t=3.54 min, Molecular ion observed (MH$^+$)=387 consistent with the molecular formula $C_{17}H_{15}F_5N_4O$

EXAMPLE 193

2-(3-Chloro-4-trifluoromethoxyphenylamino)-4-trifluoromethyl-pyrimidine-5-carboxylic acid cyclobutylmethyl-amide

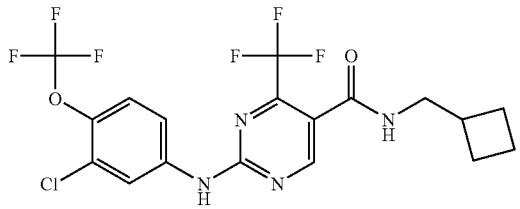

In a manner similar to Example 166, 3-chloro-4-trifluoromethoxy aniline (159 mg) (Lancaster) and 2-chloro-4-trifluoromethyl-pyrimidin-5-carboxylic acid cyclobutylmethyl-amide (44 mg) gave the title compound (59 mg).

NMR (DMSO-d6) δ 1.7 (2H, m), 1.8 (2H, m), 2.0 (2H, m), 2.47 (1H, m excess), 3.27 (2H, t), 7.56 (1H, d), 7.76 (1H, m), 8.16 (1H, d), 8.59 (1H, t), 8.81 (1H, s), 10.8 (1H, s)

LC/MS t=3.82 min, Molecular ion observed (MH$^+$)=469 consistent with the molecular formula $C_{18}H_{15}{}^{35}ClF_6N_4O_2$

EXAMPLE 194

2-(3-Chloro-4-fluorophenylamino)-4-trifluoromethyl-pyrimidine-5-carboxylic acid cyclobutylmethyl-amide

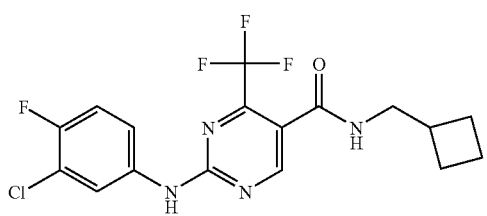

In a manner similar to Example 166, 3-chloro-4-fluoroaniline (109 mg) (Lancaster) and 2-chloro-4-trifluoromethyl-pyrimidine-5-carboxylic acid cyclobutylmethyl-amide (44 mg) gave the title compound (50 mg).

NMR (DMSO-d6) δ 1.7 (2H, m), 1.8 (2H, m), 2.0 (2H, m), 2.47 (1H, m excess), 3.27 (2H, t), 7.42 (1H, t), 7.67 (1H, m), 8.04 (1H, m), 8.57 (1H, t), 8.77 (1H, s), 10.6 (1H, s)

LC/MS t=3.60 min, Molecular ion observed (MH$^+$)=403 consistent with the molecular formula $C_{17}H_{15}{}^{35}ClF_4N_4O$

EXAMPLE 195

2-(3-Chloro-2-fluorophenylamino)-4-trifluoromethyl-pyrimidine-5-carboxylic acid cyclobutylmethyl-amide

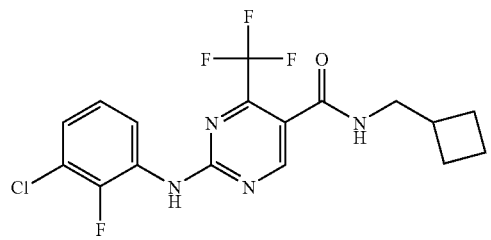

In a manner similar to Example 166, 3-chloro-2-fluoroaniline (109 mg) (Acros) and 2-chloro-4-trifluoromethyl-pyrimidine-5-carboxylic acid cyclobutylmethyl-amide (44 mg) gave the title compound (47 mg).

NMR (DMSO-d6) δ 1.7 (2H, m), 1.8 (2H, m), 2.0 (2H, m), 2.47 (1H, m excess), 3.23 (2H, t), 7.22 (1H, t), 7.42 (1H, t), 7.54 (1H, t), 8.55 (1H, t), 8.65 (1H, s), 10.2 (1H, s)

LC/MS t=3.49 min, Molecular ion observed (MH$^+$)=403 consistent with the molecular formula $C_{17}H_{15}{}^{35}ClF_4N_4O$

EXAMPLE 196

2-(3-Fluoro-4-trifluoromethylphenylamino)-4-trifluoromethyl-pyrimidine-5-carboxylic acid cyclobutylmethyl-amide

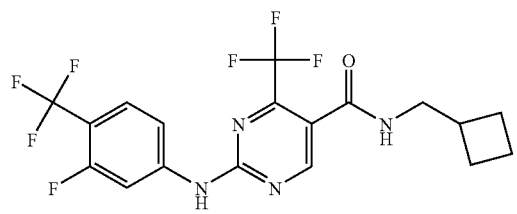

In a manner similar to Example 166, 3-fluoro-4-trifluoromethylaniline (134 mg) (ABCR) and 2-chloro-4-trifluoromethyl-pyrimidine-5-carboxylic acid C-cyclobutylmethyl-amide (44 mg) gave the title compound (41 mg).

NMR (DMSO-d6) δ 1.7 (2H, m), 1.8 (2H, m), 2.0 (2H, m), 2.47 (1H, m excess), 3.26 (2H, t), 7.67 (1H, d), 7.75 (1H, t), 8.02 (1H, d), 8.62 (1H, t), 8.87 (1H, s), 11.0 (1H, s)

LC/MS t=3.71 min, Molecular ion observed (MH$^+$)=437 consistent with the molecular formula $C_{18}H_{15}F_7N_4O$

EXAMPLE 197

2-(3-Chloro-4-cyanophenylamino)-4-trifluoromethyl-pyrimidine-5-carboxylic acid cyclobutylmethyl-amide

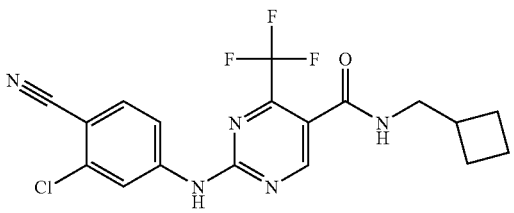

In a manner similar to Example 166, 3-chloro-4-cyanoaniline (114 mg) (Lancaster) and 2-chloro-4-trifluoromethyl-pyrimidine-5-carboxylic acid cyclobutylmethyl-amide (44 mg) gave the title compound (26 mg).

NMR (DMSO-d6) δ 1.7 (2H, m), 1.8 (2H, m), 2.0 (2H, m), 2.47 (1H, m excess), 3.27 (2H, t), 7.83 (1H, m), 7.93 (1H, d), 8.24 (1H, s), 8.62 (1H, t), 8.89 (1H, s), 11.1 (1H, s)

LC/MS t=3.50 min, Molecular ion observed (MH$^+$)=410 consistent with the molecular formula $C_{18}H_{15}{}^{35}ClF_3N_5O$

EXAMPLE 198

2-(3-Fluorophenylamino)-4-trifluoromethyl-pyrimidine-5-carboxylic acid cyclobutylmethyl-amide

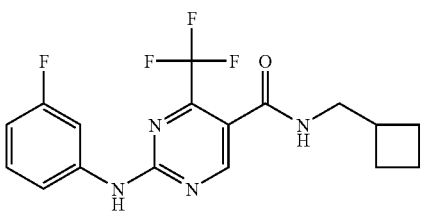

In a manner similar to Example 188, 2-(3-fluorophenylamino)-4-trifluoromethyl-pyrimidine-5-carboxylic acid (30 mg) and C-cyclobutylmethylamine hydrochloride (18 mg) gave the title compound (31 mg).

NMR (DMSO-d6) δ 1.7 (2H, m), 1.8 (2H, m), 2.0 (2H, m), 2.47 (1H, m excess), 3.26 (2H, t), 6.86 (1H, m), 7.37 (1H, m), 7.50 (1H, d), 7.76 (1H, m), 8.58 (1H, t), 8.78 (1H, s), 10.6 (1H, s)

LC/MS t=3.42 min, Molecular ion observed (MH$^+$)=369 consistent with the molecular formula $C_{17}H_{16}F_4N_4O$

EXAMPLE 199

2-(3-Bromophenylamino 4-trifluoromethyl-pyrimidine-5-carboxylic acid cyclobutylmethyl-amide

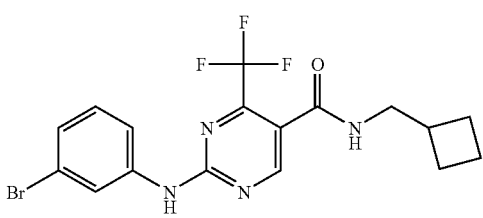

In a manner similar to Example 188, 2-(3-bromophenylamino)-4-trifluoromethyl-pyrimidine-5-carboxylic acid (36 mg) and C-cyclobutylmethylamine hydrochloride (18 mg) gave the title compound (33 mg).

NMR (DMSO-d6) δ 1.7 (2H, m), 1.8 (2H, m), 2.0 (2H, m), 2.47 (1H, m excess), 3.26 (2H, t), 7.22 (1H, d), 7.31 (1H, t), 7.70 (1H, d), 8.10 (1H, t), 8.57 (1H, t), 8.78 (1H, s), 10.6 (1H, s)

LC/MS t=3.60 min, Molecular ion-observed (MH$^+$)=431 consistent with the molecular formula $C_{17}H_{16}{}^{81}BrF_3N_4O$

EXAMPLE 200

2-(2,3-Dichlorophenylamino)-4-trifluoromethyl-pyrimidine-5-carboxylic acid cyclobutylmethyl-amide

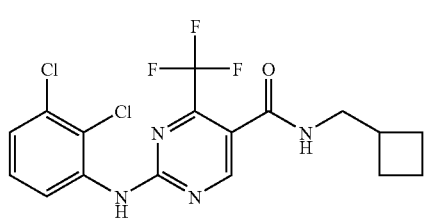

In a manner similar to Example 188, 2-(2,3-dichlorophenylamino)-4-trifluoromethyl-pyrimidine-5-carboxylic acid (36 mg) and C-cyclobutylmethylamine hydrochloride (18 mg) gave the title compound (36 mg).

NMR (DMSO-d6) δ 1.7 (2H, m), 1.8 (2H, m), 2.0 (2H, m), 2.47 (1H, m excess), 3.24 (2H, t), 7.40 (1H, t), 7.54 (2H, m), 8.54 (1H, t), 8.63 (1H, s), 10.1 (1H, s)

LC/MS t=3.61 min, Molecular ion observed (MH$^+$)=419 consistent with the molecular formula $C_{17}H_{15}{}^{35}Cl_2F_3N_4O$

EXAMPLE 201

2-(2,4-Dichlorophenylamino)-4-trifluoromethyl-pyrimidine-5-carboxylic acid cyclobutylmethyl-amide

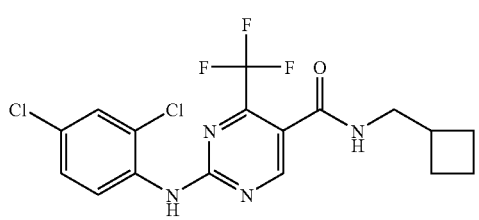

In a manner similar to Example 188, 2-(2,4-dichlorophenylamino)-4-trifluoromethyl-pyrimidine-5-carboxylic acid (36 mg) and C-cyclobutylmethylamine hydrochloride (18 mg) gave the title compound (37 mg).

NMR (DMSO-d6) δ 1.7 (2H, m), 1.8 (2H, m), 2.0 (2H, m), 2.47 (1H, m excess), 3.24 (2H, t), 7.47 (1H, m), 7.58 (11H, d), 7.72 (1H, d), 8.54 (1H, t), 8.65 (1H, s), 10.0 (1H, s)

LC/MS t=3.66 min, Molecular ion observed (MH$^+$)=419 consistent with the molecular formula $C_{17}H_{15}{}^{35}Cl_2F_3N_4O$

EXAMPLE 202

2-(2,5-Dichlorophenylamino)-4-trifluoromethyl-pyrimidine-5-carboxylic acid cyclobutylmethyl-amide

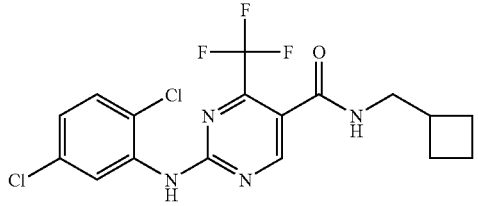

In a manner similar to Example 188, 2-(2,5-dichlorophenylamino)-4-trifluoromethyl-pyrimidine-5-carboxylic acid (36 mg) and C-cyclobutylmethylamine hydrochloride (18 mg) gave the title compound (33 mg).

NMR (DMSO-d6) δ 1.7 (2H, m), 1.8 (2H, m), 2.0 (2H, m), 2.47 (1H, m excess), 3.24 (2H, t), 7.34 (1H, m), 7.58 (1H, d), 7.72 (1H, d), 8.55 (1H, t), 8.66 (1H, s), 10.0 (1H, s)

LC/MS t=3.65 min, Molecular ion observed (MH$^+$)=419 consistent with the molecular formula $C_{17}H_{15}{}^{35}Cl_2F_3N_4O$

EXAMPLE 203

2-(2,6-Dichlorophenylamino)-4-trifluoromethyl-pyrimidine-5-carboxylic acid cyclobutylmethyl-amide

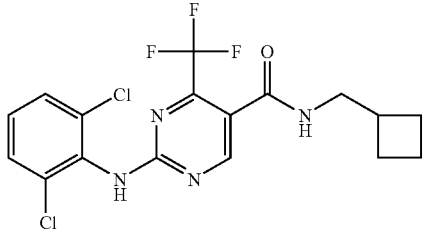

In a manner similar to Example 188, 2-(2,6-dichlorophenylamino)-4-trifluoromethyl-pyrimidine-5-carboxylic acid (36 mg) and C-cyclobutylmethylamine hydrochloride (18 mg) gave the title compound (35 mg).

NMR (DMSO-d6) δ 1.7 (2H, m), 1.8 (2H, m), 2.0 (2H, m), 2.47 (1H, m excess), 3.22 (2H, t), 7.39 (1H, t), 7.59 (2H, d), 8.56 (2H, m), 10.1 (1H, s).

LC/MS t=3.38 min, Molecular ion observed (MH$^+$)=419 consistent with the molecular formula $C_{17}H_{15}{}^{35}Cl_2F_3N_4O$

EXAMPLE 204

2-(3,4-Dichlorophenylamino)-4-trifluoromethyl-pyrimidine-5-carboxylic acid cyclobutylmethyl-amide

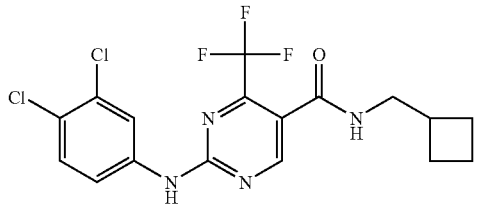

In a manner similar to Example 188, (3,4-dichlorophenylamino)-4-trifluoromethyl-pyrimidine-5-carboxylic acid (36 mg) and C-cyclobutylmethylamine hydrochloride (18 mg) gave the title compound (36 mg).

NMR (DMSO-d6) δ 1.7 (2H, m), 1.8 (2H, m), 2.0 (2H, m), 2.47 (1H, m excess), 3.26 (2H, t), 7.60 (1H, d), 7.69 (1H, m), 8.16 (1H, d), 8.58 (1H, t), 8.80 (1H, s), 10.7 (1H, s)

LC/MS t=3.77 min, Molecular ion observed (MH$^+$)=419 consistent with the molecular formula $C_{17}H_{15}{}^{35}Cl_2F_3N_4O$

EXAMPLE 205

2-(3-Methoxyphenylamino)-4-trifluoromethyl-pyrimidine-5-carboxylic acid cyclobutylmethyl-amide

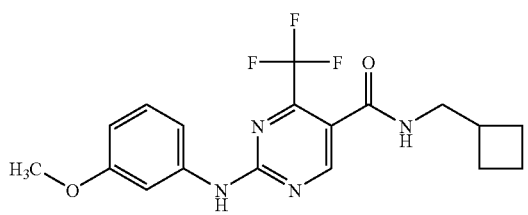

In a manner similar to Example 188, 2-(3-methoxyphenylamino)-4-trifluoromethyl-pyrimidine-5-carboxylic acid (31 mg) and C-cyclobutylmethylamine hydrochloride (18 mg) gave the title compound (38 mg).

NMR (DMSO-6) δ 1.7 (2H, m), 1.8 (2H, m), 2.0 (2H, m), 2.47 (1H, m excess), 3.26 (2H, t), 3.74 (3H, s), 6.63 (1H, d), 7.24 (2H, m), 7.52 (1H, s), 8.56 (1H, t), 8.72 (1H, s), 10.4 (1H, s)

LC/MS t=3.35 min, Molecular ion observed (MH$^+$)=381 consistent with the molecular formula $C_{18}H_{19}F_3N_4O_2$

EXAMPLE 206

2-(3,5-Dichlorophenylamino)-4-trifluoromethyl-pyrimidine-5-carboxylic acid cyclobutylmethyl-amide

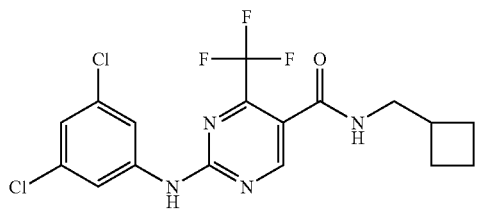

In a manner similar to Example 188, 2-(3,5-dichlorophenylamino)-4-trifluoromethyl-pyrimidine-5-carboxylic acid (36 mg) and C-cyclobutylmethylamine hydrochloride (18 mg) gave the title compound (36 mg).

NMR (DMSO-d6) δ 1.7 (2H, m), 1.8 (2H, m), 2.0 (2H, m), 2.47 (1H, m excess), 3.26 (2H, t), 7.60 (1H, d), 7.69 (1H, m), 8.16 (1H, d), 8.58 (1H, t), 8.80 (1H, s), 10.7 (1H, s)

LC/MS t=3.84 min, Molecular ion observed (MH$^+$)=419 consistent with the molecular formula $C_{17}H_{15}{}^{35}Cl_2F_3N_4O$

EXAMPLE 207

2-(3-Bromophenylamino)-4-trifluoromethyl-pyrimidine-5-carboxylic acid cyclopentylamide

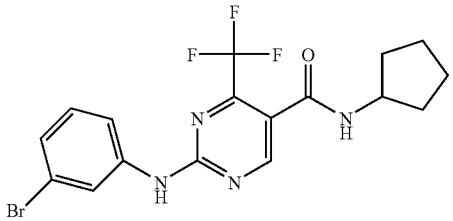

In a manner similar to Example 188, 2-(3-bromophenylamino)-4-trifluoromethyl-pyrimidine-5-carboxylic acid (36 mg) and cyclopentylamine (18 mg) gave the title compound (28 mg).

NMR (DMSO-d6) δ 1.5 (4H, m), 1.66 (2H, m), 1.86 (2H, m), 4.16 (1H, m), 7.22 (1H, d), 7.31 (1H, t), 7.70 (1H, d), 8.10 (1H, t), 8.53 (1H, d), 8.79 (1H, s), 10.6 (1H, s)

LC/MS t=3.39 min, Molecular ion observed (MH$^+$)=431 consistent with the molecular formula $C_{17}H_{16}{}^{81}BrF_3N_4O$

EXAMPLE 208

2-(2,4-Dichlorophenylamino)-4-trifluoromethyl-pyrimidine-5-carboxylic acid cyclopentylamide

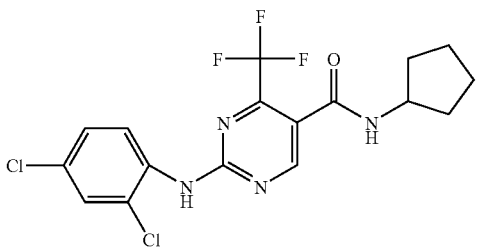

In a manner similar to Example 188, 2-(2,4-dichlorophenylamino)-4-trifluoromethyl-pyrimidine-5-carboxylic acid (26 mg) and cyclopentylamine (18 mg) gave the title compound (21 mg).

NMR (DMSO-d6) δ 1.5 (4H, m), 1.63 (2H, m), 1.84 (2H, m), 4.14 (1H, m), 7.47 (1H, m), 7.56 (1H, d), 7.71 (1H, d), 8.50 (1H, d), 8.62 (1H, s), 10.0 (1H, s)

LC/MS t=3.40 min, Molecular ion observed (MH$^+$)=419 consistent with the molecular formula $C_{17}H_{15}{}^{35}Cl_2F_3N_4O$

EXAMPLE 209

2-(3-Chlorophenylamino)-4-trifluoromethyl-pyrimidine-5-carboxylic acid cyclopropylamide

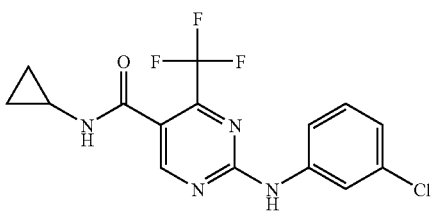

In a manner similar to Reference Example 1 (c) 2-(3-chlorophenylamino)-4-trifluoromethyl-pyrimidine-5-carboxylic acid (35 mg) and cyclopropylamine (9 mg, ex Lancaster) afforded the title compound (32 mg).

NMR (DMSO-d6) δ 0.49-0.52 (2H, m), 0.69-0.74 (2H, m), 2.78 (1H, m), 7.09 (1H, d), 7.36 (1H, t), 7.65 (1H, d), 7.95 (1H, s), 8.65 (1H, d), 8.80 (1H s), 10.60 (1H, s)

LC/MS, t=3.25 min, Molecular ion observed (MH$^+$)=357 consistent with the molecular formula $C_{15}H_{12}N_4OF_3{}^{35}Cl$

EXAMPLE 210

2-(3-Chlorophenylamino)-trifluoromethyl-pyrimidine-5-carboxylic acid (3,3-dimethylbutyl)-amide

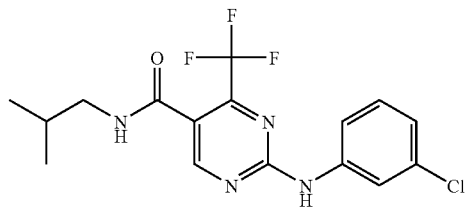

In a manner similar to Reference Example 1 (c) 2-(3-chlorophenylamino)-4-trifluoromethyl-pyrimidine-5-carboxylic acid (50 mg) and 3,3-dimethylbutylamine (17 mg, ex Aldrich) afforded the title compound (32 mg).

NMR (DMSO-d6) δ 0.96 (6H, d), 1.85 (1H, m), 3.12 (2H, t), 7.16 (1H, d), 7.42 (1H, t), 7.71 (1H, d), 8.02 (1H, s), 8.65 (1H, t), 8.86 (1H s), 10.70 (1H, s)

LC/MS, t=3.49 min, Molecular ion observed (MH$^+$)=373 consistent with the molecular formula $C_{16}H_{16}N_4OF_3{}^{35}Cl$

EXAMPLE 211

2-(3-Chlorophenylamino)-4-trifluoromethyl-pyrimidine-5-carboxylic acid methyl-(tetrahydro-pyran-4-ylmethyl)-amide (a). To a solution of 4-aminomethyltetrahydropyran (500 mg, ex Combi-Blocks, Inc.) in dichloromethane (10 ml) at 0° C. was added triethylamine (1.2 ml) followed by a solution of di-tert-butyl dicarbonate (1.14 g) in dichloromethane (4 ml). The reaction was stirred at 0° C. for 1 h. Dichloromethane was removed under reduced pressure and ethyl acetate added (10 ml). The solution was washed sequentially with 2N hydrochloric acid (10 ml), water (10 ml), 5% sodium bicarbonate solution (10 ml), and water (10 ml), dried (MgSO$_4$) and evaporated. The residue was purified by chromatography eluting with 2% MeOH/CH$_2$Cl$_2$, to afford N-tetrahydro-pyran-4-ylmethyl)carbamic acid tert-butyl ester (809 mg).

NMR (DMSO-d6) δ 1.15 (2H, m), 1.45 (9H, s), 1.80-1.95 (3H, d,m), 2.87 (2H, t), 3.30 (2H, t), 3.90 (2H, d,d), 6.95 (1H, t).

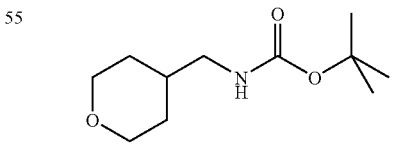

(b). To a solution of N-(tetrahydro-pyran-4-ylmethyl)-carbamic acid tert-butyl ester (800 mg) in THF (10 ml) at room temperature under nitrogen was added 60% sodium hydride (164 mg, ex Aldrich) portionwise. The reaction was stirred until effervescence had ceased and then methyl iodide (280 µl, ex Lancaster) was added. Stirring was continued at room temperature overnight. THF was removed under reduced pressure and ethyl acetate was added (10 nm). This was washed three times with water (10 ml), dried (MgSO₄) and evaporated. The residue was purified by chromatography eluting with 3% MeOH/CH₂Cl₂, to afford N-methyl-N-tetrahydro-pyran-4-ylmethyl)-carbamic acid tert-butyl ester (745 mg).

NMR (DMSO-d6) δ 1.15 (2H, m), 1.45 (9H, s), 1.50 (2H, m), 1.80 (1H, m) 2.80 (3H, d), 3.08 (2H, d), 3.28 (2H, t), 3.85 (2H, d).

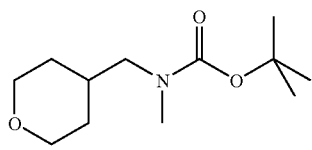

(c). A solution of N-methyl-N-(tetrahydro-pyran-4-ylmethyl)-carbamic acid tert-butyl ester (740 mg) in 4N hydrochloric acid in 1,4-dioxan (10 ml, ex Aldrich) was stirred at room temperature for 1 h. The dioxan was removed under reduced pressure and the residue triturated with ether. The solid was filtered onto a sinter, washed with ether and dried, to afford N-methyl-N-(tetrahydro-pyran-4-ylmethyl)-amine hydrochloride (460 mg).

NMR (DMSO-d6) δ 1.15 (2H, m), 1.65 (2H, d), 1.95 (1H, m) 2.50 (3H, d), 2.80 (2H, d), 3.30 (2H, t), 3.85 (2H, d), 9.0 (2H, s).

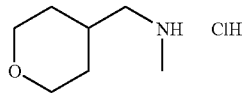

(d). In a manner similar to Reference Example 1 (c) 2-(3-chlorophenylamino)-4-trifluoromethyl-pyrimidine-5-carboxylic acid (50 mg) and N-methyl-N-(tetrahydro-pyran-4-yl methyl)amine hydrochloride (39 mg) afforded, after Biotage chromatography over silica gel, eluting with 1% MeOH/CH₂Cl₂, the title compound (33 mg).

NMR (DMSO-d6) Rotamers in 65:35 ratio δ 1.05 (0.7H, m), 1.23 (1.3H, m), 1.45 (0.7H, d), 1.58 (1.3H, d), 1.85 (0.35H, m), 2.0 (0.65H, m), 2.89 (1.95H, s), 2.98 (1.05H, s), 3.10-3.40 (4H, m), 3.80 (0.7H, d), 3.88 (1.3H, d), 7.10 (1H, d), 7.36 (1H, t), 7.65 (1H, t), 7.97 (1H, s), 8.75 (0.35H, s), 8.80 (0.65H, s), 10.6 (1H, s)

LC/MS, t=3.29 min, Molecular ion observed (MH⁺)=429 consistent with the molecular formula $C_{19}H_{20}N_4O_2F_3{}^{35}Cl$

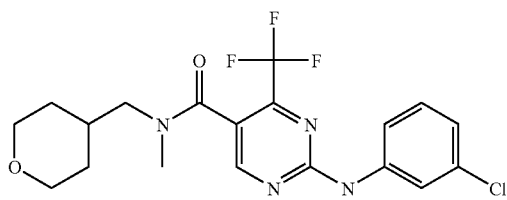

EXAMPLE 212

2-(2-Fluoro-3-chloro-phenylamino)-4-trifluoromethyl-pyrimidine-5-carboxylic acid (tetrahydro-pyran-4-ylmethyl)-amide

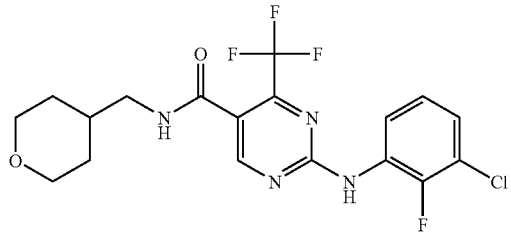

In a manner similar to Example 166, 2-chloro-4-trifluoromethyl-pyrimidine-5-carboxylic acid (tetrahydro-pyran-4-ylmethyl)-amide (100 mg) and 2-fluoro-3-chloroaniline (225 mg, ex Acros) afforded the title compound (85 mg) after purification by trituration with isohexane.

NMR (DMSO-d6) δ 1.14-1.23 (2H, m), 1.6 (2H, d), 1.72 (1H, m), 3.1 (2H, t), 3.25 (2H, m), 3.85 (2H, d), 7.24 (1H, t), 7.42 (1H, t), 7.55 (1H, t), 8.61 (1H, t), 8.70 (1H, s), 10.20 (1H, s)

LC/MS, t=3.14 min, Molecular ion observed (MH⁺)=433 consistent with the molecular formula $C_{18}H_{17}N_4O_2F_4{}^{35}Cl$

EXAMPLE 213

2-(2-Fluoro-5-chloro-phenylamino)-4-trifluoromethyl-pyrimidine-5-carboxylic acid (tetrahydro-pyran-4-ylmethyl-amide

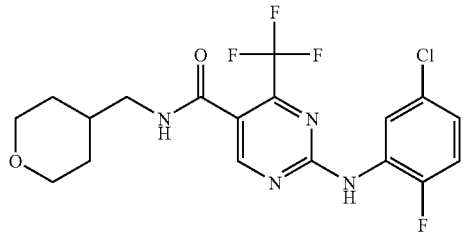

In a manner similar to Example 166, 2-chloro-4-trifluoromethyl-pyrimidine-5-carboxylic acid (tetrahydro-pyran-4-ylmethyl)-amide (100 mg) and 2-fluoro-5-chloroaniline (225 mg, ex Avocado) afforded the title compound (96 mg) after purification by trituration with isohexane.

NMR (DMSO-d6) δ 1.17-1.23 (2H, m), 1.6 (2H, d), 1.71 (1H, m), 3.1 (2H, t), 3.25 (2H, m), 3.85 (2H, d), 7.27-7.37 (2H, t,m), 7.76 (1H, dd), 8.62 (H, t), 8.73 (1H, s), 10.15 (1H, s)

LC/MS, t=3.15 min, Molecular ion observed (MH⁺)=433 consistent with the molecular formula $C_{18}H_{17}N_4O_2F_4{}^{35}Cl$

EXAMPLE 214

2-(3,5-Difluorophenylamino)-4-trifluoromethyl-pyrimidine-5-carboxylic acid (tetrahydro-pyran-4-ylmethyl)-amide

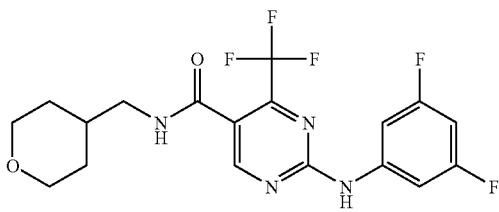

In a manner similar to Example 167, 2-chloro-4-trifluoromethyl-pyrimidine-5-carboxylic acid (tetrahydro-pyran-4-ylmethyl)-amide (100 mg) and 3,5-difluoroaniline (199 mg, ex Lancaster) afforded the title compound (98 mg) after purification by trituration with isohexane.

NMR (DMSO-d6) δ 1.18-1.25 (2H, m), 1.61(2H, d), 1.74 (1H, m), 3.13 (2H, t), 3.27 (2H, m), 3.85 (2H, d), 6.88 (1H, t,), 7.52 7.55 (2H, m), 8.66 (1H, t), 8.86 (1H, s), 10.80 (1H, s)

LC/MS, t=3.18 min, Molecular ion observed (MH$^+$) 417 consistent with the molecular formula $C_{18}H_{17}N_4O_2F_5$

EXAMPLE 215

2-(4-Fluoro-3-chloro-phenylamino)-4-trifluoromethyl-pyrimidine-5-carboxylic acid (tetrahydro-pyran-4-ylmethyl)-amide

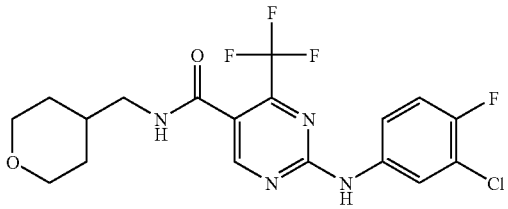

In a manner similar to Example 166, 2-chloro-4-trifluoromethyl-pyrimidine-5-carboxylic acid (tetrahydro-pyran-4-ylmethyl)-amide (100 mg) and 4-fluoro-3-chloroaniline (225 mg, ex Lancaster) afforded the title compound (134 mg) after purification by trituration with isohexane.

NMR (DMSO-d6) δ 1.18-1.23 (2H, m), 1.61 (2H, d), 1.75 (1H, m), 3.1 (2H, t), 3.25 (2H, m), 3.85 (2H, d), 7.42 (1H, t), 7.65 (1H, m), 8.05 (1H, dd), 8.63 (1H, t), 8.80 (1H, s), 10.65 (1H, s)

LC/MS, t=3.25 min, Molecular ion observed (MH$^+$)=433 consistent with the molecular formula $C_{18}H_{17}N_4O_2F_4{}^{35}Cl$

EXAMPLE 216

2-(4-Trifluoromethoxy-3-chloro-phenylamino)-4-trifluoromethyl-pyrimidine-5-carboxylic acid (tetrahydro-pyran-4-ylmethyl)-amide

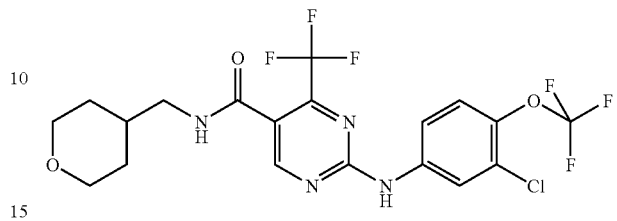

In a manner similar to Example 166, 2-chloro-4-trifluoromethyl-pyrimidine-5-carboxylic acid (tetrahydro-pyran-4-ylmethyl)-amide (100 mg) and 4-trifluoromethoxy-3-chloroaniline (327 mg, ex Lancaster) afforded the title compound (135 mg) after purification by trituration with isohexane.

NMR (DMSO-d6) δ 1.18-1.23 (2H, m), 1.61 (2H, d), 1.74 (1H, m), 3.13 (2H, t), 3.25 (2H, m), 3.85 (2H, d), 7.57 (1H, d), 7.75 (1H, dd), 8.14 (1H, d), 8.63 (1H, t), 8.84 (1H, s), 10.74 (1H, s)

LC/MS, t=3.51 min, Molecular ion observed (MH$^+$)=499 consistent with the molecular formula $C_{19}H_{17}N_4O_3F_6{}^{35}Cl$

EXAMPLE 217

2-(4-Cyano-3-chloro-phenylamino)-4-trifluoromethyl-pyrimidine-5-carboxylic acid (tetrahydro-pyran-4-ylmethyl)-amide

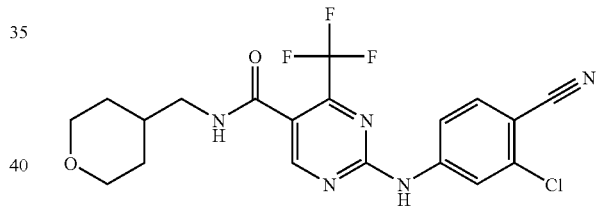

In a manner similar to Example 166, 2-chloro-4-trifluoromethyl-pyrimidine-5-carboxylic acid (tetrahydro-pyran-4-ylmethyl)-amide (100 mg) and 4-cyano-3-chloroaniline (236 mg, ex Lancaster) afforded the title compound (8 mg). Sample purified by mass directed auto-prep.

LC/MS, t=3.51 min, Molecular ion observed (MH$^+$)=440 consistent with the molecular formula $C_{19}H_{17}N_5O_2F_3{}^{35}Cl$

EXAMPLE 218

2-(4-Trifluoromethyl-3-fluoro-phenylamino)-4-trifluoromethyl-pyrimidine-5-carboxylic acid (tetrahydro-pyran-4-ylmethyl)-amide

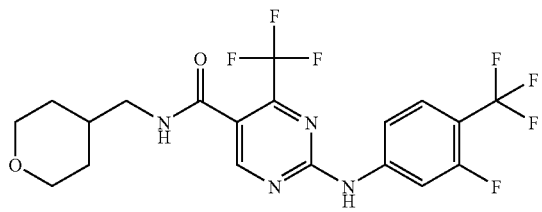

In a manner similar to Example 166, 2-chloro-4-trifluoromethyl-pyrimidine-5-carboxylic acid (tetrahydro-pyran-4-ylmethyl)-amide (100 mg) and 4-trifluoromethyl-3-fluoroaniline (277 mg, ex ABCR) afforded the title compound (125 mg) after purification by trituration with isohexane.

NMR (DMSO-d6) δ 1.16-1.25 (2H, m), 1.61 (2H, d), 1.73 (1H, m), 3.14 (2H, t), 3.25 (2H, m), 3.85 (2H, d), 7.67 (1H, d), 7.75 (1H, t), 8.02 (1H, d), 8.68 (1H, t), 8.90 (1H, s), 11.00 (1H, s)

LC/MS, t=3.38 min, Molecular ion observed (MH$^+$)=467 consistent with the molecular formula $C_{19}H_{17}N_4O_2F_7$

EXAMPLE 219

2-(4-Cyano-3-chloro-phenylamino)-4-trifluoromethyl-pyrimidine-5-carboxylic acid cyclopentylmethyl-amide

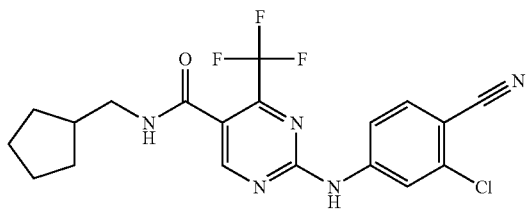

In a manner similar to Example 166, 2-chloro-4-trifluoromethyl-pyrimidine-5-carboxylic acid cyclopentylmethylamide (70 mg) and 4-cyano-3-chloroaniline (173 mg, ex Lancaster) afforded the title compound (125 mg). Purified by chromatography eluting with 1:1 ethyl acetate:hexane.

NMR (DMSO-d6) δ 1.20-1.25 (2H, m), 1.48-1.73 (6H, m), 2.08 (1H, m), 3.18 (2H, t), 7.83 (1H, dd), 7.84 (1H, d), 8.24 (1H, d), 8.66 (1H, t), 8.90 (1H s), 11.10 (1H, s)

LC/MS, t=3.68 min, Molecular ion observed (MH$^+$)=424 consistent with the molecular formula $C_{19}H_{17}N_5OF_3{}^{35}Cl$

EXAMPLE 220

2-(2,4-Dichloro-phenylamino)-4-trifluoromethyl-pyrimidine-5-carboxylic acid (1,1-dioxo-hexahydro-1l$^6$-thiopyran-4-yl)-amide

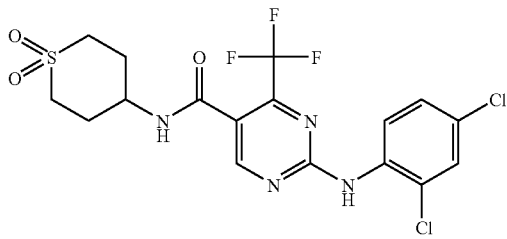

In a manner similar to Reference Example 1 (c) 2-(2,4-Dichlorophenylamino)+trifluoromethyl-pyrimidine-5-carboxylic acid (50 mg) and (1,1-dioxo-tetrahydro-2H-thiopyran-4-yl)amine hydrochloride (40 mg) (Ref. WO 02/18380) afforded the title compound (64 mg). Purified by chromatography eluting with 2% MeOH/CH$_2$Cl$_2$.

NMR (DMSO-d6) δ 1.97 (2H, m), 2.13 (2H, m), 3.13 (2H, m), 3.27 (2H, m), 4.10 (1H,m), 7.47 (1H, dd), 7.56 (1H, d), 7.72 (1H, d), 8.67 (1H t), 8.7 (1H, s), 10.05 (1H, s)

LC/MS, t=3.22 min, Molecular ion observed (MH$^+$)=483 consistent with the molecular formula $C_{17}H_{15}N_4O_3F_3{}^{35}Cl_2S$

EXAMPLE 221

2-(2,4-Difluoro-phenylamino)-4-trifluoromethyl-pyrimidine-5-carboxylic acid cyclohexylmethyl-amide

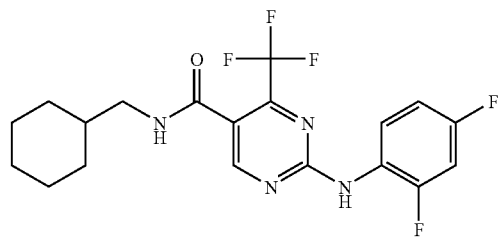

In a manner similar to Example 166, 2-chloro-4-trifluoromethyl-pyrimidine-5-carboxylic acid cyclohexylmethyl-amide (80 mg) and 2,4-difluoroaniline (160 mg, ex Lancaster) afforded the title compound (77 mg) after purification by trituration with isohexane/diethylether.

NMR (DMSO-d6) δ 0.89-0.95 (2H, m), 1.15-1.20 (3H, m), 1.46-1.47 (1H, m), 1.60-1.72 (5H, m), 3.05 (2H, t), 7.10 (1H, t), 7.35 (1H, m), 7.52 (1H, m), 8.53 (1H t), 8.62 (1H, s), 10.00 (1H, s)

LC/MS, t=3.63 min, Molecular ion observed (MH$^+$)=433 consistent with the molecular formula $C_{19}H_{19}N_4OF_5$

EXAMPLE 222

2-(2-Chloro-4-fluoro-phenylamino)-trifluoromethyl-pyrimidine-5-carboxylic acid cyclohexylmethyl-amide

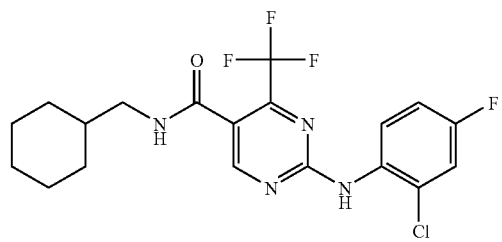

In a manner similar to Example 166, 2-chloro-4-trifluoromethyl-pyrimidine-5-carboxylic acid cyclohexylmethyl-amide (80 mg) and 2-chloro-4-fluoroaniline (181 mg, ex Lancaster) afforded the title compound (91 mg).

NMR (DMSO-d6) δ 0.89-0.95 (2H, m), 1.15-1.20 (3H, m), 1.44-1.46 (1H, m), 1.62-1.72 (5H, m), 3.05 (2H, t), 7.27 (1H, m), 7.55 (2H, m), 8.52 (1H t), 8.60 (1H, s), 10.00 (1H, s)

LC/MS, t=3.73 min, Molecular ion observed (MH$^+$)=431 consistent with the molecular formula $C_{19}H_{19}N_4OF_4{}^{35}Cl$

EXAMPLE 223

2-(2,4-Difluoro-phenylamino)-4-trifluoromethyl-pyrimidine-5-carboxylic acid cyclobutylmethyl-amide

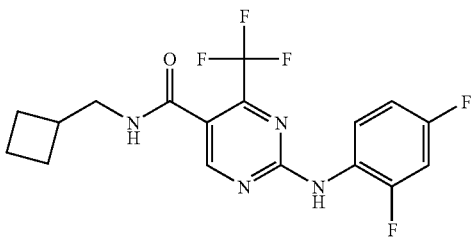

In a manner similar to Example 166, 2-chloro-4-trifluoromethyl-pyrimidine-5-carboxylic acid cyclobutylmethyl-amide (80 mg) and 2,4-difluoroaniline (198 mg, ex Lancaster) afforded the title compound (82 mg) after purification by trituration with isohexane/diethylether.

NMR (DMSO-d6) δ 1.67-2.01 (6H, m), 2.47 (1H, m), 3.23 (2H, t), 7.10 (1H, t), 7.35 (1H, m), 7.52 (1H, m), 8.53 (1H t), 8.62 (1H, s), 10.00 (1H, s)

LC/MS, t=3.40 min Molecular ion observed (MH$^+$)=386 consistent with the molecular formula $C_{17}H_{15}N_4OF_5$

EXAMPLE 224

2-(2-Chloro-4-fluoro-phenylamino)-4-trifluoromethyl-pyrimidine-5-carboxylic acid cyclobutylmethyl-amide

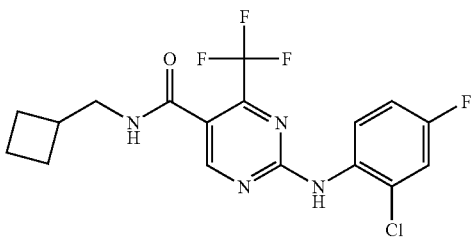

In a manner similar to Example 166, 2-chloro-4-trifluoromethyl-pyrimidine-5-carboxylic acid cyclobutylmethyl-amide (80 mg) and 2-chloro-4-fluoroaniline (198 mg, ex Lancaster) afforded the title compound (80 mg) after purification by trituration with 2N hydrochloric acid.

NMR (DMSO-d6) δ 1.67-2.00 (6H, m), 2.46 (1H, m), 3.23 (2H, t), 7.27 (1H, m), 7.55 (2H, m), 8.52 (1H t), 8.58 (1H, s), 9.90 (1H, s)

LC/MS, t=3.51 min, Molecular ion observed (MH$^+$)=403 consistent with the molecular formula $C_{17}H_{15}N_4OF_4{}^{35}Cl$

EXAMPLE 225

2-(2-Chloro-4-bromo-phenylamino)-4-trifluoromethyl-pyrimidine-5-carboxylic acid cyclohexylmethyl-amide

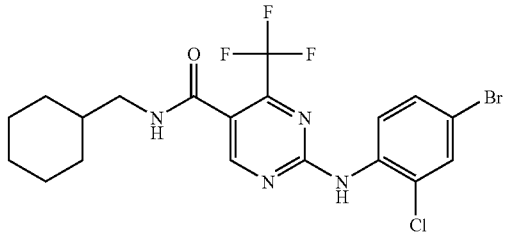

In a manner similar to Example 166, 2-chloro-4-trifluoromethyl-pyrimidine-5-carboxylic acid cyclohexylmethyl-amide (80 mg) and 2-chloro-4-bromoaniline (257 mg, ex Lancaster) afforded the title compound (96 mg) after purification by trituration with 2N hydrochloric acid.

NMR (DMSO-d6) δ 0.89-0.95 (2H, m), 1.15-1.20 (3H, m), 1.44-1.46 (1H, m), 1.62-1.72 (5H, m), 3.05 (2H, t), 7.52 (1H, d), 7.58 (1H, dd), 7.82 (1H, d), 8.55 (1H t), 8.63 (1H, s), 10.00 (1H, s)

LC/MS, t=3.97 min, Molecular ion observed (MH$^+$)=493 consistent with the molecular formula $C_{19}H_{19}N_4OF_3{}^{35}Cl^{81}Br$

EXAMPLE 226

2-(2-Fluoro-4-chloro-phenylamino)-4-trifluoromethyl-pyrimidine-5-carboxylic acid cyclohexylmethyl-amide

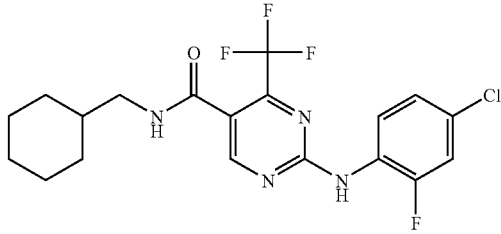

In a manner similar to Example 166, 2-chloro-4-trifluoromethyl-pyrimidine-5-carboxylic acid cyclohexylmethyl-amide (80 mg) and 2-fluoro-4-chloroaniline (180 mg, ex Lancaster) afforded the title compound (73 mg) after purification by trituration with 2N hydrochloric acid.

NMR (DMSO-d6) δ 0.95-0.98 (2H, m), 1.15-1.20 (3H, m), 1.44-1.46 (1H, m), 1.66-1.72 (5H, m), 3.05 (2H, t), 7.31 (1H, d), 7.53 (1H, dd), 7.60 (1H, t), 8.55 (1H t), 8.66 (1H, s), 10.00 (1H, s)

LC/MS, t=3.79 min, Molecular ion observed (MH$^+$)=431 consistent with the molecular formula $C_{19}H_{19}N_4OF_4{}^{35}Cl$

EXAMPLE 227

2-(2-Chloro-4-bromo-phenylamino)-4-trifluoromethyl-pyrimidine-5-carboxylic acid cyclobutylmethyl-amide

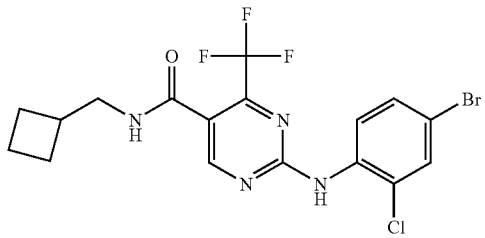

In a manner similar to Example 166, 2-chloro-4-trifluoromethyl-pyrimidine-5-carboxylic acid cyclobutylmethyl-amide (80 mg) and 2-chloro-4-bromoaniline (281 mg, ex Lancaster) afforded the title compound (103 mg) after purification by trituration with 2N hydrochloric acid.

NMR (DMSO-d6) δ 1.67-2.00 (6H, m), 2.45 (1H, m), 3.23 (2H, t), 7.50 (1H, d), 7.58 (1H, dd), 7.82 (1H, d), 8.53 (1H t), 8.61 (1H, s), 10.00 (1H, s)

LC/MS, t=3.77 min, Molecular ion observed (MH$^+$)=465 consistent with the molecular formula $C_{17}H_{15}N_4OF_3{}^{35}Cl{}^{81}Br$

EXAMPLE 228

2-(2-Fluoro-4-chloro-phenylamino)-4-trifluoromethyl-pyrimidine-5-carboxylic acid cyclobutylmethyl-amide

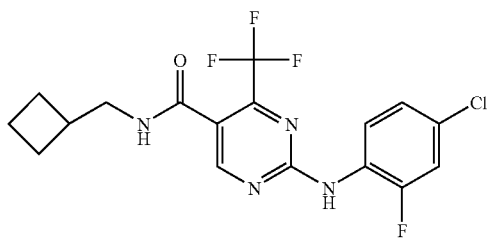

In a manner similar to Example 166, 2-chloro-4-trifluoromethyl-pyrimidine-5-carboxylic acid cyclobutylmethyl-amide (80 mg) and 2-fluoro-4-chloroaniline (198 mg, ex Lancaster) afforded the title compound (94 mg) after purification by trituration with 2N hydrochloric acid.

NMR (DMSO-d6) δ 1.67-2.08 (6H, m), 2.45 (1H, m), 3.23 (2H, t), 7.31 (1H, d), 7.53 (1H, dd), 7.60 (1H, t), 8.53 (1H t), 8.64 (1H, s), 10.00 (1H, s)

LC/MS, t=3.59 min, Molecular ion observed (MH$^+$)=403 consistent with the molecular formula $C_{17}H_{15}N_4OF_4{}^{35}Cl$

EXAMPLE 229

2-(2-Fluoro-4-bromo-phenylamino)-4-trifluoromethyl-pyrimidine-5-carboxylic acid cyclobutylmethyl-amide

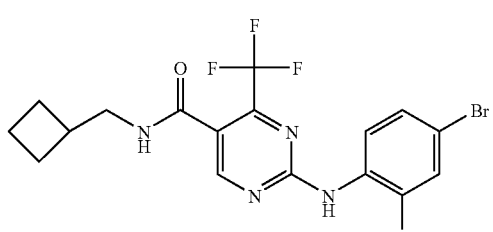

In a manner similar to Example 166, 2-chloro-4-trifluoromethyl-pyrimidine-5-carboxylic acid cyclobutylmethyl-amide (80 mg) and 2-fluoro-4-bromoaniline (259 mg, ex Lancaster) afforded the title compound (95 mg) after purification by trituration with 2N hydrochloric acid.

NMR (DMSO-d6) δ 1.67-2.00 (6H, m), 2.45 (1H, m), 3.23 (2H, t), 7.43 (1H, d), 7.54 (1H, t), 7.63 (1H, dd), 8.53 (1H t), 8.64 (1H, s), 10.00 (1H, s)

LC/MS, t=3.63 min, Molecular ion observed (MH$^+$)=449 consistent with the molecular formula $C_{17}H_{15}N_4OF_4{}^{81}Br$

EXAMPLE 230

2-(2-Bromo-4-chloro-phenylamino)-4-trifluoromethyl dine-5-carboxylic acid cyclobutylmethyl-amide

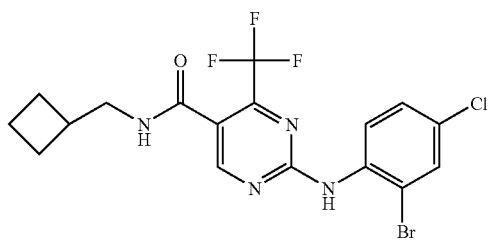

In a manner similar to Example 166, 2-chloro-4-trifluoromethyl-pyrimidine-5-carboxylic acid cyclobutylmethyl-amide (80 mg) and 2-bromo-4-chloroaniline (281 mg, ex Lancaster) afforded the title compound (105 mg) after purification by trituration with 2N hydrochloric acid.

NMR (DMSO-d6) δ 1.67-2.08 (6H, m), 2.45 (1H, m), 3.23 (2H, t), 7.52 (2H, m), 7.85 (1H, s), 8.53 (1H t), 8.60 (1H, s), 10.00 (1H, s)

LC/MS, t=3.75 min, Molecular ion observed (MH$^+$)=465 consistent with the molecular formula $C_{17}H_{15}N_4OF_3{}^{35}Cl{}^{81}Br$

EXAMPLE 231

2-(2-Fluoro-4-bromo-phenylamino)-4-trifluoromethyl-pyrimidine-5-carboxylic acid cyclohexylmethyl-amide

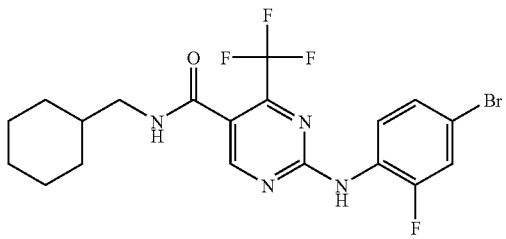

In a manner similar to Example 166, 2-chloro-4-trifluoromethyl-pyrimidine-5-carboxylic acid cyclohexylmethyl-amide (80 mg) and 2-fluoro-4-bromoaniline (236 mg, ex Lancaster) afforded the title compound (96 mg) after purification by trituration with 2N hydrochloric acid.

NMR (DMSO-d6) δ 0.90-0.92 (2H, m), 1.15-1.20 (3H, m), 1.44-1.46 (1H, m), 1.63-1.72 (5H, m), 3.05 (2H, t), 7.44 (1H, d), 7.55 (1H, t), 7.64 (1H, dd), 8.55 (1H t), 8.66 (1H, s), 10.00 (1H, s)

LC/MS, t 3.83 min, Molecular ion observed (MH$^+$) 477 consistent with the molecular formula $C_{19}H_{19}N_4OF_4{}^{81}Br$

EXAMPLE 232

2-(2-Fluoro-4-bromo-phenylamino)-4-trifluoromethyl-pyrimidine-5-carboxylic acid (tetrahydro-pyran-4-ylmethyl)-amide

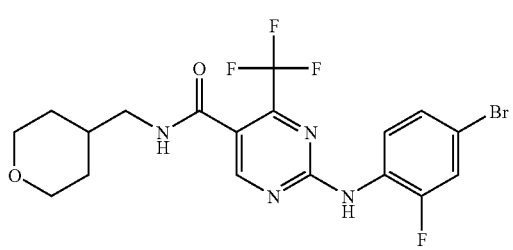

In a manner similar to Example 166, 2-chloro-4-trifluoromethyl-pyrimidine-5-carboxylic acid (tetrahydro-pyran-4-ylmethyl)-amide (80 mg) and 2-fluoro-4-bromoaniline (235 mg, ex Lancaster) afforded the title compound (100 mg) after purification by trituration with 2N hydrochloric acid.

NMR (DMSO-d6) δ 1.16-1.23 (2H, m), 1.60 (2H, d), 1.71 (1H, m), 3.1 (2H, t), 3.25 (2H, m), 3.85 (2H, d), 7.43 (1H, d), 7.55 (1H, t), 7.64 (1H, dd), 8.60 (1H, t), 8.65 (1H, s), 10.10 (1H, s)

LC/MS, t=3.28 min, Molecular ion observed (MH$^+$)=479 consistent with the molecular formula $C_{18}H_{17}N_4O_2F_4{}^{81}Br$

EXAMPLE 233

2-(2-Chloro-4-fluoro-phenylamino)-4-trifluoromethyl-pyrimidine-5 carboxylic acid (tetrahydro-pyran-4-ylmethyl)-amide

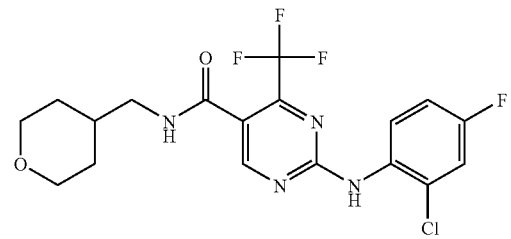

In a manner similar to Example 166, 2-chloro-4-trifluoromethyl-pyrimidine-5-carboxylic acid (tetrahydro-pyran-4-ylmethyl)-amide (80 mg) and 2-chloro-4-fluoroaniline (180 mg, ex Lancaster) afforded the title compound (95 mg) after purification by trituration with 2N hydrochloric acid.

NMR (DMSO-d6) δ 1.14-1.23 (2H, m), 1.59 (2H, d), 1.71 (1H, m), 3.1 (2H, t), 3.25 (2H, m), 3.85 (2H, d), 7.27 (1H, m), 7.55 (2H, m), 8.58 (1H, t), 8.61 (1H, s), 10.00 (1H, s)

LC/MS, t=3.14 min, Molecular ion observed (MH$^+$)=433 consistent with the molecular formula $C_{18}H_{17}N_4O_2F_4{}^{35}Cl$

EXAMPLE 234

242-Chloro-4-bromo-phenylamino)-trifluoromethyl-pyrimidine-5-carboxylic acid (tetrahydro-pyran-4-ylmethyl)-amide

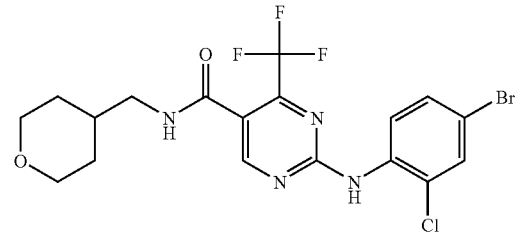

In a manner similar to Example 166, 2-chloro-4-trifluoromethyl-pyrimidine-5-carboxylic acid (tetrahydro-pyran-4-ylmethyl)-amide (80 mg) and 2-chloro-4-bromoaniline (255 mg, ex Lancaster) afforded the title compound (102 mg) after purification by trituration with 2N hydrochloric acid.

NMR (DMSO-d6) δ 1.14-1.23 (2H, m), 1.58 (2H, d), 1.72 (1H, m), 3.1 (2H, t), 3.28 (2H, m), 3.84 (2H, d), 7.51 (1H, d), 7.59 (1H, dd), 7.82 (1H, d), 8.58 (1H, t), 8.63 (1H, s), 10.00 (1H, s)

LC/MS, t=3.42 min, Molecular ion observed (MH$^+$)=495 consistent with the molecular formula $C_{18}H_{17}N_4O_2F_3{}^{35}Cl^{81}Br$

EXAMPLE 235

2-(2-Chloro-4-cyano-phenylamino)-4-trifluoromethyl-pyrimidine-5-carboxylic acid(tetrahydro-pyran-4-ylmethyl)-amide

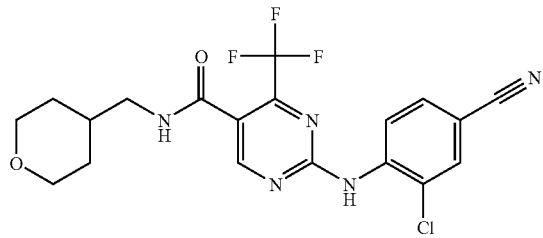

In a manner similar to Example 166, 2-chloro-4-trifluoromethyl-pyrimidine-5-carboxylic acid (tetrahydro-pyran-4-ylmethyl)-amide (80 mg) and 2-chloro-4-cyanoaniline (188 mg, ex Lancaster) afforded the title compound (22 mg). Sample purified by mass directed auto-prep.

NMR (DMSO-d6) δ 1.14-1.23 (2H, m), 1.59 (2H, d), 1.72 (1H, m), 3.12 (2H, t), 3.23 (2H, m), 3.85 (2H, d), 7.87 (1H, d), 7.92 (1H, d), 8.14 (1H, s), 8.65 (1H, t), 8.75 (1H, s), 10.20 (1H, s)

LC/MS, t=3.11 min, Molecular ion observed (MH$^+$)=440 consistent with the molecular formula $C_{19}H_{17}N_5O_2F_3{}^{35}Cl$

EXAMPLE 236

2-(2-Chloro-4-trifluoromethyl-phenylamino)-4-trifluoromethyl-pyrimidine-5-carboxylic acid (tetrahydro-pyran-4-ylmethyl)-amide

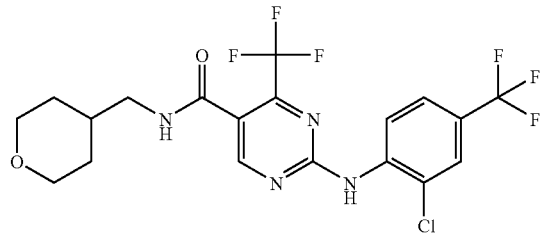

In a manner similar to Example 166, 2-chloro-4-trifluoromethyl-pyrimidine-5-carboxylic acid (tetrahydro-pyran-4-ylmethyl)-amide (80 mg) and 2-chloro-4-trifluoromethylaniline (241 mg, ex Lancaster) afforded the title compound (48 mg). Sample purified by mass directed auto-prep.

NMR (DMSO-d6) δ 1.17-1.23 (2H, m), 1.59 (2H, d), 1.72 (1H, m), 3.12 (2H, t), 3.23 (2H, m), 3.85 (2H, d), 7.77 (1H, d), 7.88 (1H, d), 7.96 (1H, s), 8.63 (1H, t), 8.72 (1H, s), 10.15 (1H, s)

LC/MS, t=3.47 min, Molecular ion observed (MH$^+$)=483 consistent with the molecular formula $C_{19}H_{17}N_4O_2F_6{}^{35}Cl$

EXAMPLE 237

2-(2 Chloro-4-cyano-phenylamino)-4-trifluoromethyl-pyrimidine-5-carboxylic acid cyclohexylmethyl-amide

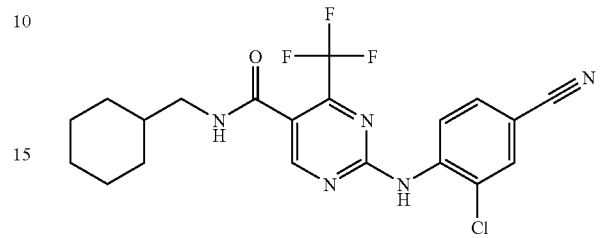

In a manner similar to Example 166, 2-chloro-4-trifluoromethyl-pyrimidine-5-carboxylic acid cyclohexylmethyl-amide (80 mg) and 2-chloro-4-cyanoaniline (189 mg, ex Lancaster) afforded the title compound (15 mg). Sample purified by mass directed auto-prep.

NMR (DMSO-d6) δ 0.90 (2H, m), 1.15-1.23 (3H, m), 1.44-1.46 (1H, m), 1.67-1.73 (5H, m), 3.06 (2H, t), 7.87 (1H, dd), 7.92 (1H, d), 8.14 (1H, d), 8.58 (1H t), 8.74 (1H, s), 10.10 (1H, s)

LC/MS, t=3.67 min, Molecular ion observed (MH$^+$)=438 consistent with the molecular formula $C_{20}H_{19}N_5OF_3{}^{35}Cl$

EXAMPLE 238

2-(2-Bromo-4-chloro-phenylamino)-4-trifluoromethyl-pyrimidine-5-carboxylic acid cyclohexylmethyl-amide

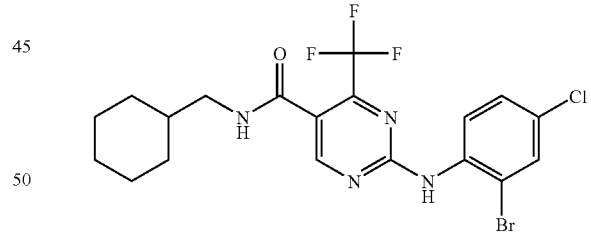

In a manner similar to Example 166, 2-chloro-4-trifluoromethyl-pyrimidine-5-carboxylic acid cyclohexylmethyl-amide (80 mg) and 2-bromo-4-chloroaniline (257 mg, ex Lancaster) afforded the title compound (23 mg). Sample purified by mass directed auto-prep.

NMR (DMSO-d6) δ 0.89-0.95 (2H, m), 1.15-1.20 (3H, m), 1.44-1.46 (1H, m), 1.62-1.72 (5H, m), δ 3.04 (2H, t), 7.52 (2H, m), 7.85 (1H, d), 8.53 (1H t), 8.61 (1H, s), 10.00 (1H, s)

LC/MS, t=3.94 min, Molecular ion observed (MH$^+$)=493 consistent with the molecular formula $C_{19}H_{19}N_4OF_3{}^{35}Cl^{81}Br$

EXAMPLE 239

2-(2-Bromo-4-chloro-phenylamino)-4-trifluoromethyl-pyrimidine-5-carboxylic acid (tetrahydro-pyran-4-ylmethyl)-amide

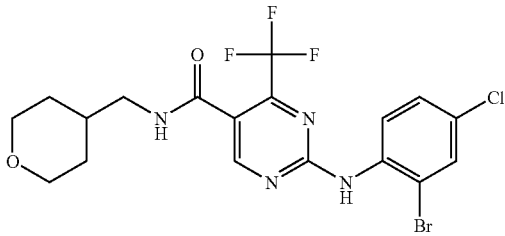

In a manner similar to Example 166, 2-chloro-4-trifluoromethyl-pyrimidine-5-carboxylic acid (tetrahydro-pyran-4-ylmethyl)-amide (80 mg) and 2-bromo-4-chloroaniline (255 mg, ex Lancaster) afforded the title compound (6 mg). Sample purified by mass directed auto-prep.

NMR (DMSO-d6) δ 1.14-1.23 (2H, m), 1.58 (2H, d), 1.72 (1H, m), 3.1 (2H, t), 3.28 (2H, m), 3.84 (2H, d), 7.50 (2H, m), 7.82 (1H, d), 8.58 (1H, t), 8.63 (1H, s), 10.00 (1H, s)

LC/MS, t=3.40 min, Molecular ion observed (MH$^+$)=495 consistent with the molecular formula $C_{18}H_{17}N_4O_2F_3{}^{35}Cl{}^{81}Br$

EXAMPLE 240

2-(3-Bromophenylamino)-4-trifluoromethyl-pyrimidine-5-carboxylic acid cyclopropylmethyl-amide

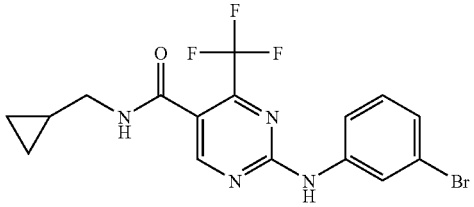

In a manner similar to Reference Example 1 (c) 2-(3-bromophenylamino)-4-trifluoromethyl-pyrimidine-5-carboxylic acid (80 mg) and cyclopropylmethylamine (19 mg, ex Lancaster) afforded the title compound (24 mg). Sample purified by mass directed auto-prep.

NMR (DMSO-d6) δ 0.22 (2H, m), 0.45 (2H, m), 1.67 (1H, m), 3.13 (2H, t), 7.23 (1H, d), 7.30 (1H, t), 7.72 (1H, d), 8.10 (1H, m), 8.68 (1H, t), 8.80 (1H s), 10.60 (1H, s)

LC/MS, t=3.49 min, Molecular ion observed (MH$^+$)=417 consistent with the molecular formula $C_{16}H_{14}N_4OF_3{}^{81}Br$

EXAMPLE 241

2-(2,4-Dichlorophenylamino)-4-trifluoromethyl-pyrimidine-5-carboxylic acid cyclopropylmethyl-amide

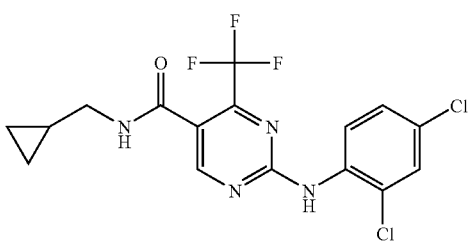

In a manner similar to Reference Example 1 (c) 2-(2,4-dichlorophenylamino)-4-trifluoromethyl-pyrimidine-5-carboxylic acid (80 mg) and cyclopropylmethylamine (19 mg, ex Lancaster) afforded the title compound (58 mg).

NMR (DMSO-d6) δ 0.22 (2H, m), 0.45 (2H, m), 1.67 (1H, m), 3.13 (2H, t), 7.23 (1H, d), 7.30 (1H, t), 7.72 (1H, d), 8.10 (1H, m), 8.68 (1H, t), 8.80 (1H s), 10.60 (1H, s)

LC/MS, t=3.56 min. Molecular ion observed (MH$^+$)=405 consistent with the molecular formula $C_{16}H_{13}N_4OF_3{}^{35}Cl$

EXAMPLE 242

2-(2,3-Difluorophenylamino)-4-trifluoromethyl-pyrimidine-5-carboxylic acid cyclohexylmethyl-amide

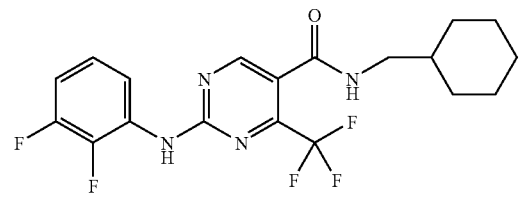

To a solution of 2-chloro-4-trifluoromethyl-pyrimidine-5-carboxylic acid cyclohexylmethyl-amide (Example 166a) (50 mg) in 1,4-dioxan (1 ml) was added 2,3-difluoroaniline (Aldrich) (113 mg) and the mixture was stirred at reflux for 47 hours using a Radleys Greenhouse Parallel Synthesiser. The dioxan was removed using a nitrogen blow down unit. The residue was taken up into methanol (0.5 ml) and dimethylsulfoxide (0.5 ml) and purified using a mass directed auto-preparative system to give the title compound (16 mg)

NMR (Chloroform-d6) δ0.94-1.08 (2H, m) 1.15-1.34 (3H, m), 1.5-1.6 (>1H,m & water) 1.65-1.73 (1H, m), 1.73-1.83 (4H, m), 3.30 (2H, t,), 5.91 (1H, bs) 6.88-6.98 (1H, m) 7.08-7.1 (1H, m), 7.66 (1H, bs), 8.16-825 (1H, m), 8.75 (1H, s).

LC/MS t=3.66 min, [MH$^+$] 415 consistent with the molecular formula $C_{19}H_{19}F_5N_4O$

EXAMPLE 243

2-(2-Fluoro-3-trifluoromethyl-phenylamino)-4-trifluoromethyl-pyrimidine-5-carboxylic acid cyclohexylmethyl-amide

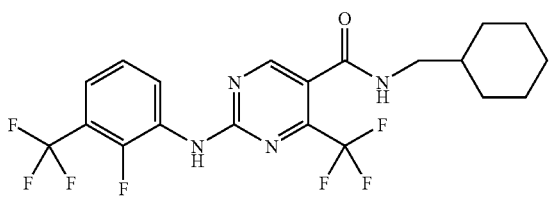

In a manner similar to Example 242, 2-chloro-4-trifluoromethyl-pyrimidine-5-carboxylic acid cyclohexylmethyl-amide (Example 166a) (50 mg) in 1,4-dioxan (1 ml) and 2-fluoro-3-trifluoromethylphenylamine (Aldrich) (156 mg) were reacted to give the title compound (11 mg)

NMR (Chloroform-d6) δ 0.94-1.08 (2H, m), 1.15-1.34 (3H, m), 1.55-1.59 (1H, m), 1.65-1.73 (1H, m), 1.73-1.83 (4H, m), 3.30 (2H, t,), 5.91 (1H, bs), 7.28-7.37 (2H, m), 7.74 (1H, bs), 8.65-8.73 (1H, m), 8.77-8.80 (1H, m)

LC/MS t=3.66 min [MH⁺]=465 consistent with the molecular formula $C_{20}H_{19}F_7N_4O$

EXAMPLE 244

2-(2-Chloro-4-methylphenylamino)-4-trifluoromethyl-pyrimidine-5-carboxylic acid cyclohexylmethyl-amide

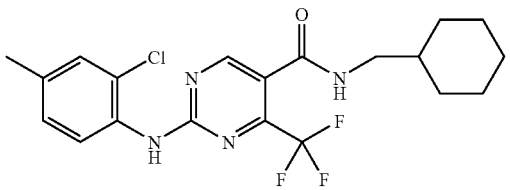

To a solution of 2-chloro-4-trifluoromethyl-pyrimidine-5-carboxylic acid cyclohexylmethyl-amide (Example 166a) (50 mg) in 1,4-dioxan (1 ml) was added 2-chloro-4-methylphenylamine (Aldrich) (109 mg) the mixture was stirred at reflux for 24 hours using a Radleys Greenhouse Parallel Synthesiser. The dioxan was removed using a nitrogen blow down unit The residue was taken up into methanol (0.5 ml) and dimethylsulfoxide (0.5 ml) and purified using mass directed auto-preparative system to give the title compound) (24 mg)

NMR (Methanol-d6) δ 1.50-1.60 (2H, m), 1.70-1.89 (3H, m), 2.06-215 (1H, m), 2.2-2.26 (1H, m), 2.27-2.38 (4H, m), 2.88 (3H, s), 3.71 (2H, d), 7.68 (1H, d), 7.85 (1H, s), 8.31 (1H, d), 9.10 (1H, s).

LC/MS t=3.81 min, [MH⁺]=427 consistent with the molecular formula $C_{20}H_{22}{}^{35}ClF_3N_4O$

EXAMPLE 245

2-(4-Chloro-3-methoxyphenylamino)-4-trifluoromethyl-pyrimidine-5-carboxylic acid cyclohexylmethyl-amide

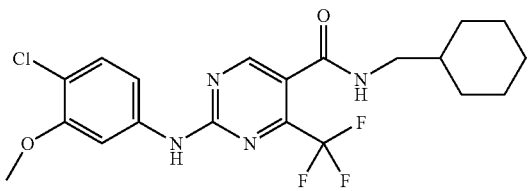

In a manner similar to Example 243, 2-chloro-4-trifluoromethyl-pyrimidine-5-carboxylic acid cyclohexylmethyl-amide (Example 166a) (50 mg) in 1,4-dioxan (1 ml) and 4-chloro-3-methoxy-phenylamine (Wychem) (122 mg) were reacted to give the title compound (33 mg)

NMR Methanol-d6) δ 0.95-1.06 (2H, m), 1.20-1.34 (3H, m), 1.55-1.64 (1H, m), 1.65-171 (1H, m), 1.72-1.85(4H, m), 3.19 (2H, d), 3.90 (3H, s), 7.18 (1H, dd), 7.27 (1H, d), 7.80 (1H, bs), 8.64 (1H,s).

LC/MS t=3.79 min, [MH⁺] 443 consistent with the molecular formula $C_{20}H_{22}{}^{35}ClF_3N_4O_2$

EXAMPLE 246

2-(5-Chloro-2-methylphenylamino)-4-trifluoromethyl-pyrimidine-5-carboxylic acid cyclohexylmethyl-amide

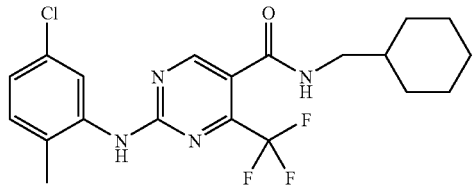

In a manner similar to Example 243, 2-chloro-4-trifluoromethyl-pyrimidine-5-carboxylic acid cyclohexylmethyl-amide (Example 166a) (50 mg) in 1,4-ioxan (1 ml) and 5-chloro-2-methyl aniline (Aldrich) (110 mg) were reacted to give the title compound (36 mg)

NMR (Methanol-d6) δ 1.47-1.59 (2H, m), 1.72-1.89 (3H, m), 2.05-2.18 (1H, m) 2.19-2.25 (1H, m), 2.31 (4H, t), 2.79 (3H, s), 3.71 (2H, d), 7.76 (1H, dd), 7.76 (1H, d), 8.17 (1H, d), 9.09 (1H, s)

LC/MS t=3.77 min [MH⁺]=427 consistent with the molecular formula $C_{20}H_{22}{}^{35}ClF_3N_4O$

EXAMPLE 247

2-(3-Chloro-4-fluoro-phenylamino)-4-trifluoromethyl-pyrimidine-5-carboxylic acid cyclopentylmethyl-amide

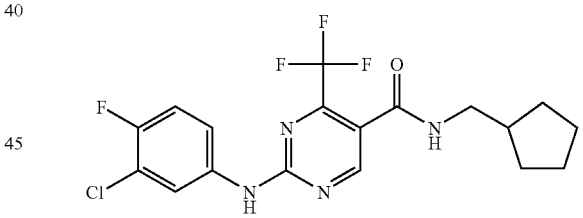

2-Chloro-4-trifluoromethyl-pyrimidine-5-carboxylic acid cyclopentylmethyl-amide (116 mg Example 183a), 3-chloro-4-fluoroaniline (ex-Aldrich, 275 mg), and 1,4-dioxan (1.2 ml) were stirred at 100° C. under nitrogen for 6 h. The cooled reaction mixture was evaporated in vacuo, treated with ethyl acetate (5 ml), washed with aqueous 2M hydrochloric acid (2×3 ml), followed by brine, and dried ($Na_2SO_4$). The solution was evaporated in vacuo to give the title compound (104 mg).

NMR δ (DMSO-d6)1.15-1.32 (2H,m), 1.46-1.66 (4H,m) 1.66-1.78 (2H, m), 2.1 (1H, q), 3.17 (2H,t), 7.4 (1H, t), 7.63-7.7 (1H, m), 8.05(1H, dd), 8.61 (1H, t), 8.79 (1H, s), 10.6 (1H,s).

LC/MS t=3.7 min. Molecular ion observed [MH+]=417 consistent with the molecular formula $C_{18}H_{11}F_4N_4O$.

EXAMPLE 248

2-(3-Chloro-2-fluoro-phenylamino)-4-trifluoromethyl-pyrimidine-5-carboxylic acid cyclopentylmethyl-amide

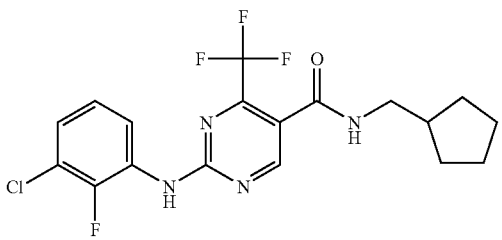

In a manner similar to Example 247, 3-chloro-2-fluoroaniline (ex-Acros, 275 mg) was reacted for 18 h, worked up analogously, then stirred in isohexane (6 ml), and filtered off to give the title compound (82 mg).

NMR δ (CDCl$_3$) 1.2-1.34 (2H, m), 1.55-1.76 (>4H, m+H$_2$O), 1.78-1.89 (2H, m), 2.16 (1H, q), 3.41 (1H, t), 5.83-5.95 (1H, brt), 7.1-7.18 (2H, m), 7.28 (1H, s), 7.66 (1H, brs), 8.3-8.4 (1H, m), 8.75 (1H, s).

LC/MS t=3.7 min, Molecular ion observed [MH$^+$] 417 consistent with the molecular formula C$_{18}$H$_{17}$ClF$_4$N$_4$O.

EXAMPLE 249

2-(2-Chloro-5-fluoro-phenylamino)-4-trifluoromethyl-pyrimidine-5-carboxylic acid cyclopentylmethyl-amide

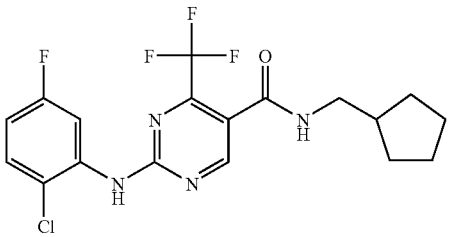

2-Chloro-4-trifluoromethyl-pyrimidine-5-carboxylic acid cyclopentylmethyl-amide (100 mg Example 183a), 2-chloro-5-fluoroaniline (ex-Fluorochem, 237 mg), and 1,4-dioxan (1 ml) were stirred at 100° C. under nitrogen for 18 h. The cooled reaction mixture was evaporated in vacuo, treated with ethyl acetate (5 ml), washed with aqueous 2M hydrochloric acid (2×3 ml), followed by water (2×3 ml), and dried (Na$_2$SO$_4$). The solution was evaporated in vacuo and the residue purified by mass directed auto-preparative purification to give the title compound (35 mg).

NMR δ (CDCl$_3$) 1.2-1.35 (2H, m), 1.53-1.76 (>4H, m+H$_2$O), 1.78-1.90 (2H, m), 2.17 (1H, q), 3.41 (2H, dd), 5.9 (1H, brt), 7.0-7.11 (2H, m), 7.65-7.7 (1H, m) 8.56 (1H, dd), 8.79 (1H, s).

LC/MS t=3.67 min, Molecular ion observed [MH$^+$] 417 consistent with the molecular formula C$_{18}$H$_{17}$Cl F$_4$N$_4$O.

EXAMPLE 250

2-(3,4-Dichlorophenylamino)-4-trifluoromethylpyrimidine-5-carboxylic acid (tetrahydro-pyran-4-ylmethyl)-amide

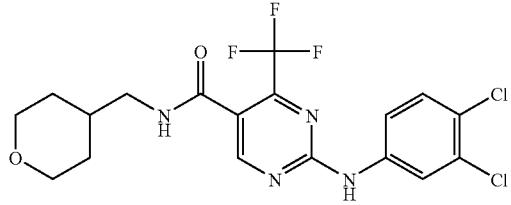

In a manner similar to Reference Example 1(c) 2-(3,4-dichlorophenylamino)-4-trifluoromethyl-pyrimidine-5-carboxylic acid (30 mg) and 4-aminomethyltetrahydropyran (20 mg, ex CombiBlocks) afforded the title compound (38 mg).

NMR (DMSO-d6) δ 1.18-1.25 (2H, m), 1.62 (2H, d), 1.74 (1H, m), 3.1 (2H, t), 3.25 (2H, m), 3.85 (2H, d), 7.60 (1H, t), 7.69 (1H, m), 8.16 (1H, dd), 8.64 (1H, t), 8.84 (1H, s), 10.70 (1H, s)

LC/MS, t=3.45 min, Molecular ion observed (MH$^+$)=449 consistent with the molecular formula C$_{18}$H$_{17}$N$_4$O$_2$$^{35}$Cl$_2$F$_3$

EXAMPLE 251

2-(Phenylamino)-4-trifluoromethyl-pyrimidine-5-carboxylic acid cyclopentylmethyl-amide

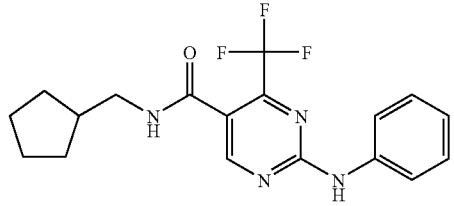

In a manner similar to Reference Example 1 (c), 2-(Phenylamino)-4-trifluoromethyl-pyrimidine-5-carboxylic acid (30 mg) and cyclopentylmethylamine hydrochloride (21 mg) afforded the title compound (32 mg) after purification by trituration with diethylether.

NMR (DMSO-d6) δ 1.20-1.25 (2H, m), 1.48-1.72 (6H, m), 2.07 (1H, m), 3.13 (2H, t), 7.04 (1H, t), 7.34 (2H, t), 7.74 (2H, d), 8.58 (1H, t), 8.70 (1H s), 10.35 (1H, s)

LC/MS, t=3.52 min, Molecular ion observed (MH$^+$)=365 consistent with the molecular formula C$_{18}$H$_{19}$N$_4$OF$_3$

EXAMPLE 252

2-(2-Fluoro-3-trifluoromethyl-phenylamino)-4-trifluoromethyl-pyrimidine-5-carboxylic acid cyclobutylmethyl-amide

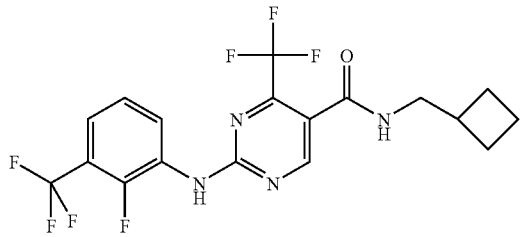

2-Chloro-4-trifluoromethyl-pyrimidin-5-carboxylic acid cyclobutylmethyl-amide (200 mg) in 2-fluoro-3-trifluoromethyl)aniline (0.5 ml) was heated at 180° C. under microwave irradiation for 30 minutes. The residue was dissolved in dichloromethane and purified over silica gel (Merck 9385) using the Biotage Horizon system eluting with 10% ethylacetate/isohexane to 100% ethyl acetate gradient to afford the title compound.

NMR (CDCl$_3$) δ1.70-1.81 (2H, m), 1.86-2.00 (2H, m), 2.07-2.17 (2H, m), 2.51-2.65 (1H, m), 3.48 (2H, dd), 5.78-5.86 (1H, m), 7.25-7.36 (2H, m), 7.70-7.76(1H, bs), 8.64-8.72 (1H, m), 8.75 8.79 (1H, s)

LC/MS, t=3.64 min, Molecular ion observed (MH$^+$)=437 consistent with the molecular formula $C_{18}H_{15}F_7N_4O$

EXAMPLE 253

2-(2-Methyl-4-chloro-phenylamino)-4-trifluoromethyl-pyrimidine-5-carboxylic acid cyclobutylmethyl-amide

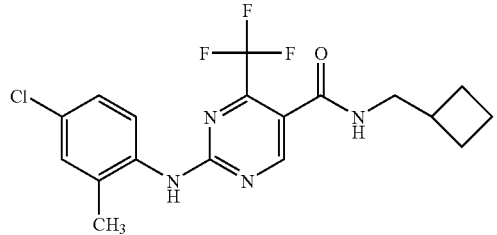

To a solution of 2-chloro-4-trifluoromethyl-pyrimidin-5-carboxylic acid cyclobutylmethyl-amide (50 mg) in 1,4-dioxan (1.0 ml) was added 2-methyl-4-chloroaniline (120 mg) and the solution heated at 180° C. under microwave irrdiation for 30×2 minutes. The residue was dissolved in 1:1 DMSO:methanol (11.0 ml) and purified by Mass Directed Auto-Purification to afford the title compound (36 mg).

NMR (CDCl$_3$) δ 1.79-1.80 (2H, m), 1.85-1.99 (2H, m), 2.05-2.16 (2H, m), 2.25-2.63 91H, m), 5.74-5.83 (1H, m), 7.15 (1H, bs), 7.2-7.78 (2H, m), 7.81 (1H, d), 8.66 (1H, s)

LC/MS, t=3.6 min, Molecular ion observed (MH$^+$)=398 consistent with the molecular formula $C_{18}H_{18}Cl\ F_3N_4O$

EXAMPLE 254

2-(2-Trifluoromethyl-4-bromo-phenylamino)-4-trifluoromethyl-pyrimidine-5-carboxylic acid (tetrahydro-pyran-4-ylmethyl)-amide

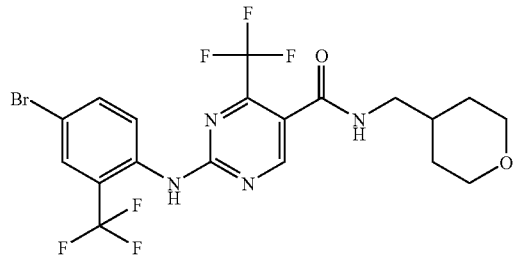

2-Chloro-4-trifluoromethyl-pyrimidin-5-carboxylic acid (tetrahydro-pyran-4-ylmethyl)-amide (80 mg) in 2-trifluoromethyl-4-bromoaniline (0.5 ml) was heated at 190° C. under microwave irradiation for 20 minutes. The sample was purified by mass directed auto-purification to afford the title compound (21 mg).

NMR (DMSO-d6) δ 1.15-1.23 (2H, m), 1.57 (2H, d), 1.60 (1H, m), 3.09 (2H, t), 3.26 (2H, t), 3.84 (2H, d), 7.51 (1H, d), 7.95 (2H, m), 8.58 (2H, s,t), 10.00 (1H, s)

LC/MS, t=3.41 min, Molecular ion observed (MH$^+$)=529 consistent with the molecular formula $C_{19}H_{17}N_4O_2F_6{}^{81}Br$

EXAMPLE 255

2-(3-Chlorophenylamino)-4-trifluoromethyl-pyrimidine-5-carboxylic acid (tetrahydrothiopyran-4-ylmethyl)amide a) 4-(Aminomethyl)tetrahydrothiopyran

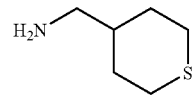

A solution of borane-tetrahydrofuran complex (1M in tetrahydrofuran, 11 ml) was added over 5 minutes to a solution of tetrahydro-2H-thiopyran-4-carbonitrile (1.27 g) [Heimgartner et al, Helv. Chim. Acta 80(5), 1528 (1997)] in dry tetrahydrofuran (5 ml) under nitrogen at room temperature. The solution was heated at reflux overnight, then cooled to 20° C. Methanol-(15 ml) was added dropwise keeping the temperature below 25° C., then the mixture was cooled to 0° C. and dry hydrogen chloride was bubbled through for 15 mins. The resulting mixture was heated at reflux for 1.5 hours, evaporated and the residue re-evaporated twice from methanol. Ether (30 ml) was added giving a white oily solid. The ether was decanted and the residue was dissolved in water (30 ml) and extracted with dichloromethane (2×30 ml). The remaining aqueous was made strongly basic with sodium hydroxide and extracted with dichloromethane (2×30 ml). The combined extracts were dried over potassium carbonate and evaporated to give the title compound (390 mg)

NMR (DMSO) δ 1.2 (5H, m), 2.0 (2H, m), 2.36 (2H, m), 2.55 (4H, m).

b) 2-(3 Chlorophenylamino)-4-trifluoromethyl-pyrimidine-5-carboxylic acid (tetrahydrothiopyran-4-ylmethyl)amide

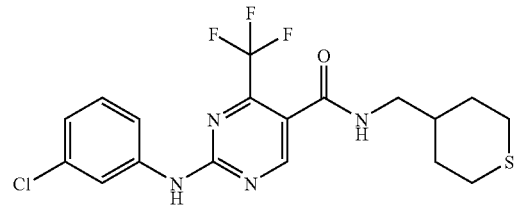

In a manner similar to Reference Example 1b) 2-(3-chlorophenylamino)-4-trifluoromethylpyrimidine-5-carboxylic acid (95 mg) and 4-aminomethyl)tetrahydrothiopyran (79 mg) (above) gave the title compound (92 mg).

NMR (DMSO-d6) δ 1.26 (2H, m), 1.55 (1H, m), 2.01 (2H, m), 2.60 (4H, m), 3.10 (2H, t), 7.09 (1H, m), 7.37 (1H, t), 7.65 (1H, m), 7.96 (1H, m), 8.63 (1H, t), 8.81 (1H, s), 10.6 (1H, s).

EXAMPLE 256

2-(2,4-Dichlorophenylamino)-4-trifluoromethyl-pyrimidine-5-carboxylic acid (tetrahydrothiopyran-4-ylmethyl)amide

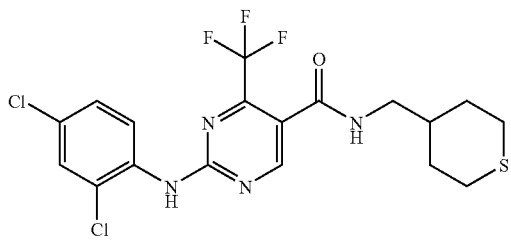

In a manner similar to Reference Example 1b) 2-(2,4-dichlorophenylamino)-4-trifluoromethyl-pyrimidine-5-carboxylic acid (106 mg) and 4-(aminomethyl)tetrahydrothiopyran (79 mg) (Example 255a) gave the title compound (82 mg).

NMR (DMSO-d6) δ 1.27 (2H, m), 1.55 (1H, m), 2.00 (2H, m), 2.59 (4H, m), 3.08 (2H, t), 7.47 (1H, m), 7.57 (1H, d), 7.72 (1H, m), 8.59 (1H, t), 8.64 (1H, s), 10.0 (1H, s).

LC/MS CF111493, t=3.70 min, Molecular ion observed (MH+)=465 consistent with the molecular formula $C_{18}H_{17}{}^{35}Cl_2F_3N_4OS$

EXAMPLE 263

2-(3-Chlorophenylamino)-4-trifluoromethyl-pyrimidine-5-carboxylic acid (2-oxo-propyl)-amide

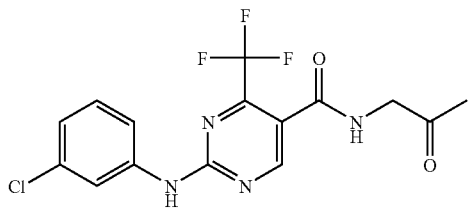

To a stirred solution of 2-(3-chloro-phenylamino)-trifluoromethyl-pyrimidine-5-carboxylic acid (2-hydroxy-propyl)-amide (200 mg) in dimethylsulfoxide (6.0 ml) and triethylamine (324 mg) at 0° C. was added a solution of sulphur trioxide-pyridine complex (250 mg) in dimethylsulfoxide (6.0 ml). This was allowed to warm to room temperature and after 2 hours the mixture was diluted with dichloromethane and washed twice with 0.1N hydrochloric acid. The organic layer was dried (Na₂SO₄) and evaporated. The sample was purified by mass directed auto-purification to afford the title compound (91 mg).

NMR (DMSO-d6) δ 2.15 (3H, s), 4.13 (2H, d), 7.10 (1H, d), 7.36 (1H, t), 7.67 (1H, d), 7.96 (1H, s), 8.84 (1H, s), 8.94 (1H, t), 10.55 (1H, s)

LC/MS, t=3.18 min, Molecular ion observed (MH+)=373 consistent with the molecular formula $C_{15}H_{12}N_4O_2F_3{}^{35}Cl$

EXAMPLE 264

2-(3-Chlorophenylamino)-4-trifluoromethylpyrimidine-5-carboxylic acid (dioxo-hexahydro-1l$^6$-thiopyran-4-ylmethyl)-amide

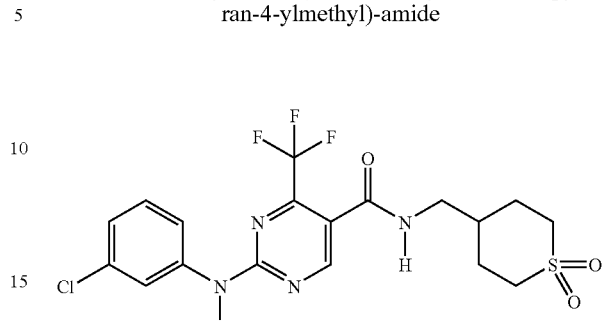

2-(3-Chlorophenylamino)-4-trifluoromethylpyrimidine-5-carboxylic acid (tetrahydro-thiopyran-4-ylmethyl)-amide (Example 255) (82 mg) was dissolved in dichloromethane (15 ml) and cooled in an ice bath. A solution of 3-chloroperbenzoic acid (95 mg; Lancaster 50-56%) in dichloromethane (5 ml) was added dropwise over 5 mins. The resulting solution was stirred at room temp for 2 hrs then a saturated solution of sodium sulphite (10 ml) was added and the mixture was stirred for 15 mins. Dichloromethane (20 ml), saturated sodium bicarbonate solution (20 ml) and water (30 ml) were added, separated and the organics were washed with water (2×30 ml), dried over magnesium sulphate and evaporated to an oil. Purification by chromatography on silica gel (dichloromethane/methanol 10:1) gave the title compound (17 mg).

LC/MS t=3.09 min, Molecular ion observed (MH+)=463 consistent with the molecular formula $C_{18}H_{18}{}^{35}Cl\,F_3N_4O_3S$

EXAMPLE 265

2-(2,4-Dichlorophenylamino)-4-trifluoromethylpyrimidine-5-carboxylic acid (dioxo-hexahydro-1l$^6$-thiopyran-4-ylmethyl)-amide

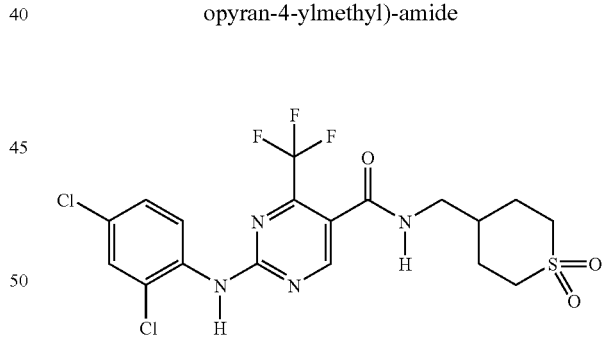

In a similar manner to Example 264, 2-(2,4-dichlorophenylamino)-4-trifluoromethylpyrimidine-5-carboxylic acid (tetrahydro-thiopyran-4-ylmethyl)-amide (Example 256) (72 mg) and 3-chloroperbenzoic acid (146 mg) gave the title compound (63 mg)

LC/MS t=3.21 min, Molecular ion observed (MH+)=497 consistent with the molecular formula $C_{18}H_{17}{}^{35}Cl_2F_3N_4O_3S$

EXAMPLE 266

Preparation of Nanomilled Compound 2.5 g of compound of example 176 was weighed into a 10 ml centrifuge tube. 25 ml of 0.3 mm yttrium zirconium (YTZ)

ceramic milling beads (Manufacturer: Tosoh, Japan; Supplier: Glen Creston Ltd., batch no. 5280130030)") was weighed into a 50 ml milling pot. 22.5 ml of aqueous 1.5% HPMC was measured with a measuring cylinder into a 100 ml beaker. This solution was homogenised for 3 seconds with an Ultra Turrax T25 homogeniser. Approximately 200 mg of the 2.5 g of the compound was added to the HPMC solution and homogenised at the lowest speed setting until the powder was wetted. This was repeated until all the compound had been added. The speed of the homogeniser was then increased to maximum and the suspension was homogenised for a further 3 minutes. This suspension was allowed to stand for 30 minutes in order to allow some of the foam to disperse. The suspension was then poured into the 50 ml pot containing the YTZ milling beads, stirring to release any trapped air. The lid to the pot was then fitted and the pot sealed with some Nesco film. This procedure was repeated for a second 50 ml nanomilling pot and both pots were placed on a Retsch mill and milled for a total of 8 hours.

The milling pots were removed from the Retsch mill and left to cool and for the foam to disperse overnight. In the morning the suspension and bead mixture was passed through a 200µ, 40 mm diameter screen. The contents from each 50 ml pot was washed with aqueous 1.5% HPMC: 10% of the original suspension volume (i.e. 2.5 ml). The suspension from the 2 pots was combined to make 1 batch. The suspension obtained from the method above was named the concentrate.

A sample of the concentrate was diluted 1 in 4 with aqueous 1.5% HPMC to give a nominal concentration of 25 mg/ml. This first dilution was assayed by HPLC. The concentration of the concentrate was calculated to be 91.21 mg/ml.

HPLC Conditions

Column: Symmetry $C_{18}$ 5µ3.9×150 mm column; flow rate 1.0 ml/min; column temp 40° C.; UV detection at 280 nm.

Mobile phase gradient: A: water+0.1% trifluoro acetic acid (TFA)

B: acetonitrile+0.1% TFA

TABLE A

| HPLC gradient | | |
|---|---|---|
| Time (min.) | A (%) | B (%) |
| 0 | 90 | 10 |
| 15 | 10 | 90 |
| 20 | 10 | 90 |
| 20.1 | 90 | 10 |
| 30 | 90 | 10 |

A particle size analysis was carried out on the Lecotrac laser particle size analyser. The results are shown in Table B along with the results from the starting material for comparison:

TABLE B

| | Particle Size Analysis | | | |
|---|---|---|---|---|
| | Pre-nanomilling | | Post-nanomilling | |
| Compound | 50% percentile (µ) | 95% percentile (µ) | 50% percentile (µ) | 95% percentile (µ) |
| Example 176 | 13.15 | 68.7 | 0.33 | 1.78 |

A dilution of nominally 15.0 mg/ml was prepared using 21.36 ml of the concentrate and (100−20.34)ml=83.64 ml of diluent (aqueous 1.5% HPMC).

Compounds of Examples 19, 34, 194, 217, 228, 247 were nanomilled on a 1 g scale using the process described above and the particle size analysed pre and post nanomilling. The results are given in Table C.

TABLE C

| | Pre-nanomilling | | Post-nanomilling | |
|---|---|---|---|---|
| Compound | 50% percentile (µ) | 95% percentile (µ) | 50% percentile (µ) | 95% percentile (µ) |
| Ex 247 | 13.2 | 68.7 | 0.64 | 2.53 |
| Ex 217 | 5.70 | 34.9 | 0.34 | 1.30 |
| Ex 19 | 5.22 | 25.5 | 0.40 | 1.40 |
|  | 4.65 | 47.1 | 0.44 | 1.69 |
|  | 6.78 | 33.7 | 0.56 | 1.97 |
|  | 10.46 | 32.7 | 0.18 | 0.56 |

Formulations for pharmaceutical use incorporating compounds of the present invention either pre or post nanomilling can be prepared in various forms and with numerous excipients. Examples of such formulations are given below.

EXAMPLE 267

Inhalant Formulation

A compound of formula (I) or a pharmaceutically acceptable derivative thereof, (1 mg to 100 mg) is aerosolized from a metered dose inhaler to deliver the desired amount of drug per use.

EXAMPLE 268

Tablet Formulation

| Tablets/Ingredients | Per Tablet |
|---|---|
| 1. Active ingredient (Compound of formula (I) or pharmaceutically acceptable derivative) | 40 mg |
| 2. Corn Starch | 20 mg |
| 3. Alginic acid | 20 mg |
| 4. Sodium Alginate | 20 mg |
| 5. Mg stearate | 1.3 mg |

Procedure for Tablet Formulation:

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 269

Parenteral Formulation

A pharmaceutical composition for parenteral administration is prepared by dissolving an appropriate amount of a compound of formula (I) in polyethylene glycol with heating. This solution is then diluted with water for injections Ph Eur. (to 100 ml). The solution is then rendered sterile by filtration through a 0.22 micron membrane filter and sealed in sterile containers.

The invention claimed is:
1. 2-(2,4-Dichlorophenylamino)-4-trifluoromethylpyrimidine-5-carboxylic acid (tetrahydropyran-4-ylmethyl)-amide or a pharmaceutically acceptable salt thereof.
2. The compound as claimed in claim 1 in nanoparticulate form.
3. 2-(2,4-Dichlorophenylamino)-4-trifluoromethylpyrimidine-5-carboxylic acid (tetrahydropyran-4-ylmethyl)-amide.
4. The compound as claimed in claim 3 in nanoparticulate form.
5. A pharmaceutical composition comprising 2-(2,4-dichlorophenylamino)-4-trifluoromethylpyrimidine-5-carboxylic acid (tetrahydropyran-4-ylmethyl)-amide or a pharmaceutically acceptable salt thereof.
6. The pharmaceutical composition as claimed in claim 5 further comprising a pharmaceutical carrier or diluent thereof.
7. The pharmaceutical composition as claimed in claim 6. further comprising a second therapeutic agent.
8. The pharmaceutical composition as claimed in claim 5 wherein the compound is in nanoparticulate form.
9. The pharmaceutical composition as claimed in claim 8 further comprising a pharmaceutical carrier or diluent thereof.
10. A pharmaceutical composition comprising 2-(2,4-dichlorophenylamino)-4-trifluoromethylpyrimidine-5-carboxylic acid (tetrahydropyran-4-ylmethyl)-amide.
11. The pharmaceutical composition as claimed in claim 10 further comprising a pharmaceutical carrier or diluent thereof.
12. The pharmaceutical composition as claimed in claim 11 further comprising a second therapeutic agent.
13. The pharmaceutical composition as claimed in claim 10 wherein the compound is in nanoparticulate form.
14. The pharmaceutical composition as claimed in claim 13 further comprising a pharmaceutical carrier or diluent thereof.
15. The pharmaceutical composition as claimed in claim 14 further comprising a second therapeutic agent.
16. A method of treating a human or animal subject suffering from pain selected from the group consisting of inflammatory pain, visceral pain, cancer pain, neuropathic pain, post operative pain, acute pain, rheumatoid arthritic pain, and osteoarthritic pain, which comprises administering to said subject a therapeutically effective amount of 2-(2,4-dichlorophenylamino)-4-trifluoromethylpyrimidine-5-carboxylic acid (tetrahydropyran-4-ylmethyl)-amide or a pharmaceutically acceptable salt thereof.
17. The method claimed claim 16 wherein the condition is osteoarthritic pain.
18. A method of treating a human or animal subject suffering from an inflammatory bowel disease which comprises administering to said subject a therapeutically effective amount of 2-(2,4-dichlorophenylamino)-4-trifluoromethylpyrimidine-5-carboxylic acid (tetrahydropyran-4-ylmethyl)-amide or a pharmaceutically acceptable salt thereof.
19. The method as claimed claim 18 wherein the inflammatory bowel disease is selected from the group consisting of Crohn's disease and ulcerative colitis.

* * * * *

UNITED STATES PATENT AND TRADEMARK OFFICE
CERTIFICATE OF CORRECTION

| | | |
|---|---|---|
| PATENT NO. | : 7,635,701 B2 | Page 1 of 1 |
| APPLICATION NO. | : 10/524470 | |
| DATED | : December 22, 2009 | |
| INVENTOR(S) | : Eatherton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 850 days.

Signed and Sealed this
Eleventh Day of January, 2011

David J. Kappos
*Director of the United States Patent and Trademark Office*